(12) United States Patent
Pavliak et al.

(10) Patent No.: US 7,537,766 B2
(45) Date of Patent: May 26, 2009

(54) NEISSERIA MENINGITIDIS INNER CORE LIPO-OLIGOSACCHARIDE EPITOPES, MULTIVALENT CONJUGATES THEREOF AND IMMUNOGENIC COMPOSITIONS THEREOF

(75) Inventors: Viliam Pavliak, Montebello, NY (US); Mario Artur Monteiro, Guelph (CA); Maria Fortuna-Nevin, Webster, NY (US)

(73) Assignee: Wyeth, Madison, NJ (US)

( * ) Notice: Subject to any disclaimer, the term of this patent is extended or adjusted under 35 U.S.C. 154(b) by 262 days.

(21) Appl. No.: 11/212,307

(22) Filed: Aug. 26, 2005

(65) Prior Publication Data

US 2006/0047106 A1      Mar. 2, 2006

Related U.S. Application Data

(60) Provisional application No. 60/606,151, filed on Aug. 30, 2004.

(51) Int. Cl.
*A61K 39/00* (2006.01)
*A61K 39/38* (2006.01)
*A61K 39/116* (2006.01)
*A61K 39/385* (2006.01)

(52) U.S. Cl. .............. 424/184.1; 424/192.1; 424/193.1; 424/203.1

(58) Field of Classification Search .............. 424/184.1, 424/192.1, 193.1, 203.1
See application file for complete search history.

(56) References Cited

U.S. PATENT DOCUMENTS 5,705,161 A    1/1998   Van Der Ley et al.

OTHER PUBLICATIONS

Mario A. Monteiro, et al., "Phase-variation of the truncated lipo-oligosaccharide of *Neisseria meningitidis* NMD phosphoglucomutase isogenic mutatn NMB-R6," Carbohydrate Research, 2003, 338: 2905-2912.

A.F.M. Verheul, et al., "Minimal Oligosaccharide Structures Required for Induction of Immune Responses against Meningococcal Immunotype L1, L2, and L3, 7, 9 Lipopolysaccharides Determined by Using Synthetic Oligosaccharide-Protein Conjugates," Infection and Immunity, 1991, 59(10): 3566-3573.

Jose L. Difabio, et al., "Structure of the L1 and L6 core oligosaccharide epitopes of *Neisseria meningitidis*," Canadian Journal of Chemistry, 1989, 68(5):1029-1034.

Francis Michon, et al., "Structure of the L5 Lipopolysaccharide Core Oligosaccharides of *Neisseria meningitidis*," The Journal of Biological Chemistry, 1990, 265(13): 7243-7247.

M. Mahbubar Rahman, et al., "The lipooligosaccharide (LOS) of *Neisseria meningitidis* Serogroup B Strain NMB contains L2, L3, and novel oligosaccharides, and lacks the lipid-A 4'-phosphate substituent," Carbohydrate Research, 1998, 307: 311-324.

Andrew D. Cox, et al., "Structural analysis of the lipopolysaccharide from *Neisseria meningitidis* strain BZ 157 galE: location of two phosphoethanolamine residues in the inner core oligosaccharide," Carbohydrate Research, 2002, 337: 1435-1444.

Andrew D. Cox, et al., "Identification and localization of glycine in the inner core lipopolysaccharide of *Neisseria meningitidis*," European Journal of Biochemistry, 2002, 269:4169-4175.

Andrew D. Cox, et al., "Identification of a novel inner-core oligosaccharide structure in *Neisseria meningitidis* lipopolysaccharide," European Journal of Biochemistry, 2003, 270: 1759-1766.

Chao-Ming Tsai, et al., "Immunotype Epitopes of *Neisseria meningitidis* Lipooligosaccharide Types 1 through 8," Infection and Immunity, 1987, 55(7): 1652-1656.

Janice J. Kim, et al., "Electromorphic Characterization and Description of Conserved Epitopes of the Lipooligosaccharides of Group A *Neisseria meningitidis*," Infection and Immunity, 1988, 56(10): 2631-2638.

Chao-Ming Tsai, et al., "Heterogeneity and Variation Among *Neisseria meningitidis* Lipopolysaccharides," Journal of Bacteriology, 1983, 155(2): 498-504.

*Primary Examiner*—Mark Navarro
(74) *Attorney, Agent, or Firm*—Kelly M. Sullivan; Royal N. Ronning, Jr.

(57) ABSTRACT

The present invention is directed to novel *Neisseria meningitidis* lipo-oligosaccharide inner core molecules, conjugates thereof and immunogenic compositions thereof. In particular embodiments, the invention relates to multivalent immunogenic compositions comprising five distinct *Neisseria meningitidis* inner core lipo-oligosaccharide epitope groups, wherein the multivalent compositions induce cross-reactive immune responses against *Neisseria meningitidis* lipo-oligosaccharide immunotypes.

64 Claims, 13 Drawing Sheets

NEISSERIA MENINGITIDIS INNER CORE LIPO-OLIGOSACCHARIDE EPITOPES, MULTIVALENT CONJUGATES THEREOF AND IMMUNOGENIC COMPOSITIONS THEREOF

This application claims the benefit under 35 U.S.C. §119(e) to U.S. provisional application No. 60/606,151, filed Aug. 30, 2004, which is hereby incorporated by reference in its entirety.

FIELD OF THE INVENTION

The present invention generally relates to the fields of bacteriology, carbohydrates, infectious disease and immunology. More particularly, the invention relates to novel *Neisseria meningitidis* inner core lipo-oligosaccharide epitopes, conjugates thereof and immunogenic compositions thereof. In particular embodiments, the invention relates to multivalent immunogenic compositions comprising structurally distinct *Neisseria meningitidis* inner core lipo-oligosaccharide epitopes, wherein the multivalent compositions induce cross-reactive immune responses against *Neisseria meningitidis* lipo-oligosaccharide immunotypes.

BACKGROUND OF THE INVENTION

*Neisseria meningitidis* is a causative agent of bacterial meningitis and sepsis. Meningococcal disease annually causes an estimated 500,000 cases and 50,000 deaths worldwide (Plested et al., 2001). Serologically, *N. meningitidis* are separated into different antigenic groups based on the structure of their outer membrane protein (e.g., serotype class 2/3 outer membrane protein), their capsular polysaccharide (e.g., serogroups A, B, C, Y, W-135, X, Y, Z and 29E) and their lipo-oligosaccharide (e.g., immunotypes L1-L12).

*N. meningitidis* serogroups A, B, and C are responsible for approximately ninety percent of cases of meningococcal meningitis. Among *N. meningitidis* strains, at least twelve lipo-oligosaccharide (LOS) immunotypes (L1-L12) have been identified. The L1-L7 immunotypes are exclusively associated with group B and C meningococci, whereas the L10-L12 immunotypes are associated with group A meningococci. Only two immunotypes, L8 and L9, overlap between the groups. The most frequent LOS immunotypes among clinical isolates are L2, L3, L4, and L7 in North America (Zollinger and Mandrell, 1977) and L1, L2, L3, L7 and L9 in Europe (Verheul et al., 1993$^a$) (e.g., ninety five percent of the *N. meningitidis* isolates in Norwegian patients expressed the L3,7,9 immunotype (Anderson et al., 1997)).

Success in the prevention of group A, C, Y, and W-135 meningococcal meningitis in certain age groups has been achieved using monovalent and multivalent polysaccharide immunogenic compositions. However, serogroup A, C, W-135 and Y capsular polysaccharide compositions are generally not effective in children less than two years of age, the population most at risk of meningococcal disease.

*N. meningitidis* group B accounts for approximately fifty percent of bacterial meningitis in infants and children residing in the U.S. and Europe. In adolescents, experimental *N. meningitidis* group B immunogenic compositions consisting of outer membrane protein vesicles have been found to be approximately fifty percent protective. However, no protection has been observed when these outer membrane protein vesicles are administered to infants and children, the age groups at greatest risk of meningococcal disease.

Further complicating the development of immunogenic composition against *N. meningitidis* is the high inter-strain and intra-strain variation in the LOS outer core structure, thereby resulting in extensive antigenic diversity and poor immunogenicity. For example, phase variation can produce heterogeneous oligosaccharide chains, thereby changing the antigenic profile of *N. meningitidis* strains. Furthermore, the terminal galactose residue of the oligosaccharide (OS) outer core structure of most *N. meningitidis* immunotypes comprises a lacto-N-tetraose unit which mimics certain human blood group antigens (Mandrel et al., 1988), potentially reducing immunogenicity and/or inducing an autoimmune response.

Thus, there is currently a need in the art for immunogenic compositions which can elicit immune responses against the predominant *Neisseria meningitidis* serogroups A, B, C, Y and/or W-135.

SUMMARY OF THE INVENTION

In certain embodiments, the invention is directed to a novel di-phosphoethanolamine (di-PEA) epitope structure covalently linked to the β-chain heptose (HepII) residue of *Neisseria meningitidis* lipo-oligosaccharide (LOS) molecules. In other embodiments, the invention is directed to a novel di-phosphoethanolamine (di-PEA) epitope group comprised of a co-mixture of di-PEA residues (i.e., PEA-3-HepII-6-PEA and PEA-3-HepII-7-PEA). In another embodiment, the invention relates to novel immunogenic compositions which induce an immune response against *N. meningitidis* immunotypes L1-L12, thereby providing a broad immunogenic response against the predominant *N. meningitidis* serogroups A, B, C, Y and/or W-135. In certain other embodiments, the invention relates to multivalent *N. meningitidis* LOS conjugates, wherein the LOS molecules are conjugated to a carrier protein such as $CRM_{197}$ via a 2-keto-3-deoxyoctulosonic acid (KDO) of the LOS molecule. In yet other embodiments, the invention relates to one or more of the novel LOS inner core molecules admixed with one or more *N. meningitidis* ORF 2086 proteins.

Thus, in certain embodiments, the invention is directed to an isolated and purified *N. meningitidis* LOS inner core molecule comprising the following structure:

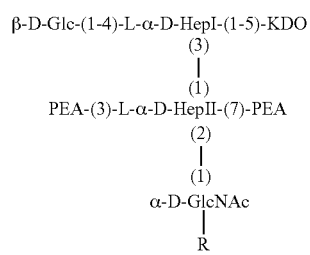

wherein PEA is 2-aminoethyl phosphate, Glc is D-glucopyranose, KDO is 2-keto-3-deoxyoctonate, Hep is L-glycero-D-manno-heptose, GlcNAc is N-acetylglucosamine and R is O-Acetyl or H. In certain embodiments, the inner core molecule further comprises a lipid-A component covalently attached to the KDO residue of the inner core. In other embodiments, the lipid-A component is de-O-acylated.

In yet other embodiments, the LOS inner core molecule is isolated from a *N. meningitidis* strain having a mutation in one or more genes selected from the group consisting of galE, pgm and rfaK. In certain other embodiments, at least one mutation is a galE mutation. In still other embodiments, the inner core molecule is conjugated to a carrier protein. In a particular embodiment, the inner core molecule is conjugated to a carrier protein by means of a linker molecule. In another embodiment, the inner core molecule is covalently attached to the linker molecule at a carboxylic acid of a KDO residue of the inner core. In one particular embodiment, the linker molecule is 3-(2-pyridyidithio)-propionyl hydrazide (PDPH).

In other embodiments, the inner core molecule is conjugated to a carrier protein selected from the group consisting of a tetanus toxin, a diphtheria toxin, a mutant diphtheria toxin, a $CRM_{197}$ protein, a pseudomonas exotoxin A protein, a cholera toxin (CT) protein, a cholera toxin mutant CT-E29H protein, a Group A streptococcal toxin protein, a *Streptococcus pneumoniae* pneumolysin protein, a filamentous haemagglutinin (FHA) protein, a *Bordetella pertussis* FHA fragment protein, a *N. gonorrheae* pilin protein, a *N. meningitidis* pilin protein, a *N. gonorrheae* outer membrane protein, a *N. meningitidis* ORF 2086 protein, a *Streptococcus* C5a peptidase and a staphylococcal MSCRAMM protein. In one particular embodiment, the carrier protein is a $CRM_{197}$ protein, a *Streptococcus* C5a peptidase or a *N. meningitidis* ORF 2086 protein. In other embodiments, the inner core molecule is admixed or formulated with one or more *N. meningitidis* ORF 2086 proteins.

In certain other embodiments, the invention is directed to an isolated and purified LOS inner core composition comprising a co-mixture of at least (i) a *N. meningitidis* LOS inner core molecule comprising β-chain heptose residue (HepII) residue comprising an O-3 linked 2-aminoethyl phosphate (PEA) and an O-6 linked PEA and (ii) a *N. meningitidis* LOS inner core molecule comprising a HepII residue comprising an O-3 linked PEA and an O-7 linked PEA. In one particular embodiment, LOS inner core molecules (i) and (ii) comprise the following structures:

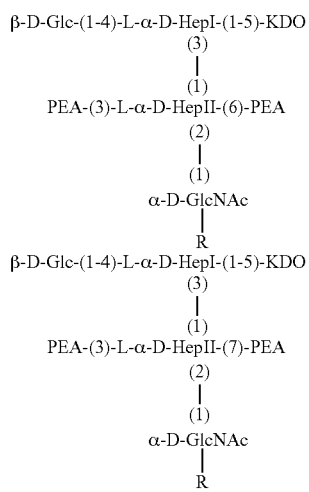

wherein Glc is D-glucopyranose, KDO is 2-keto-3-deoxyoctonate, Hep is L-glycero-D-manno-heptose, GlcNAc is N-acetylglucosamine and R is O-Acetyl or H. In another embodiment, the inner core composition further comprises one or more LOS inner core molecules of the following structures:

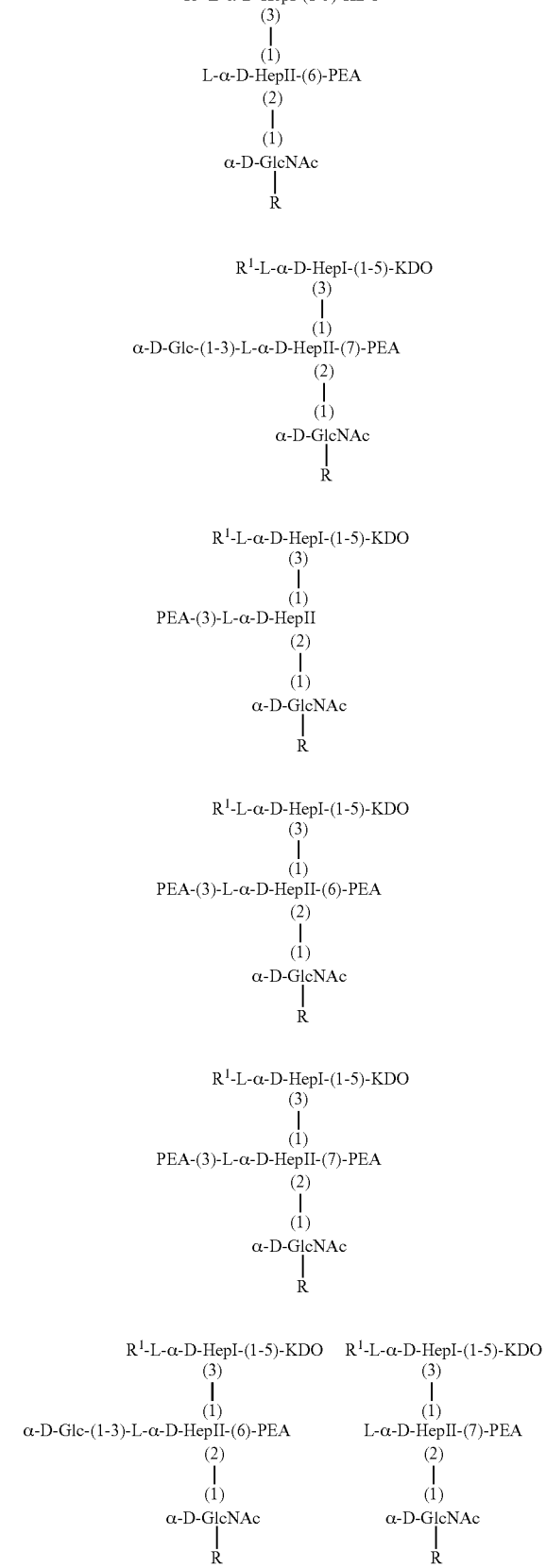

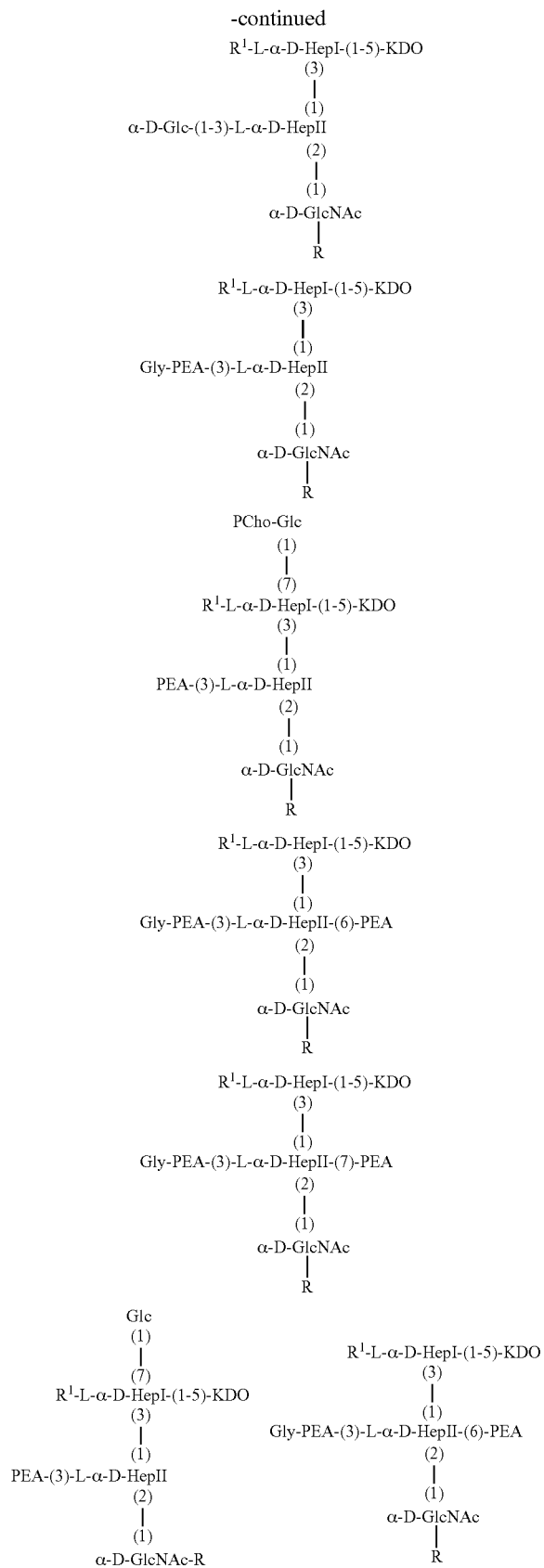

where Glc is D-glucopyranose, KDO is 2-keto-3-deoxyoctonate, Hep is L-glycero-D-manno-heptose, GlcNAc is N-acetylglucosamine, Gly is glycine, PCho is phosphorylcholine, R is O-Acetyl or H and $R^1$ is β-D-Glc-(1-4), Glc-(1-4)-β-D-Glc-(1-4) or H.

In another embodiment, the inner core composition further comprises a lipid-A component covalently attached to a KDO residue of one or more of the inner core molecules. In certain embodiments, the lipid-A portion is de-O-acylated. In yet other embodiments, the inner core molecules are isolated from a N. meningitidis strain having a mutation in one or more genes selected from the group consisting of galE, pgm and rfaK. In one particular embodiment, at least one mutation is a galE mutation.

In still other embodiments, the inner core molecules are conjugated to a carrier protein. In certain embodiments, the inner core molecules are conjugated to a carrier protein by means of a linker molecule. In certain embodiments, the inner core molecules are covalently attached to the linker molecule at a carboxylic acid of a KDO residue of the inner core. In one particular embodiment, the linker molecule is PDPH. In yet another embodiment, the carrier protein is selected from the group consisting of a tetanus toxin, a diphtheria toxin, a mutant diphtheria toxin, a $CRM_{197}$ protein, a pseudomonas exotoxin A protein, a cholera toxin (CT) protein, a cholera toxin mutant CT-E29H protein, a Group A streptococcal toxin protein, a *Streptococcus pneumoniae* pneumolysin protein, a filamentous haemagglutinin (FHA) protein, a *Bordetella pertussis* FHA fragment protein, a *N. gonorrheae* pilin protein, a *N. meningitidis* pilin protein, a *N. gonorrheae* outer membrane protein, a *N. meningitidis* ORF 2086 protein, a *Streptococcus* C5a peptidase and a staphylococcal MSCRAMM protein. In one particular embodiment, the carrier protein is a $CRM_{197}$ protein, a *Streptococcus* C5a peptidase or a *N. meningitidis* ORF 2086 protein. In another particular embodiment, the inner core composition further comprises one or more *N. meningitidis* ORF 2086 proteins.

Certain other embodiments of the invention are directed to an immunogenic composition comprising (i) a *N. meningitidis* LOS inner core molecule comprising a HepII residue comprising an O-3 PEA and an O-6 linked PEA and (ii) a *N. meningitidis* LOS inner core molecule comprising a HepII residue comprising an O-3 linked PEA and an O-7 linked PEA. In one particular embodiment, the inner core molecules (i) and (ii) of the immunogenic composition comprise the following structures:

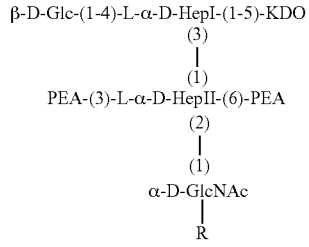

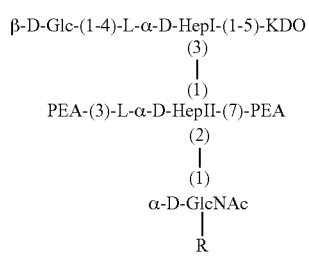

wherein Glc is D-glucopyranose, KDO is 2-keto-3-deoxyoctonate, Hep is L-glycero-D-manno-heptose, GlcNAc is N-acetylglucosamine and R is O-Acetyl or H.

In another embodiment, the immunogenic composition further comprises one or more *N. meningitidis* LOS inner core molecules of the following structures:

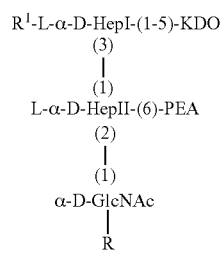

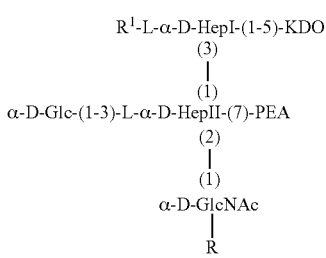

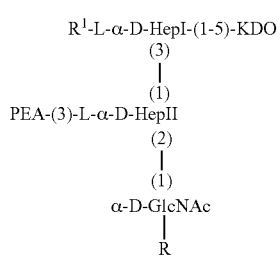

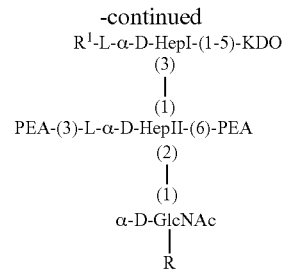

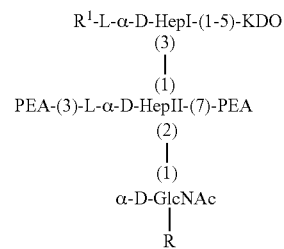

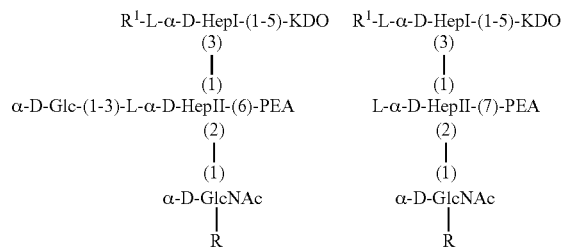

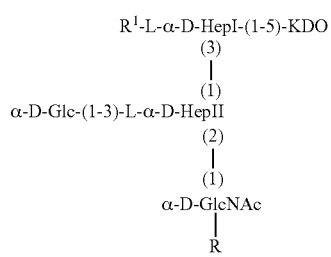

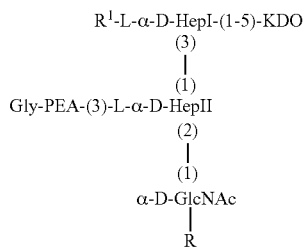

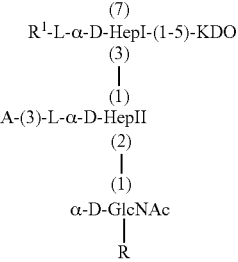

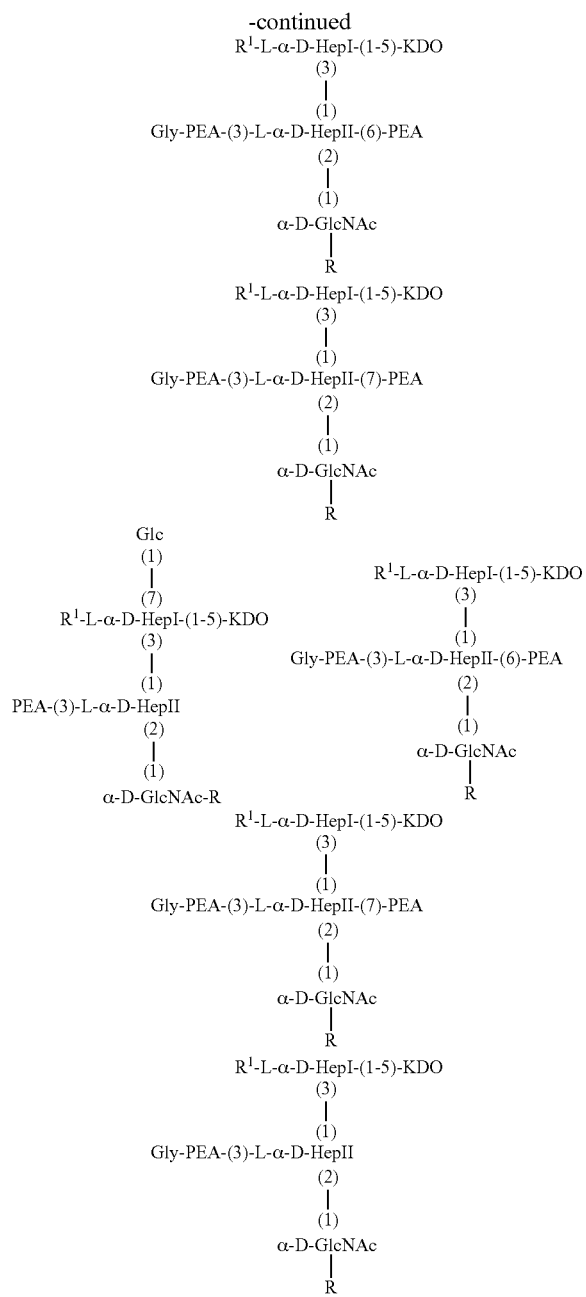

wherein Glc is D-glucopyranose, KDO is 2-keto-3-deoxyoctonate, Hep is L-glycero-D-manno-heptose, GlcNAc is N-acetylglucosamine, Gly is glycine, PCho is phosphorylcholine, R is O-Acetyl or H and $R^1$ is β-D-Glc-(1-4), Glc-(1-4)-β-D-Glc-(1-4) or H.

In other embodiments, the immunogenic composition further comprises a lipid-A component covalently attached to a KDO residue of the inner core. In certain other embodiments, the composition is formulated as a liposome. In another embodiment, the lipid-A component is de-O-acylated. In still other embodiments, the inner core molecules are isolated from a *N. meningitidis* strain having a mutation in one or more genes selected from the group consisting of galE, pgm and rfaK. In one particular embodiments, at least one mutation is a galE mutation. In still other embodiments, the inner core molecules are conjugated to a carrier protein. In certain embodiments, the inner core molecules are conjugated to a carrier protein by means of a linker molecule. In certain other embodiments, the inner core molecules are covalently attached to the linker molecule at a carboxylic acid of a KDO residue of the inner core. In one particular embodiment, the linker molecule is PDPH.

In other embodiments, the carrier protein is selected from the group consisting of a tetanus toxin, a diphtheria toxin, a mutant diphtheria toxin, a $CRM_{197}$ protein, a pseudomonas exotoxin A protein, a cholera toxin (CT) protein, a cholera toxin mutant CT-E29H protein, a Group A streptococcal toxin protein, a *Streptococcus pneumoniae* pneumolysin protein, a filamentous haemagglutinin (FHA) protein, a *Bordetella pertussis* FHA fragment protein, a *N. gonorrheae* pilin protein, a *N. meningitidis* pilin protein, a *N. gonorrheae* outer membrane protein, a *N. meningitidis* ORF 2086 protein, a *Streptococcus* C5a peptidase and a staphylococcal MSCRAMM protein. In certain embodiments, the carrier protein is a $CRM_{197}$ protein, a *Streptococcus* C5a peptidase or a *N. meningitidis* ORF 2086 protein.

In yet other embodiments, the immunogenic composition further comprises one or more adjuvants. In certain embodiments, the one or more adjuvants are selected from the group consisting of GM-CSF, 529SE, 529AF, IL-12, aluminum phosphate, aluminum hydroxide, *Mycobacterium tuberculosis*, *Bordetella pertussis*, bacterial lipopolysaccharides, aminoalkyl glucosamine phosphate compounds, MPL (3-O-deacylated monophosphoryl lipid A), Quil A, STIMULON™ QS-21, a pertussis toxin (PT), an *E. coli* heat-labile toxin (LT), a cholera toxin (CT), IL-1 α, IL-1 β, IL-2, IL-4, IL-5, IL-6, IL-7, IL-8, IL-10, IL-13, IL-14, IL-15, IL-16, IL-17, IL-18, interferon-α, interferon-β, interferon-γ, granulocyte colony stimulating factor, tumor necrosis factor α and tumor necrosis factor β.

In another embodiment, the immunogenic composition further comprises one or more antigens selected from the group consisting of a polypeptide, a polypeptide fragment, a carbohydrate, an oligosaccharide, a lipid, a lipooligosaccharide, a polysaccharide, a capsular polysaccharide, an oligosaccharide-protein conjugate, a polysaccharide-protein conjugate, a peptide-protein conjugate, an oligosaccharide-peptide conjugate, a polysaccharide-peptide conjugate, a protein-protein conjugate, a lipooligosaccharide-protein conjugate and a polysaccharide-protein conjugate. In one particular embodiment, the one or more antigens are isolated from *N. meningitidis*. In certain embodiments, one of the one or more antigens isolated from *N. meningitidis* is a ORF 2086 protein. In one particular embodiment, an immunogenic composition of the invention comprises one or more *N. meningitidis* ORF 2086 proteins.

In certain embodiments, the invention is directed to a method of immunizing a mammal against meningococcal disease comprising administering to the mammal an immunogenic amount of a LOS inner core composition of the invention. In other embodiments, the immunogenic composition is administered by a route selected from the group consisting of intradermal, intramuscular, intravenous, intraperitoneal, subcutaneous, intranasal, vaginal, ocular and oral.

In another embodiment, the invention is directed to a method for preparing a hyperimmune globulin composition comprising the steps of (a) immunizing a mammal with an immunogenic composition comprising LOS inner core molecules having the following structures:

β-D-Glc-(1-4)-L-α-D-HepI-(1-5)-KDO
(3)
|
(1)
PEA-(3)-L-α-D-HepII-(6)-PEA
(2)
|
(1)
α-D-GlcNAc
|
R

β-D-Glc-(1-4)-L-α-D-HepI-(1-5)-KDO;
(3)
|
(1)
PEA-(3)-L-α-D-HepII-(7)-PEA
(2)
|
(1)
α-D-GlcNAc
|
R (b) collecting plasma from the immunized mammal and (c) harvesting from the plasma a hyperimmune serum globulin specific for an LOS inner core molecule. In certain embodiments, the immunogenic composition of step (a) further comprises one or more LOS inner core molecules comprising the following structures:

R¹-L-α-D-HepI-(1-5)-KDO
(3)
|
(1)
L-α-D-HepII-(6)-PEA
(2)
|
(1)
α-D-GlcNAc
|
R

R¹-L-α-D-HepI-(1-5)-KDO
(3)
|
(1)
α-D-Glc-(1-3)-L-α-D-HepII-(7)-PEA
(2)
|
(1)
α-D-GlcNAc
|
R

R¹-L-α-D-HepI-(1-5)-KDO
(3)
|
(1)
PEA-(3)-L-α-D-HepII
(2)
|
(1)
α-D-GlcNAc
|
R

-continued

R¹-L-α-D-HepI-(1-5)-KDO
(3)
|
(1)
PEA-(3)-L-α-D-HepII-(6)-PEA
(2)
|
(1)
α-D-GlcNAc
|
R

R¹-L-α-D-HepI-(1-5)-KDO
(3)
|
(1)
PEA-(3)-L-α-D-HepII-(7)-PEA
(2)
|
(1)
α-D-GlcNAc
|
R

R¹-L-α-D-HepI-(1-5)-KDO          R¹-L-α-D-HepI-(1-5)-KDO
(3)                                (3)
|                                  |
(1)                                (1)
α-D-Glc-(1-3)-L-α-D-HepII-(6)-PEA   L-α-D-HepII-(7)-PEA
(2)                                (2)
|                                  |
(1)                                (1)
α-D-GlcNAc                         α-D-GlcNAc
|                                  |
R                                  R

R¹-L-α-D-HepI-(1-5)-KDO
(3)
|
(1)
α-D-Glc-(1-3)-L-α-D-HepII
(2)
|
(1)
α-D-GlcNAc
|
R

R¹-L-α-D-HepI-(1-5)-KDO
(3)
|
(1)
Gly-PEA-(3)-L-α-D-HepII
(2)
|
(1)
α-D-GlcNAc
|
R

PCho-Glc
(1)
|
(7)
R¹-L-α-D-HepI-(1-5)-KDO
(3)
|
(1)
PEA-(3)-L-α-D-HepII
(2)
|
(1)
α-D-GlcNAc
|
R

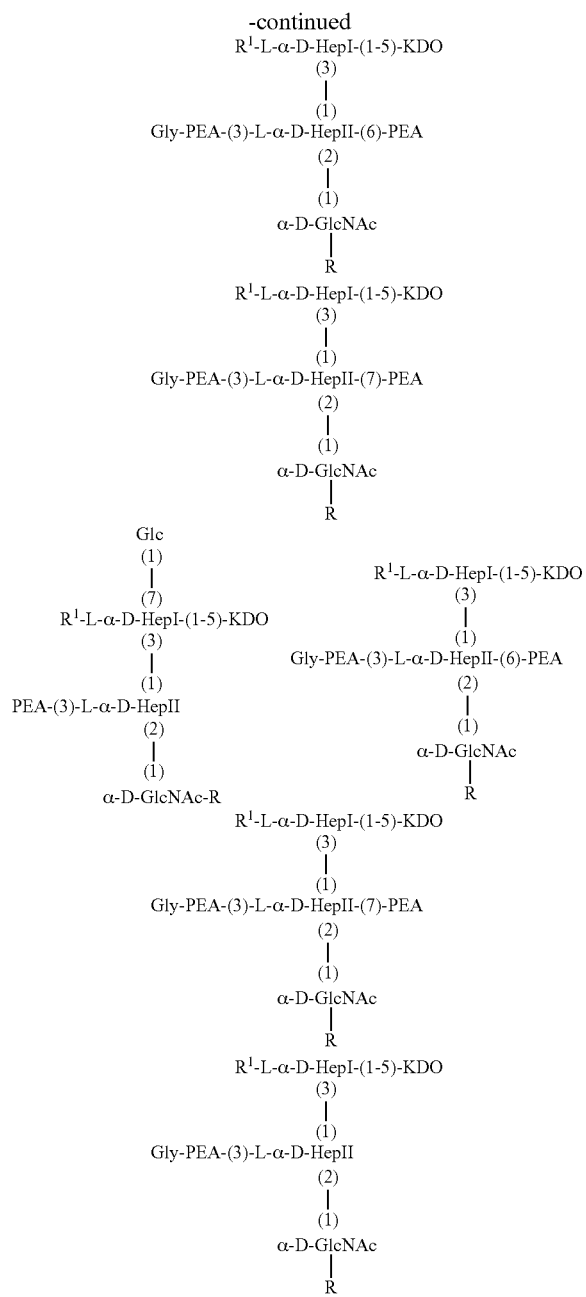

wherein Glc is D-glucopyranose, KDO is 2-keto-3-deoxyoctonate, Hep is L-glycero-D-manno-heptose, GlcNAc is N-acetylglucosamine, Gly is glycine, PCho is phosphorylcholine, R is O-Acetyl or H and $R^1$ is β-D-Glc-(1-4), Glc-(1-4)-β-D-Glc-(1-4) or H.

In still other embodiments, the invention is directed to a hyperimmune globulin produced according to the method for preparing the hyperimmune globulin composition set forth above. In yet other embodiments, the invention is directed to a method of passively immunizing a mammal against meningococcal disease comprising administering to the mammal a hyperimmune globulin of the invention.

In other embodiments, the invention is directed to a process for conjugating one or more inner core molecules of the invention to a carrier protein by means of a linker molecule, wherein the inner core molecule is covalently attached to the linker molecule at the carboxylic acid of a 2-keto-3-deoxyoctonate (KDO) residue of the inner core, the process comprising the steps of (a) activating the carboxylic acid of a KDO residue with carbodiimide, thiolating the activated carboxylate with 3-(2-pyridyidithio)-propionyl hydrazide (PDPH) and reducing the PDPH disulfide bond with a reducing agent; (b) activating the amine groups of the lysine residues of the carrier protein with bromoacetyl succinamide; (c) mixing the LOS-PDPH of step (a) with the bromoacetylated protein of step (b) under conjugating conditions, thereby forming a LOS-PDPH-protein conjugate, and (d) capping or blocking the un-reacted lysine amine groups with $H_2N-CH_2-CH_2-SH.HCl$.

Other features and advantages of the invention will be apparent from the following detailed description and the claims.

DETAILED DESCRIPTION OF THE INVENTION

Figure 1:
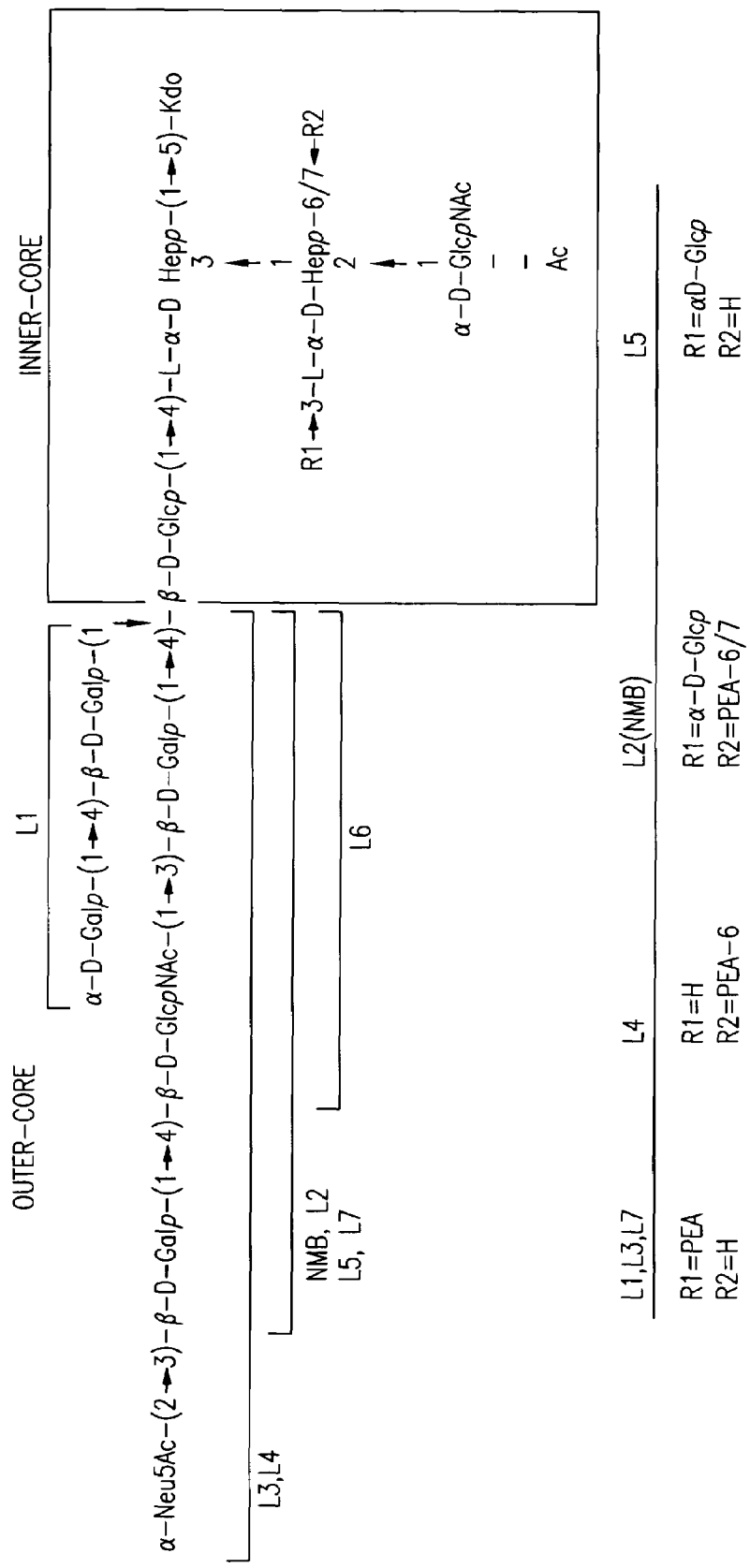
FIG. 1 shows a structural scheme of the outer and inner core of an LOS molecule lacking the lipid-A component and the structural variations of LOS immunotypes L1, L2 (NMB), L3, L4, L5, L6 and L7.

The present invention addresses a need in the art for immunogenic compositions which are capable of inducing an immune response against the predominant *Neisseria meningitidis* serogroups A, B, C, Y and/or W-135. The invention described herein has identified *N. meningitidis* lipo-oligosaccharide (hereinafter, "LOS") molecules comprising novel LOS inner core epitopes. More specifically, in one embodiment of the invention, a novel di-phosphoethanolamine (di-PEA) epitope structure has been identified, wherein the two PEA residues are covalently linked to the β-chain heptose (hereinafter, "HepII") residue of *N. meningitidis* LOS molecules. *N. meningitidis* LOS molecules comprising the novel di-PEA epitope have the following inner core structure:

```
β-D-Glc-(1-4)-L-α-D-HepI-(1-5)-KDO
              (3)
               |
              (1)
PEA-(3)-L-α-D-HepII-(7)-PEA
              (2)
               |
              (1)
          α-D-GlcNAc
               |
               R
``` wherein Glc is D-glucopyranose, KDO is 2-keto-3-deoxyoctonate, Hep is L-glycero-D-manno-heptose, GlcNAc is N-acetylglucosamine and R is O-Acetyl or H.

In certain other embodiments, the invention is directed to a novel di-PEA epitope group comprised of a co-mixture of di-PEA residues (i.e., a co-mixture of PEA-3-HepII-6-PEA and PEA-3-HepII-7-PEA). In other embodiments, the invention has determined the minimal requisite *N. meningitidis* LOS inner core epitope groups needed in a multivalent immunogenic composition, wherein the multivalent composition induces an immune response against all twelve of the presently known *N. meningitidis* immunotypes (i.e., immunotypes L1-L12), thereby providing a broad immunogenic response against the predominant *Neisseria meningitidis* serogroups A, B, C, Y and/or W-135. In certain other embodiments, the invention relates to multivalent *N. meningitidis* LOS conjugates and immunogenic compositions thereof, wherein the LOS molecules are conjugated to a carrier protein (e.g., $CRM_{197}$) via a KDO residue of the LOS molecule. In another embodiment, the invention is directed to immunogenic compositions comprising one or more of the LOS inner core epitopes and one or more *N. meningitidis* ORF 2086 protein.

A. *Neisseria Meningitidis* LIPO-Oligosaccharide Molecules

*Neisseria meningitidis* produces LOS molecules which are associated with the bacterial outer membrane. These LOS molecules comprise a core oligosaccharide (OS) component and a lipid-A component. The core OS component comprises an inner core portion and an outer core portion (e.g., see FIG. 1), wherein the OS core (i.e., the inner core+the outer core portions) is made up of glucose (Glc), galactose (Gal), 3-keto-2-deoxyoctanoic acid (KDO), glucosamine (GlcNAc), galactoseamine (GalNAc), sialic acid, phosphoethanolamine (PEA) and L-glycero-D-manno-heptose.

The outer core portion of the OS core comprises phase variable oligosaccharide moieties of variable length, often bearing NeuNAcα(2-3)Galα(1-4)GlcNAcβ(1-3)Galβ(1-4)Glcβ (i.e., sialyllacto-N-neotetraose), Galβ(1-4)GlcNAcβ(1-3)Galβ(1-4)Glcβ (i.e., lacto-N-neotetraose or LNnT), NeuNAcα(2-6)Galα(1-4)Galβ(1-4)Glcβ (i.e., sialylp$^k$), Galα(1-4)Galβ(1-4)Glcβ (i.e., p$^k$ antigen) and/or Galβ(1-4)Glcβ (i.e., LacCer) at its non-reducing termini.

The inner core portion of the OS core comprises a di-heptose-N-glucosamine backbone, wherein the two L-glycero-D-manno-heptose residues (hereinafter, "HepI" and "HepII" residues) provide a point of attachment for the oligosaccharide residues of the outer core OS portion. As defined hereinafter, the terms "HepI" residue, "proximal heptose" residue and "α-chain heptose" residue are used interchangeably. Similarly, as defined hereinafter, the terms "HepII" residue, "distal heptose" residue and "β-chain heptose" residue are used interchangeably. The lipid-A component of the LOS (which is embedded in the outer membrane of *N. meningitidis*) is attached to a KDO of the HepI residue.

*N. meningitidis* strains are serologically separated into different antigenic groups based on the structure of their outer membrane protein (serotype), their capsular polysaccharide (serogroup) and their LOS (immunotype). *N. meningitidis* LOS molecules have been classified into twelve distinct immunotypes (L1-L12) based on monoclonal antibody reactivities (Scholten et al., 1994). Many of the LOS immunotypes have also been structurally characterized (e.g., L1 and L6 (Di Fabio et al., 1990; Wakarchuh et al., 1998); L2, (Gamian et al., 1992); L3 (Pavliak et al., 1993); L4 and L7 (Kogan et al., 1997); L5 (Michon et al., 1990) and L9 (Jennings et al., 1983)) and it has been suggested that structural features of the LOS molecules dictate immunotyping (e.g., the length and nature of the oligosaccharide extension from HepI, the presence or absence of a Glc sugar at HepII and the presence or absence of PEA at HepII).

The LOS molecules of *N. meningitidis* were originally referred to in the literature as lipo-polysaccharide (LPS) molecules. The two molecules (i.e., LOS and LPS) are often used interchangeably in the art when referring to *N. meningitidis* lipo-oligosaccharides. However, *N. meningitidis* lacks the biosynthetic machinery to produce an O-chain (or O-antigen) polysaccharide (typical of LPS molecules) and thus produces solely LOS molecules. Thus, for clarity and consistency, the terms "LOS" or "LOS molecules" are used hereinafter when referring to *N. meningitidis* molecules comprising an OS core and a lipid-A.

B. *Neisseria Meningitidis* Inner Core Epitopes

The invention described hereinafter has identified *N. meningitidis* LOS molecules comprising a novel inner core epitope structure, wherein the novel structure comprises two PEA (di-PEA) units simultaneously attached to the HepII residue of the inner core. As defined hereinafter, the terms "phosphoethanolamine" and "2-aminoethyl phosphate" are the same molecule and are abbreviated hereinafter with the acronym "PEA". As defined hereinafter, the term "di-PEA" refers to two PEA residues attached to the same HepII residue (i.e., simultaneously attached) of the inner core.

In certain embodiments, the invention has identified a novel di-PEA epitope group comprised of a co-mixture of di-PEA residues (i.e., a co-mixture of PEA-3-HepII-6-PEA and PEA-3-HepII-7-PEA). In another embodiment, the invention has identified the minimal requisite LOS inner core epitope groups needed in a multivalent immunogenic composition (e.g., see Table 1 below), wherein the multivalent composition induces an immune response against all twelve of the presently known *N. meningitidis* immunotypes (i.e., immunotypes L1-L12), thereby providing a broad (e.g., cross-reactive) immunogenic response against the predominant *N. meningitidis* serogroups A, B, C, Y and/or W-135.

For example, monoclonal and polyclonal antibody binding studies (Example 2) indicated that *N. meningitidis* LOS molecules comprise at least five distinct epitope groups, summarized below:

1. An epitope present on LOS immunotypes L1, L3 (strain 6275), L9, L11, L12 and strain A1 (L8), recognized by monoclonal antibody (MAb) MB2-380-91, MB2-134-19 and MB2-14-13;
2. An epitope present on LOS immunotypes L2 and NMB, recognized by MAb LOS-556-24, LOS-1345-33 and LOS 1622;
3. An epitope present on LOS immunotypes L4 and L6, recognized by polyclonal rabbit antisera directed against L4 LOS;
4. An epitope present on LOS immunotype L5, recognized by polyclonal rabbit antisera directed against L5 LOS, and
5. An epitope present on LOS immunotypes L7, L8 (strain M978), strain H44/76 (L3) and L10, not recognized by any antibodies tested.

The data presented in Example 4 further demonstrated that (a) the five distinct epitopes are located in the LOS inner core, (b) antibody binding to these epitopes is not dependent on the LOS outer core and (c) removal of the inner core PEA residues by de-phosphorylation abolished antibody binding. It was also demonstrated (Example 3) that the LOS specific antibodies described in Example 2 were bactericidal and opsonophagocytic against encapsulated *N. meningitidis* clinical isolates.

To further elucidate the antibody specificities described in Examples 2-4, the LOS molecules from the *N. meningitidis* strains set forth in Example 1 (which included the twelve presently known LOS immunotypes) were structurally characterized (Examples 5 and 6A-6E). The results presented in Examples 5, 6A and 6E describe the identification of a novel di-PEA epitope (e.g., see structural formula II below) and a novel di-PEA epitope group thereof (e.g., see Table 1, PEA epitope group II), wherein the novel PEA epitope group is comprised of a co-mixture of di-PEA residues (e.g., see structural formulae I and II below). For example, it was observed that certain *N. meningitidis* strains (e.g., strains expressing immunotypes L1, L3 (strain 6275), L9, L11, L12, strain A1 (L8)) synthesized at least two distinct LOS molecules having different inner core portions, wherein the inner core comprised either (i) a HepII residue comprising an O-3 linked PEA and an O-6 linked PEA (structure I below) or (ii) a HepII residue comprising an O-3 linked PEA and an O-7 linked PEA (structure II below). Thus, it was observed in these experiments that LOS molecules from *N. meningitidis* strains expressing PEA epitope group II comprise a novel co-mixture of PEA-3-HepII-6-PEA (approximately 40%) and PEA-3-HepII-7-PEA (approximately 60%).

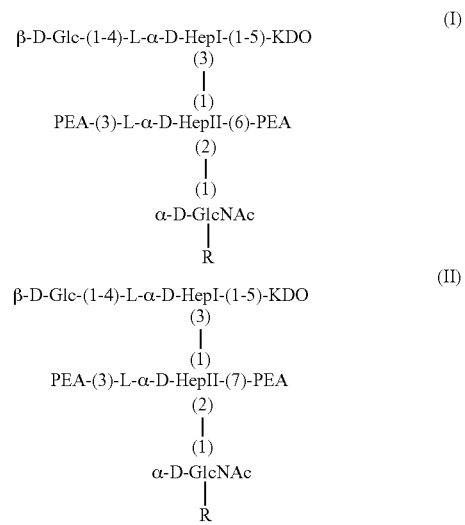

In structures I and II above, Glc is D-glucopyranose, KDO is 2-keto-3-deoxyoctonate, Hep is L-glycero-D-manno-heptose, GlcNAc is N-acetylglucosamine and R is O-Acetyl or H.

In addition to the novel di-PEA epitope identified in the present invention (structure II above), LOS inner core structures lacking PEA (Table 1, PEA epitope group V) and inner core structures with a single PEA unit attached at either position 3, 6 or 7 of the HepII residue have been described previously (Table 1, PEA epitope groups I, III and IV). The substitution of the HepII residue with di-PEA at positions 3 and 6 (PEA-3-HepII-6-PEA) was previously identified in LOS molecules from *N. meningitidis* NMB (i.e., a rfaK mutant strain of NMB, termed CMK1) (Rahman et al., 2001) and *N. meningitidis* galE mutant strain BZ157 (Cox et al., 2002[b]). However, as described above, it was surprisingly observed in the present invention that LOS molecules from certain *N. meningitidis* strains (e.g., strains expressing immunotypes L3 (e.g., strain 6276, strain L3 galE), L8 (e.g., strain A1), L9 (e.g., strain 120M), L11 (e.g., strain 7889) and L12 (e.g., strain 7897)) comprise a novel co-mixture of PEA-3-HepII-6-PEA and PEA-3-HepII-7-PEA LOS inner core structures (i.e., PEA epitope group II).

Thus, in certain embodiments of the invention, it is contemplated that a multivalent immunogenic composition for inducing an immune response against *N. meningitidis* LOS immunotypes L1-L12 will comprise at least the five PEA epitope groups set forth below in Table 1. It should be noted that PEA epitope group V, as designated below and throughout the specification, lacks a PEA substitution at the HepII residue.

TABLE 1

*N. MENINGITIDIS* INNER CORE PEA GROUPS

| PEA Attachment to HepII | PEA Epitope Group |
|---|---|
| PEA-3-HepII | I |
| PEA-3-HepII-6-PEA<br>PEA-3-HepII-7-PEA | II |
| HepII-6-PEA | III |
| Glc-3-HepII-7-PEA | IV |
| Glc-3-HepII-6-PEA | |
| Glc-3-HepII | V |

The *N. meningitidis* strains studied in the present invention, their corresponding LOS immunotype (if known) and the PEA epitope group(s) identified within the LOS molecules of a particular strain, are listed below in Table 2. As indicated in columns two and three of Table 2, a multivalent immunogenic composition for inducing a broad (e.g., cross-reactive) immune response against the twelve LOS immunotypes should comprise structurally distinct PEA epitope groups (e.g., two or more of PEA epitope groups I-V).

TABLE 2

Distribution of Inner Core PEA Epitope Groups Among *N. meningitidis* Strains

| *N. meningitidis* Strain | *N. meningitidis* Immunotype | PEA Epitope Group |
|---|---|---|
| 126E | L1 | I, II |
| NMB | L2 | IV, V |
| 6275 | L3 | II |
| 89I | L4 | III |
| M98I | L5 | V |
| M992 | L6 | III |
| 6155 | L7 | I |
| M978 | L8 | I |
| 120M | L9 | II |
| 7880 | L10 | I |
| 7889 | L11 | II |
| 7897 | L12 | II |
| H355 | | I |
| 2996 | | I |
| H44/76 | L3 | I |
| A1 | L8 | II |
| 7036-6275 (L3 galE) | | II |
| 7350-H44/76 (H44/76 galE) | | I |
| 7350-89I (L4 galE) | | III |
| 7350-NMB (NMB galE) | | IV, V |

The data described in Example 9 of the invention confirmed that a tetravalent LOS-$CRM_{197}$ conjugate (i.e., comprising LOS inner core epitopes representing the five PEA epitope groups) induced rabbit antisera that reacted with LOS from all twelve of the LOS immunotypes, wherein the LOS in the LOS-$CRM_{197}$ conjugate comprised a NMB strain LOS inner core (immunotype L2, PEA epitope groups IV and V), a L4 strain LOS inner core (PEA epitope group III), a H44/76 strain LOS inner core (immunotype L3, PEA epitope group I) and a L11 strain LOS inner core (PEA epitope group II) (FIG. 9). It was also observed that rabbit antisera, generated by immunization with a tetravalent LOS conjugate, was bactericidal (Example 8, Table 13) and opsonophagocytic (Example 8) against wild-type *N. meningitidis* strain H44/76.

Thus, in certain embodiments of the invention, a multivalent immunogenic composition comprises *N. meningitidis* inner core LOS molecules representing the five PEA epitope groups depicted in structural formulae I-V below:

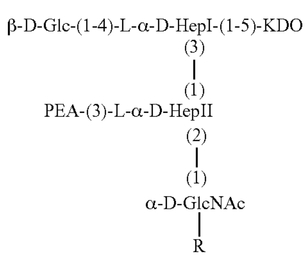

(PEA epitope group I)

-continued 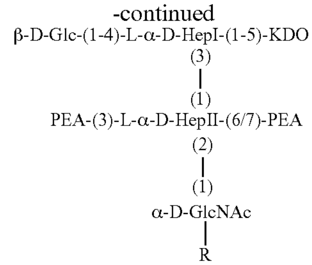 (PEA epitope group II)

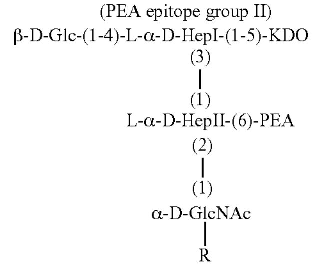

(PEA epitope group III)

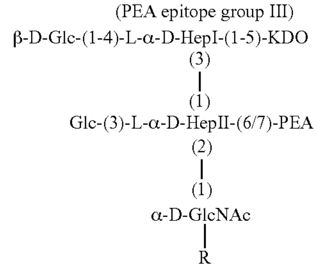

(PEA epitope group IV)

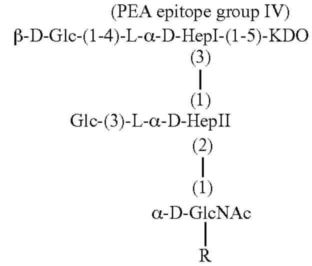

(PEA epitope group V)

In PEA epitope groups I-V above, Glc is D-glucopyranose, KDO is 2-keto-3-deoxyoctonate, Hep is L-glycero-D-manno-heptose, GlcNAc is N-acetylglucosamine and R is O-Acetyl or H. The designation "(6/7)-PEA" above indicates that the PEA is attached at either the O-6 or O-7 position of the HepII residue. In certain embodiments, PEA epitope groups I-V further comprise a glycine residue and/or a phosphocholine residue attached to the HepI residue.

C. *Neisseria Meningitidis* Mutant Strains

In certain embodiments, the invention is directed to LOS molecules isolated from a *N. meningitidis* strain having a mutation in one in one or more genes involved in LOS biosynthesis. For example, the synthesis of *N. meningitidis* LOS requires specific enzymes which perform lipid-A core synthesis, sugar biosynthesis and sugar transfer.

*N. meningitidis* enzymes involved in sugar biosynthesis and transfer include the UDP-galactose epimerase gene (galE), which is essential for the incorporation of galactose into LOS (Jennings et al., 1993); the phosphoglucomutase gene (pgm), which converts glucose 6-phosphate to glucose 1-phoshphate (Zhou et al., 1994$^a$); the rfaD gene (Drazek et al., 1995), which epimerizes ADP-heptose to L-glycero-D-mannoheptose; the heptosyltransferase gene rfaC (Zhou et al., 1994$^b$), which attaches HepI to KDO; the heptosyltransferase gene rfaF (Sandlin et al., 194), which attaches HepI to HepII; the α1,2 N-acetylglucosamine transferase gene rafK (Kahler et al., 1996$^a$), which adds N-acetylglucosamine to HepII and the UDP-glucose: LOS-β-1,4-glucosyltransferase gene IgtF (Kahler et al., 1996$^b$), which attaches the first glucose residue to HepI. A cluster of five sugar transferase genes (IgtA-IgtE) capable of synthesizing the lacto-N-neotetraose group have also been described (Gotschlich, 1994).

Thus, in certain embodiments of the invention, a sugar biosynthesis gene and/or a sugar transfer gene of a wild-type N. meningitidis strain is mutated, wherein the mutation abolishes the enzymatic activity of the encoded protein. In particular embodiments, a mutant N. meningitidis strain of the invention comprises a mutation in a galE gene, a pgm gene, a rfaK gene and/or an IgtF gene, such that the LOS molecules produced in these mutant strains have a truncated LOS outer core or the LOS outer core is absent.

In one particular embodiment, one or more LOS inner core molecules are isolated from a N. meningitidis strain comprising a mutation in its galE gene. As stated above, the UDP-galactose epimerase (encoded by the galE gene) is essential for the incorporation of galactose (Gal) into N. meningitidis LOS molecules (Jennings et al., 1993). It is therefore known to one of skill in the art, that mutations in the galE gene result in N. meningitidis expressing truncated LOS molecules (e.g., lacking an outer core portion). Thus, in certain embodiments of the invention, one or more LOS inner core molecules are isolated from a N. meningitidis galE mutant.

In other embodiments, one or more LOS inner core molecules are isolated from a N. meningitidis strain comprising a mutation in its pgm gene. It is know to one of skill in the art, that a mutated phosphoglucomutase prevents the formation of UDP-galactose and/or UDP-glucose as substrates for incorporation into LOS (Zhou et al., 1994$^a$), thereby resulting in LOS molecules completely lacking an OS outer core portion. Thus, in certain embodiments of the invention, one or more LOS inner core molecules are isolated from a N. meningitidis pgm mutant strain.

In certain other embodiments, one or more LOS inner core molecules are isolated from a N. meningitidis strain comprising a mutation in its rfaK gene. It is know in the art that a mutated α1,2 N-acetylglucosamine transferase results in LOS molecules deficient in the addition of α-chain sugars to HepI and the attachment of N-acetylglucosamine and glucose to HepII (Kahler et al., 1996$^a$), thereby resulting in truncated LOS molecules. Thus, in certain embodiments of the invention, one or more LOS inner core molecules are isolated from a N. meningitidis rfaK mutant strain.

N. meningitidis mutant strains (e.g., a galE mutant) can be generated, for example, from a wild-type strain by insertional inactivation of the gene (e.g., the galE gene) with a kanamycin expression cassette as a selectable marker.

In other embodiments, one or more LOS inner core molecules are isolated from a N. meningitidis strain comprising a mutation in two or more genes selected from the group consisting of galE, pgm and rfaK. In another embodiment, one or more LOS inner core molecules are isolated from a N. meningitidis strain comprising a mutation in each of the galE, pgm and rfaK genes.

D. *Neisseria Meningitidis* LOS Conjugates

In certain embodiments, one or more LOS inner core molecules of the invention are conjugated to a carrier protein. Carrier proteins are known to one of skill in the art, and include, but are not limited to, proteins such as tetanus toxin, a diphtheria toxin, a mutant diphtheria toxin, a CRM$_{197}$ protein, a pseudomonas exotoxin A protein, a cholera toxin (CT) protein, a cholera toxin mutant CT-E29H protein, a Group A streptococcal toxin protein, a *Streptococcus pneumoniae* pneumolysin protein, a filamentous haemagglutinin (FHA) protein, a *Bordetella pertussis* FHA fragment protein, a *N. gonorrheae* pilin protein, a *N. meningitidis* pilin protein, a *N. gonorrheae* outer membrane protein, a *N. meningitidis* ORF 2086 protein, a *Streptococcus* C5a peptidase and a staphylococcal MSCRAMM protein.

In one particular embodiment, one or more LOS molecules of the invention are conjugated to a CRM$_{197}$ protein (e.g., see U.S. Pat. No. 5,614,382, incorporated herein by reference). In other embodiments, one or more LOS inner core molecules of the invention are conjugated to a *N. meningitidis* protein encoded by a nucleic acid sequence open reading frame (ORF) identified as "ORF 2086" (e.g., see International Publication No. WO 03/063766 A2 (International Application No. PCT/US02/32369), U.S. Provisional Application No. 60/463,161 and International Publication No. WO 04/065603 A2 (International Application No. PCT/US04/000800), each specifically incorporated herein by reference). In certain other embodiments, one or more LOS inner core molecules of the invention are conjugated to a *Streptococcus* C5a peptidase (e.g., see U.S. Pat. No. 6,355,255, U.S. Pat. No. 6,270,775; and U.S. Pat. No. 5,846,547, each incorporated herein by reference).

Methods for conjugating LOS and/or OS molecules to a carrier protein are well known to one of skill in the art (e.g., see Example 1). Described below in Example 10, is an analysis of the immunogenicity of *N. meningitidis* LOS conjugated to CRM$_{197}$ through the carboxylate of a KDO residue versus the immunogenicity of *N. meningitidis* LOS conjugated to CRM$_{197}$ through the amine of PEA residue. The data from this study indicate that conjugation of LOS molecules via PEA significantly attenuates or abolishes LOS inner core antigenicity, whereas conjugation of LOS via KDO maintains LOS inner core antigenicity. Thus, in certain embodiments, one or more LOS inner core molecules of the invention are conjugated through the carboxylic acid of an inner core KDO.

E. Immunogenic and Pharmaceutical Compositions

In certain embodiments, the invention is directed to immunogenic compositions comprising one or more N. meningitidis LOS inner molecules set forth above. In another embodiment, an immunogenic composition comprises N. meningitidis LOS inner molecules comprising the following structures:

β-D-Glc-(1-4)-L-α-D-HepI-(1-5)-KDO
(3)
|
(1)
PEA-(3)-L-α-D-HepII-(6)-PEA
(2)
|
(1)
α-D-GlcNAc
|
R

-continued

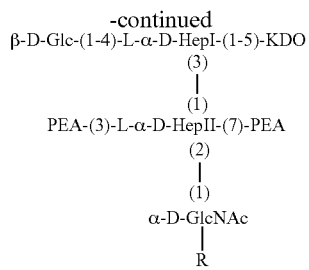

In certain other embodiments, an immunogenic composition comprises at least five *N. meningitidis* LOS inner core molecules representing PEA epitope groups I-V in Table 1. In other embodiments, the LOS molecules are conjugated to a carrier protein, as described above in Section D and Examples 1 and 10.

In yet other embodiments, an immunogenic composition of the invention further comprises one or more additional *N. meningitidis* antigens and/or one or more additional antigens from other bacterial species. In certain embodiments, one or more *N. meningitidis* LOS inner core molecules of the invention are combined (e.g., as conjugates or a liposome formulations) with one or more *N. meningitidis* polypeptides, polypeptide fragments, carbohydrates, oligosaccharides, lipids, lipooligosaccharides, polysaccharides, oligosaccharide-protein conjugates, polysaccharide-protein conjugates, peptide-protein conjugates, oligosaccharide-peptide conjugates, polysaccharide-peptide conjugates, protein-protein conjugates, lipooligosaccharide-protein conjugates or polysaccharide-protein conjugates.

In certain embodiments, one of the one or more additional *N. meningitidis* antigens is a *N. meningitidis* protein encoded by a nucleic acid sequence ORF identified as "ORF 2086" (e.g., see International Publication No. WO 03/063766 A2 (International Application No. PCT/US02/32369), U.S. Provisional Application No. 60/463,161 and International Publication No. WO 04/065603 A2 (International Application No. PCT/US04/000800), each specifically incorporated herein by reference). In one particular embodiment, an immunogenic composition comprising one or more *N. meningitidis* LOS inner molecules of the invention further comprises one or more *N. meningitidis* ORF 2086 proteins.

An immunogenic composition of the invention is formulated such that it is suitable for administration to a mammalian subject, e.g., a human. Such compositions typically comprise the "immunogenic" composition (e.g., one or more LOS inner core molecules) and a "pharmaceutically acceptable carrier". As used hereinafter the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media are used in the compositions of the invention. Supplementary active compounds are also incorporated into the compositions.

An immunogenic composition of the invention is formulated to be compatible with its intended route of administration. Examples of routes of administration include parenteral (e.g., intravenous, intradermal, subcutaneous, intramuscular, intraperitoneal), mucosal (e.g., oral, rectal, intranasal, buccal, vaginal, respiratory) and transdermal (topical). Solutions or suspensions used for parenteral, intradermal, or subcutaneous application include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH is adjusted with acids or bases, such as hydrochloric acid or sodium hydroxide. The parenteral preparation is enclosed in ampoules, disposable syringes or multiple dose vials made of glass or plastic.

Sterile injectable solutions are prepared by incorporating the active compound (e.g., an LOS inner core molecule, a conjugate thereof or a liposome thereof) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

For administration by inhalation, the immunogenic compositions are delivered in the form of an aerosol spray from pressured container or dispenser which contains a suitable propellant, e.g., a gas such as carbon dioxide, or a nebulizer. Systemic administration is also by mucosal or transdermal means. For mucosal or transdermal administration, penetrants appropriate to the barrier to be permeated are used in the formulation. Such penetrants are generally known in the art, and include, for example, for mucosal administration, detergents, bile salts, and fusidic acid derivatives. Mucosal administration is accomplished through the use of nasal sprays or suppositories. For transdermal administration, the active compounds are formulated into ointments, salves, gels, or creams as generally known in the art.

Liposomal suspensions are also used as pharmaceutically acceptable carriers. These are prepared according to methods known to those skilled in the art, for example, as described in U.S. Pat. No. 4,522,811 which is incorporated hereinafter by reference.

It is often advantageous to formulate parenteral compositions in dosage unit form for ease of administration and uniformity of dosage. Dosage unit form as used hereinafter refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The immunogenic compositions of the invention may further comprise one or more adjuvants. An "adjuvant" is a substance that serves to enhance the immunogenicity of an antigen. Thus, adjuvants are often given to boost the immune response and are well known to the skilled artisan. Examples of adjuvants contemplated in the present invention include, but are not limited to, aluminum salts (alum) such as aluminum phosphate and aluminum hydroxide, *Mycobacterium*

*tuberculosis, Bordetella pertussis*, bacterial lipopolysaccharides, aminoalkyl glucosamine phosphate compounds (AGP), or derivatives or analogs thereof, which are available from Corixa (Hamilton, Mont.), and which are described in U.S. Pat. No. 6,113,918; one such AGP is 2-[(R)-3-Tetradecanoyloxytetradecanoylamino]ethyl 2-Deoxy-4-O-phosphono-3-O-[(R)-3-tetradecanoyoxytetradecanoyl]-2-[(R)-3-tetradecanoyoxytetradecanoylamino]-b-D-glucopyranoside, which is also known as 529 (formerly known as RC529), which is formulated as an aqueous form or as a stable emulsion, MPL™ (3-O-deacylated monophosphoryl lipid A) (Corixa) described in U.S. Pat. No. 4,912,094, synthetic polynucleotides such as oligonucleotides containing a CpG motif (U.S. Pat. No. 6,207,646), polypeptides, saponins such as Quil A or STIMULON™ QS-21 (Antigenics, Framingham, Mass.), described in U.S. Pat. No. 5,057,540, a pertussis toxin (PT), or an *E. coli* heat-labile toxin (LT), particularly LT-K63, LT-R72, CT-S109, PT-K9/G129; see, e.g., International Patent Publication Nos. WO 93/13302 and WO 92/19265, cholera toxin (either in a wild-type or mutant form, e.g., wherein the glutamic acid at amino acid position 29 is replaced by another amino acid, preferably a histidine, in accordance with published International Patent Application number WO 00/18434). Similar cholera toxin mutants are described in published International Patent Application number WO 02/098368 (wherein the isoleucine at amino acid position 16 is replaced by another amino acid, either alone or in combination with the replacement of the serine at amino acid position 68 by another amino acid; and/or wherein the valine at amino acid position 72 is replaced by another amino acid). Other cholera toxin mutants are described in published International Patent Application number WO 02/098369 (wherein the arginine at amino acid position 25 is replaced by another amino acid; and/or an amino acid is inserted at amino acid position 49; and/or two amino acids are inserted at amino acid positions 35 and 36).

Various cytokines and lymphokines are suitable for use as adjuvants. One such adjuvant is granulocyte-macrophage colony stimulating factor (GM-CSF), which has a nucleotide sequence as described in U.S. Pat. No. 5,078,996. A plasmid containing GM-CSF cDNA has been transformed into *E. coli* and has been deposited with the American Type Culture Collection (ATCC), 1081 University Boulevard, Manassas, Va. 20110-2209, under Accession Number 39900. The cytokine Interleukin-12 (IL-12) is another adjuvant which is described in U.S. Pat. No. 5,723,127. Other cytokines or lymphokines have been shown to have immune modulating activity, including, but not limited to, the interleukins 1-α, 1-β, 2, 4, 5, 6, 7, 8, 10, 13, 14, 15, 16, 17 and 18, the interferons-α, β and γ, granulocyte colony stimulating factor, and the tumor necrosis factors α and β, and are suitable for use as adjuvants.

A composition of the present invention is typically administered parenterally in dosage unit formulations containing standard, well-known nontoxic physiologically acceptable carriers, adjuvants, and vehicles as desired. The term parenteral as used hereinafter includes intravenous, subcutaneous, intradermal, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation are also a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil is employed including synthetic mono- or di-glycerides. In addition, fatty acids such as oleic acid find use in the preparation of injectables.

Carriers include neutral saline solutions buffered with phosphate, lactate, Tris, and the like. When administering viral vectors, the vector is purified sufficiently to render it essentially free of undesirable contaminants, such as defective interfering adenovirus particles or endotoxins and other pyrogens, so that it does not cause any untoward reactions in the individual receiving the vector construct. A preferred means of purifying the vector involves the use of buoyant density gradients, such as cesium chloride gradient centrifugation.

F. EXAMPLES

The following examples are carried out using standard techniques, which are well known and routine to those of skill in the art, except where otherwise described in detail.

Example 1

Materials and Methods

*Neisseria meningitidis* Strains. *N. meningitidis* strains H44/76, A1, H355, NMB and SS3 have been described previously (Mandrell and Zollinger, 1977; Gu et al., 1992; Holten, 1979; Zollinger and Mandrell 1983; Kim et al., 1988; Virji et al., 1991). *N. meningitidis* strains 126E (immunotype L1), 35 E (immunotype L2), 6275 (immunotype L3), 89I (immunotype L4), M981 (immunotype L5), M992 (immunotype L6), 6155 (immunotype L7), M968 (immunotype L8), 120M (immunotype L9), 7880 (immunotype L10), 7889 (immunotype L11) and 7897 (immunotype L12) have been described previously (Mandrell and Zollinger, 1977; Zollinger and Mandrell, 1980) and were provided by W. D. Zollinger (Walter Reed Army Med. Ctr., Washington, D.C.).

The *N. meningitidis* mutants 7350-H44/76, 7350-NMB, 7350-89I and 7036-6275 were generated from wild-type strains by insertional inactivation of the capsule and galE genes with either a kanamycin or erythromycin expression cassette as a selectable marker.

*Neisseria meningitidis* Growth and Lipo-Oligosaccharide (LOS) Purification. *N. meningitidis* strains were grown in 8.5 L of Morse's medium in a fermentor. The following parameters were controlled: Temperature=36° C.; pH=7.4; dissolved $O_2$=20%. The culture was grown to an optical density ($OD_{600\,nm}$) of 4 to 6 and heat killed (65° C., 1 hour). The LOS was extracted from the cells by hot phenol-water extraction as described previously (Wu et al., 1987; Gu et al., 1995) with some modifications. Cell pellets were suspended in 40 mM phosphate buffer containing 5 mM EDTA and 0.02% sodium azide and digested with lysozyme (2 mg/ml) for 16-18 hours at 4° C., followed by incubation (37° C.) with nucleases (100 μg/ml) for 3 hours. Crude LOS was isolated by hot phenol-water extraction (Westphal and Jann, 1965). The LOS was precipitated from the aqueous phase with sodium acetate (5 mg/ml) and two volumes of acetone at 4° C. overnight. The pellet was washed with 70% ethanol to remove traces of phenol and retreated with nucleases as described above followed by proteinase K treatment (0.35 mg/ml) at 60° C. for 16-18 hours. After three ultra centrifugations (105,000 g) for 3 hours at 5° C., the purified LOS was solubilized in sterile water and lyophilized. The purified LOS contained less than 1% protein contaminations as determined by Pierce's BCA Protein Assay (Smith et al., 1985) and amino acid analysis. The purified LOS contained less than 1% nucleic acid contaminations as determined by UV absorption at 260 nm (Wu et al., 1987).

Preparation of de-O-acylated LOS for structural analysis. LOS (10 mg) was de-O-acylated (dLOS) using 1 ml of anhydrous hydrazine for 3 hours at 37° C. (Helander et al., 1988). The suspension was cooled and added drop wise to 5 ml of cold acetone. Precipitated dLOS was separated by centrifugation and the resulting pellet was dissolved in water, and further purified by size-exclusion chromatography (SEC) on a Bio-Gel P6 column (Bio-Rad Laboratories, Inc.; Hercules, Calif.). The presence of dLOS in the collected fractions was monitored by testing for 2-keto-3-deoxyoctonate (KDO) (Waravdekar and Saslaw, 1959).

Preparation of de-O-acylated LOS for conjugate synthesis. Lipo-oligosaccharides from strains N. meningitidis 7350-H44/76, 7350-NMB and 7350-89I were treated with 100 mM NaOH at 60° C. for 20 minutes. N. meningitidis strain 7036-6275 LOS (10 mg) was treated with 45 mM NaOH at 80° C. for 20 minutes. The reaction mixtures were cooled down to room temperature on an ice bath and neutralized with 0.1 M HCl. The de-O-acylated LOS (dLOS) was purified by SEC on Bio-Gel P6 column (Bio-Rad Laboratories, Inc; Hercules, Calif.). The presence of dLOS in the collected fractions was monitored by testing for 2-keto-3-deoxyoctonate (KDO) (Waravdekar and Saslaw, 1959).

Core Oligosaccharide (OS) Preparation. Core OS was released from the lipid-A component by mild acid hydrolysis with 1% acetic acid at 100° C. for 3 hours, and insoluble lipid-A was removed by centrifugation. The supernatant was lyophilized and the OS was further purified by SEC on a Bio-Gel P6 column using water as eluent or Bio-Gel P4 column using 0.05 M pyridinium acetate buffer (pH 5.23) as eluent. The collected fractions containing core OS were lyophilized.

Dephosphorylation of LOS and Core OS. Dephosphorylated LOS and dephosphorylated core OS were prepared by treating with 48% HF for 48 hours (Yamasaki et al., 1988).

SDS-polyacrylamide Gel Electrophoresis (SDS-PAGE) and Western Blot Analysis. LOS SDS-PAGE was carried out on a 4-20% polyacrylamide gel (Bio-Rad; Hercules, Calif.) at 150 V for 1 hour and visualized by silver staining as described by Morrissey (Morrissey, 1981). The LOS was transferred from the polyacrylamide gel to nitrocellulose membranes at 100 V for 45 minutes. The nitrocellulose membranes were blocked with 3% BSA in PBS for 30 minutes. Sera and monoclonal antibodies, diluted (1:100) in blocking buffer, were incubated at room temperature for 1-2 hours. Membranes were washed three times with PBS/Tween$^{20}$ (0.05%) and alkaline phosphatase, and conjugated antibodies specific to mouse or rabbit IgG at dilution (1:250) were incubated for 30 minutes at room temperature. Membranes were washed with three times with PBS/Tween$^{20}$ (0.05%) and binding of LOS antibodies was visualized using Alkaline Phosphatase Substrate Kit (Bio-Rad Laboratories, Inc.; Hercules, Calif.).

Sugar Composition Analysis and Linkage Site Analysis. Sugar composition analysis was performed by the alditol acetate method (Sawardeker et al., 1967). The hydrolysis was done in 2 M trifluoroacetic acid at 121° C. for 3 hours, followed by reduction in $H_2O$ with $NaBD_4$ and subsequent acetylation with acetic anhydride, with residual sodium acetate as the catalyst. Alditol acetate derivatives were analyzed by gas-liquid chromatography (GC) mass spectrometry (MS) using a Varian chromatograph (Varian, Inc.; Walnut Creek, Calif.) equipped with a 30-m DB-5 capillary column (Agilent Technologies and J & W Scientific; Wilmington, Del.) (210° C. for 30 minutes, then ramped to 240° C. at 2° C./minute), and the mass spectra in the electron impact mode were recorded using a Varian Saturn II mass spectrometer (Varian, Inc.; Walnut Creek, Calif.). Enantiomeric configurations of the individual sugars were determined by the formation of the respective 2-(S)— and 2-(R)-butyl chiral glycosides (Leontein et al., 1978). Methylation linkage analysis was carried out by the $NaOH/Me_2SO/CH_3I$ procedure (Ciucanu and Kerek, 1984) and with characterization of permethylated alditol acetate derivatives by gas-liquid chromatography mass spectrometry in the electron impact mode (DB-5 column, isothermally at 190 C for 60 minutes).

Mass Spectrometry (MS) and Nuclear Magnetic Resonance (NMR) Spectroscopy. The electrospray ionization mass spectrometry (ESI-MS) experiments were carried out on a Thermo Finnigan LCQ Deaxp instrument. An electrospray stainless steel needle (27 gauge) was butted against the low dead volume "T" and enabled the delivery of the sheath solution to the end of the capillary column. The separations were obtained on a bare fused-silica capillary column (approximately 90-cm length) in deionized water. A voltage of 20 kV was typically applied at the injection. Mass spectra were acquired with dwell times of 3.0 milliseconds per step of 1 m/z unit in full-mass scan mode.

Matrix-assisted laser desorption ionization time-of-flight mass spectrometry (MALDI-TOF-MS) of OS and dLOS samples were performed on a Voyager-DE STR MALDI-TOF instrument (Applied Biosystems, Inc; Foster City, Calif.) equipped with a nitrogen laser (337 nM). All spectra were recorded in the negative and positive ion mode using delayed extraction conditions, with an accelerating voltage of 20 KV. A one µL portion of each dialyzed sample was delivered into a 0.5 mL microcentrifuge tube containing a few beads of Dowex 50W-X8 resin (100-200 mesh, $H^+$ form; Bio-Rad Laboratories; Hercules, Calif.) and allowed to sit for about one minute. One µL of the matrix solution (a saturated solution of 2,5-dihydroxybenzoic acid in acetone) was then added to the sample and mixed briefly. Finally, the samples were spotted on a stainless steel MALDI target and allowed to air-dry. Approximately 100 laser shots were recorded for each sample. The resulting spectra were analyzed with Gaussian-smoothed and baseline-corrected by DataExplorer (Applied Biosystems, Inc.; Foster City, Calif.).

Tandem mass spectrometry experiments (MS/MS) were performed at a pressure of 15 p.s.i. with argon as the collision gas to produce fragment ions (Hunt et. al. 1989 and Covey et. al. 1991). The later fragment ion was subjected to an additional stage of MS/MS analysis using a nozzle-skimmer MS/MS technique (Loo et. al., 1990; Loo et. al., 1991).

$^1$H and $^{31}$P NMR spectra of core OS was obtained on a Bruker AMX 500 spectrometer at 300 K using standard Bruker software. Prior to performing the NMR experiments, the samples were lyophilized three times with $D_2O$ (99.9%). The HOD peak was used as the internal reference at $\delta_H$ 4.786.

Conjugation of LOS to Carrier Protein $CRM_{197}$. N. meningitidis dLOS was conjugated to the $CRM_{197}$ protein (U.S. Pat. No. 5,614,382, incorporated herein by reference) via the linker molecule 3-(2-pyridyldithio)-propionyl hydrazide (PDPH) (Pierce, Rockford, Ill.) as follows: the dLOS (5 mg/mL in water) was thiolated with 3(2-pyridyidithio)-propionyl hydrazide (PDPH) (Pierce, Rockford, Ill.) by reaction of carbodiimide activated carboxylate groups of the dLOS KDO residues with the hydrazide group of PDPH at pH 4.9. Adjusting the pH to 7.4 stopped the reaction and the dLOS-PDPH was purified by dialysis (Pierce Slide-A-Lyzer 10K) three times against 500 mL of sterile water. The dLOS-PDPH was reduced with 200 mM dithiothreitol (DTT) and the dLOS was purified by gel filtration on Bio-Gel P6 column using 0.1 M NaHCO3/1 mM EDTA (pH 8.0) as eluent. The degree of thiolation was determined by thiol assay using 2,2-Dithiodipyridine (DTDP, Sigma-Aldrich Corporation; St. Louis, Mo.,) (Grassetti et. al., 1967). The amine groups of the lysine residues of the $CRM_{197}$ protein were activated with N-hydroxysuccimide ester of bromoacetic acid according to the procedure described by Bernatowicz and Matsueda (1986). Bromoacetylated $CRM_{197}$ was mixed with dLOS to achieve a final ratio of 1:1 (w/w). The pH was adjusted to 9.2 with 1 M carbonate buffer and the reaction mixture was incubated overnight at 4° C. The unreacted bromoacetyl groups were blocked with N-Acetyl cysteamine and incubated for 3 hours at room temperature. The LOS-$CRM_{197}$ conjugate (i.e., dLOS-PDPH-$CRM_{197}$) was purified by dialysis against three exchanges of PBS (pH 7.4, 1000 mL) and characterized by SDS-PAGE and Western Blot.

*Neisseria meningitidis* LOS Specific Monoclonal and Polyclonal Antibodies. Monoclonal antibodies were generated by immunization of BALB/c mice two to three times with a crude outer membrane preparation from group B *N. meningitidis* strains 2996 and NMB. The animals were tested one month before an intraperitoneal (i.p.) boost, three days prior to cell fusion. Splenocytes were harvested and fused with non-secreting X63Ag8.653 mouse (BALB/c) myeloma cells according to standard methodology (Kohler and Milstein, 1975; Kohler and Milstein, 1976). After approximately two weeks, supernatant media from resultant hybridoma cultures were screened for activity and specificity by EIA against a variety of purified LOS immunotype preparations and formalin fixed meningococcal cells. Selected parent cultures were propagated, cryopreserved, subcloned, and expanded for antibody production.

Polyclonal antibodies were generated by subcutaneous immunization of Swiss Webster mice with 10 µg of *N. meningitidis* L4 and L5 LOS, adjuvanted with 20 µg QS-21 three times at 2-week intervals. Sera collected at week eight were tested for specific L4 and L5 LOS antibody titers in LOS ELISA.

LOS ELISA. Microtiter plates (Greiner, Omega Scientific; Tarzana, Calif.) were pre-coated with 100 µl/well poly-L-lysine (5 µg/ml in PBS), incubated for sixty minutes at 37° C. and washed three times with PBS, 0.1% Tween[20]. The microtiter plates were coated with 100 µl/well of LOS (5 µg/ml in PBS) and incubated overnight at 37° C. The plates were blocked with PBS, 0.1% Tween[20], 5% FBS (±0.02% azide). Sera and monoclonal antibodies, diluted in blocking buffer, were added (100 µl/well) and incubated for two hours at 37° C. Plates were washed three times with PBS, 0.1% Tween[20] and alkaline phosphatase. Conjugated goat antibodies specific to mouse or rabbit IgG at dilution 1:2000 or 1:4000 were incubated for 60 minutes at 37° C. Para nitrophenyl phosphate (p-NPP) in diethanolamine (KPL, Inc.; Gaithersburg, Md.) was used as the substrate. The color reaction was stopped with 100 µl/well 5% EDTA. The absorbance was measured at 405 nm and endpoint titers calculated at 0.1 OD.

Inhibition ELISA. Monoclonal antibodies or polyclonal antisera were pre-incubated with an LOS inhibitor prior to being added to LOS-coated plates. The plates were then assayed as described above.

Immunization of Rabbits and Mice with the dLOS-PDPH-$CRM_{197}$ Conjugate. Six to eight week old Swiss Webster mice (female; ten per group) were immunized subcutaneously (s.c.) with 10 µg of the dLOS-PDPH-$CRM_{197}$ conjugate, adjuvanted with 20 µg of QS21. The mice were injected on week 0, week 3 and week 6, and sera for analysis was collected at week 8. New Zealand white rabbits were given three subcutaneous injections at week 0, week 3 and week 6 with 20 µg of the dLOS-PDPH-$CRM_{197}$ conjugate, adjuvanted at week 0 with Freund's Complete Adjuvant (CFA) and Freund's Incomplete Adjuvant (IFA) at week 3 and week 6. The sera for analysis were collected at week 9, week 10 and week 11.

Serum Bactericidal Killing Assay. Target cells were removed from the working stock culture and diluted immediately prior to addition into reaction mixtures. Assay mixtures (50 µl per well) containing target cells (10 µl), test serum (5 µl neat or diluted) and PCM (25 µl), followed by the addition of 10 µl of complement (lacking significant bactericidal activity) were incubated at 36° C. with 5% $CO_2$ for 30 minutes after slight agitation.

After incubation assay reactions were terminated by adding 200 µl of PCM. Aliquots (50 µl) from the PCM diluted reaction wells were plated onto solid GCK agar media and incubated at 36° C. with 5% $CO_2$ for at least 18 hours. Titers for the assays were expressed as the reciprocal of the lowest dilution of test serum that kills ≧50% of the target cells introduced into the assays ($BC_{50}$ titer). Bactericidal activity of test serum was calculated as a percentage of colony forming *N. meningitidis* recovered from assay mixtures compared to the number of colonies isolated from reaction wells that either (i) did not contain antibody or (ii) contained normal serum lacking bactericidal activity. Fluorescence-based serum bactericidal assay was performed as described by Mountzouros et al. (Mountzouros and Howell, 2000).

Chemiluminescence Opsonophagocytic Assay. Polymorphonuclear cells (PMNs) were purified from heparinized venous blood freshly drawn from four individuals. The assay reagents were assembled in a 96-well round bottom plate. The reagents consisted of 20 µl Hanks balanced salt solution (HBSS) containing calcium and magnesium (100×), 550 mM glucose, 10% gelatin in HBSS and 0.01% human serum albumin, 2.5 µL of heat-inactivated (56° C. for 30 minutes) serially diluted (three-fold dilutions) mouse or rabbit pre-immune and immune serum sample, 7.5 µL of buffer, 7.5 µL of 1 mM Luminol, and 15 µL of *N. meningitidis* diluted with buffer approximately 4-150 times the PMN concentration depending on the strain of *N. meningitidis* used. This mixture was incubated at 37° C. in 5% $CO_2$ on an orbital shaker at 400 rpm for approximately 15-18-minutes. After incubation 15 µL C8 depleted human complement used neat or diluted depending on the strain of *N. meningitidis*, and 15 µL of PMNs at a concentration of $1.12 \times 10^7$ PMN/mL were added. A serum sample with predetermined opsonophagocytic activity was used as a positive control.

Infant Rat Bacteremia Model. Approximately 18-24 hours prior to challenge, 3 to 4 day old Sprague-Dawley rats (10 rats/group) were injected i.p. with 1:5 dilutions of the non-immune and hyperimmune sera from rabbits immunized with monovalent *N. meningitidis* H44/76 galE dLOS conjugate and *N. meningitidis* tetravalent galE dLOS conjugate. Rats were challenged with approximately $2.1 \times 10^5$ CFU of *N. meningitidis* H44/76 per rat. Three hours after the challenge, rats were bled and sacrificed. Aliquots of blood from a cardiac puncture were plated onto GCK media and incubated for 18 hours at 36° C., 5% $CO_2$. Levels of bacteremia were determined by counting colonies on GCK plates after incubation.

Example 2

Reactivity of *Neisseria meningitidis* Lipo-Oligosaccharide (LOS) Antibodies

Epitopes of *N. meningitidis* LOS were evaluated by testing the reactivity of LOS specific monoclonal and polyclonal antibodies with a collection of *N. meningitidis* LOSs, which included each of the twelve presently know *N. meningitidis* immunotypes L1-L12 (e.g., see Example 1).

Figure 2:
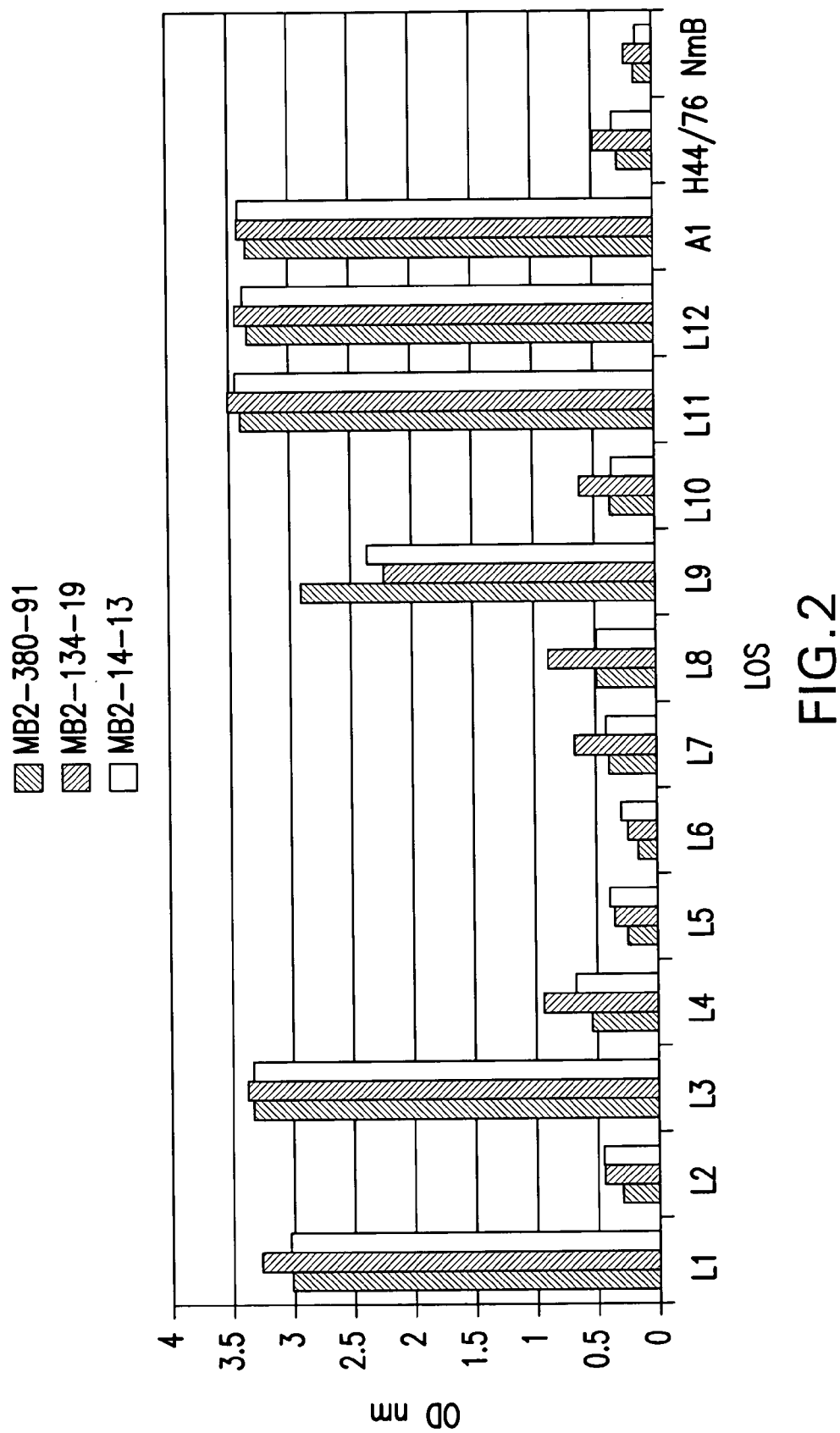
FIG. 2 shows the reactivity of monoclonal antibodies MB2-380-91, MB2-134-19 and MB2-14-13 with a collection of N. meningitidis LOS molecules. The monoclonal antibodies were generated by immunizing mice with a crude outer membrane preparation of N. meningitidis strain 2996 (serogroup B).

Three monoclonal antibodies (MAbs), MB2-380-91, MB2-134-19 and MB2-14-13, were generated by immunizing mice with a crude outer membrane preparation of *N. meningitidis* strain 2996 (serogroup B). All three antibodies demonstrated very similar reactivity patterns with *N. meningitidis* LOSs. MAbs MB2-380-91, MB2-134-19 and MB2-14-13 reacted strongly with L1, L3 (strain 6275), L9, L11, L12 and strain A1 (L8) LOSs (FIG. 2), indicating that immunotypes L1, L3 (6275), L9, L11, L12 and A1 (L8) possess similar LOS epitopes. The reactivity of MAbs MB2-380-91, MB2-134-19 and MB2-14-13 with other LOS immunotypes tested (e.g., L2, L4, L5, L6, L8 (strain M978), L10, strain H44/76 (L3) and NMB (L2)) was minimal (FIG. 2).

Monoclonal antibodies LOS-556-24 and LOS-1345-33, generated by immunizing mice with a crude outer membrane preparation of *N. meningitidis* strain NMB (serogroup B), only reacted with L2 LOS and NMB LOS (data not shown). The other LOS immunotypes tested (e.g., L1, L3-L12, A1 and H44/76) failed to react with MAbs LOS-556-24 and LOS-1345-33. The *N. meningitidis* NMB strain was previously immunotyped as L2, suggesting that MAbs LOS-556-24 and LOS-1345-33 recognize an L2 immunotype specific epitope.

The reactivity of L4 specific mouse polyclonal antibodies revealed that L4 LOS (ELISA titer approximately 12,500) and L6 LOS (ELISA titer approximately 11,000) express similar epitopes. The L5 mouse polyclonal antibody recognized only the L5 immunotype (ELISA titer approximately 28,000).

These data indicate that *N. meningitidis* immunotypes L1, L3 (6275), L9, L11, L12 and A1 (L8) LOS possess a specific epitope that is different from the epitope(s) present on L2 LOS, and that the LOS of L4 and L6 immunotypes share a specific epitope not present in other immunotypes.

These findings point out five different LOS epitopes on *N. meningitidis*:
1. Epitope present at L1, L3 (6275), L9, L11, L12 and A1 (L8) LOS, recognized by MAbs MB2-380-91, MB2-134-19 and MB2-14-13;
2. Epitope present at L2 and NMB LOS, recognized by MAbs LOS-556-24, LOS-1345-33, and LOS 1622;
3. Epitope present at L4 and L6 LOS, recognized by polyclonal L4 LOS rabbit antisera;
4. Epitope present on L7, L8 (M978), H44/76 (L3) and L10 LOS, not recognized by any antibodies tested; and
5. Epitope present at L5 LOS, recognized by polyclonal L5 LOS rabbit antisera.

Example 3

Bactericidal Activity and Opsonophagocytosis Mediated by LOS Specific Monoclonal Antibodies The LOS specific monoclonal antibodies described in Example 2 were evaluated for their protective effect in bactericidal and opsonophagocytic assays against encapsulated *N. meningitidis* clinical isolates. The results demonstrated that MAb MB2-380-91 was bactericidal against *N. meningitidis* strain H355 (serogroup B) (Table 3, 8% viability). The bactericidal activity (or killing) was dependent on MAb MB2-380-91 binding to surface exposed LOS on the encapsulated H355 strain, as confirmed by inhibition of the killing by preincubation of the MAb with de-O-acylated H355 LOS (Table 3, 177% viability). The MAb LOS-1345-33, which recognizes the L2 immunotype, was not bactericidal against *N. meningitidis* strain H355 (Table 3, 290% viability).

TABLE 3

BACTERICIDAL ACTIVITY OF LOS MABS AGAINST *N. MENINGITIDIS* STRAIN H355

| MAbs | Percent Viability of Strain H355 |
| --- | --- |
| MB2 380-91 | 8% |
| MB2 380-91 + H355 dLOS | 177% |
| LOS 1345-33 | 290% |
| LOS 1345-33 + H355 dLOS | 300% |

In addition to bactericidal activity, MAb MB2-380-91 was able to mediate opsonophagocytosis of *N. meningitidis* strain H355 (data not shown). The opsonophagocytosis of strain H355 was inhibited by the addition of de-O-acylated LOS from strain H355 into the reaction mixture (data not shown). The L2 specific MAb 1345-33 could not opsonize the strain H355 (data not shown). MAb LOS-1622, generated by immunization of mice with a crude outer membrane preparation of *N. meningitidis* strain NMB (serogroup B), was able to opsonize encapsulated *N. meningitidis* NMB, whereas the opsonophagocytosis was eliminated by preincubation of MAb LOS-1622 with de-O-acylated *N. meningitidis* NMB LOS (data not shown). These data indicate that antibodies specific for *N. meningitidis* LOS are involved in protection against meningococcal infection and disease.

Example 4

Specificity of Antibodies Against *Neisseria meningitidis* LOS

The difference in LOS immunotypes arises from the variation of core oligosaccharide (OS) structure, in the length of α-chain and in modifications of LOS inner core (e.g., see FIG. 1). The major modifications of the LOS inner core are differences in substitutions of 2-aminoethyl phosphate residues (PEA) and glucose (Glc) on the distal heptose residue (HepII). The importance of LOS O-acylation, phosphorylation and the length of its α-chain in the binding recognition by MAbs was evaluated by inhibition ELISA.

As described in Example 1, LOS was dephosphorylated by treatment with 48% HF and de-O-acylated LOS was prepared by mild hydrazinolysis. Truncated LOS (i.e., LOS lacking the presence of a terminal lacto-N-tetraose in the α-chain) was isolated from a *N. meningitidis* NMB strain galE mutant (designated SS3).

Figure 3:
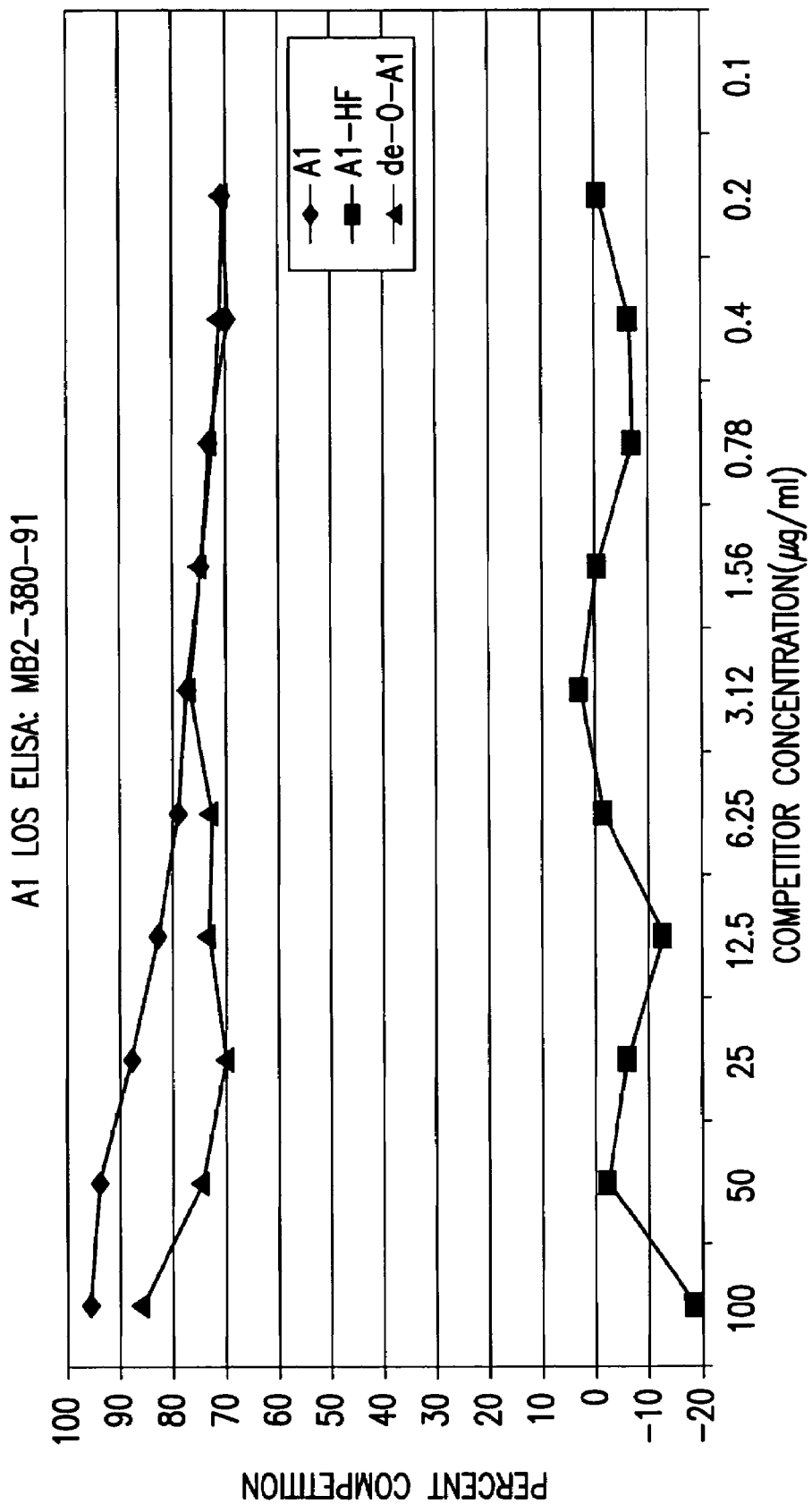
FIG. 3 shows a competition binding assay of MAb MB2-380-91 to wild-type A1 LOS in the presence of increasing competitors de-O-acylated A1 LOS (filled triangles), wild-type A1 LOS (filled diamonds) and dephosphorylated A1 LOS (filled squares).

Data from competition binding assays (FIG. 3) showed that the binding of MAb MB2-380-91 to A1 LOS (i.e., microtiter plates coated with A1 LOS) was inhibited by pre-incubation of MAb MB2-380-91 with wild-type A1 LOS (FIG. 3, filled diamonds). Similarly, the binding of MAb MB2-380-91 to A1 LOS coated microtiter plates was also inhibited by pre-incubation MAb MB2-380-91 with de-O-acylated A1 LOS (FIG. 3, filled triangles), indicating that the removal of O-linked fatty acids did not alter the A1 LOS epitope. In contrast, MAb MB2-380-91 binding inhibition was completely abolished after dephosphorylation of A1 LOS (FIG. 3, filled squares), indicating that MAb MB2-380-91 recognizes a PEA dependent epitope in the LOS inner core.

Competition binding assays were also performed with MAb LOS-556-24 and NMB LOS coated microtiter plates, wherein MAb LOS-556-24 binding (i.e., binding to NMB LOS coated plates) was inhibited by both wild-type full length NMB LOS (Table 4, column 2) and truncated NMB-SS3 LOS (Table 4, column 4). These results demonstrate that MAb LOS-556-24 is specific to the inner core of NMB LOS. In addition, the inhibitory effects of full length NMB LOS and truncated NMB-SS3 LOS were largely abolished (Table 4, columns 3 and 5, respectively) after removal of the PEA groups (i.e., dephosphorylation), indicating that MAb LOS-556-24 binding is dependent on PEA substitution of NMB LOS.

These data taken together suggest that the five *N. meningitidis* LOS antigenic epitope groups described in Example 2 (based on antibody specificities) require phosphorylation of the LOS inner core, and are not dependent on the length of LOS outer core α-chain.

TABLE 4

COMPETITION BINDING ASSAY USING NMB LOS, DE-PHOSPHORYLATED NMB LOS, TRUNCATED NMB-SS3 LOS OR TRUNCATED AND DEPHOSPHORYLATED NMB-SS3 LOS AS COMPETITORS OF MAB LOS-556-24 BINDING TO TRUNCATED NMB-SS3 LOS

| [Competitor] | Percent Competition | | | |
|---|---|---|---|---|
| | LOS | LOS (De-Pho) | LOS (Trunc) | LOS (Trunc + De-pho) |
| 0.20 µg/mL | 58% | 11% | 92% | 13% |
| 0.39 µg/mL | 65% | 10% | 95% | 16% |
| 0.78 µg/mL | 68% | 16% | 96% | 19% |
| 1.56 µg/mL | 73% | 18% | 97% | 15% |
| 3.13 µg/mL | 74% | 15% | 96% | 15% |
| 6.25 µg/mL | 72% | 24% | 96% | 25% |
| 12.5 µg/mL | 75% | 26% | 95% | 28% |
| 25.0 µg/mL | 80% | 29% | 96% | 31% |
| 50.0 µg/mL | 88% | 25% | 97% | 34% |
| 100.0 µg/mL | 95% | 22% | 99% | 46% |

(De-Pho) = de-phosphorylated LOS;
(Trunc) = truncated LOS from galE mutant (NMB-SS3) and
[Competitor] = is the concentration of the LOS, LOS (De-Pho), LOS (Trunc) or LOS (De-Pho + Trunc).

Example 5

Structural Analysis of Meningococcal Wild-Type LOS

Several *N. meningitidis* LOS structures have been reported in the literature (Jennings et al., 1983; Cox et al., 2002; Beurret et al., 1990; Gamian et al., 1992; Pavliak et al., 1993; Kogan et al., 1997; Wakarchuk et al., 1998; McLeod Griffiss et al., 2000). As described above in Examples 2-4, monoclonal and polyclonal antibody binding to LOS from different *N. meningitidis* immunotypes revealed a binding specificity dependent on different substitutions with Glc and PEA moieties at the HepII residue of the LOS inner core.

As described above in Section A, *N. meningitidis* LOS contains a lipid-A component and a core oligosaccharide (OS) component. The core OS component comprises an outer core and an inner core (e.g., see FIG. 1). The expression of various core OS components depends on the growth conditions, the growth phase, and probably the absence or presence of exogenous N-acetyl neuraminic acid (NANA) (Verheul et al., 1993$^a$). The majority of *N. meningitidis* strains express more than one immunotype-specific epitopes on their LOS, leading to the classification of strains such as L3,7,9 and L1,8, for example. The LOS molecules from the *N. meningitidis* strains described in Example 1 were structurally characterized to determine structural variations and their influence on LOS antigenicity.

The overall makeup of the glycan molecules present in the LOSs were determined by mass spectrometry (MS)-based experiments. Matrix assisted laser desorption ionization-time of flight (MALDI-TOF) MS was carried out on the lipid-A-free core oligosaccharide (OS) and on de-O-acylated LOSs, and the glycosidic composition of the core OS was in general agreement with published literature.

Figure 4A:
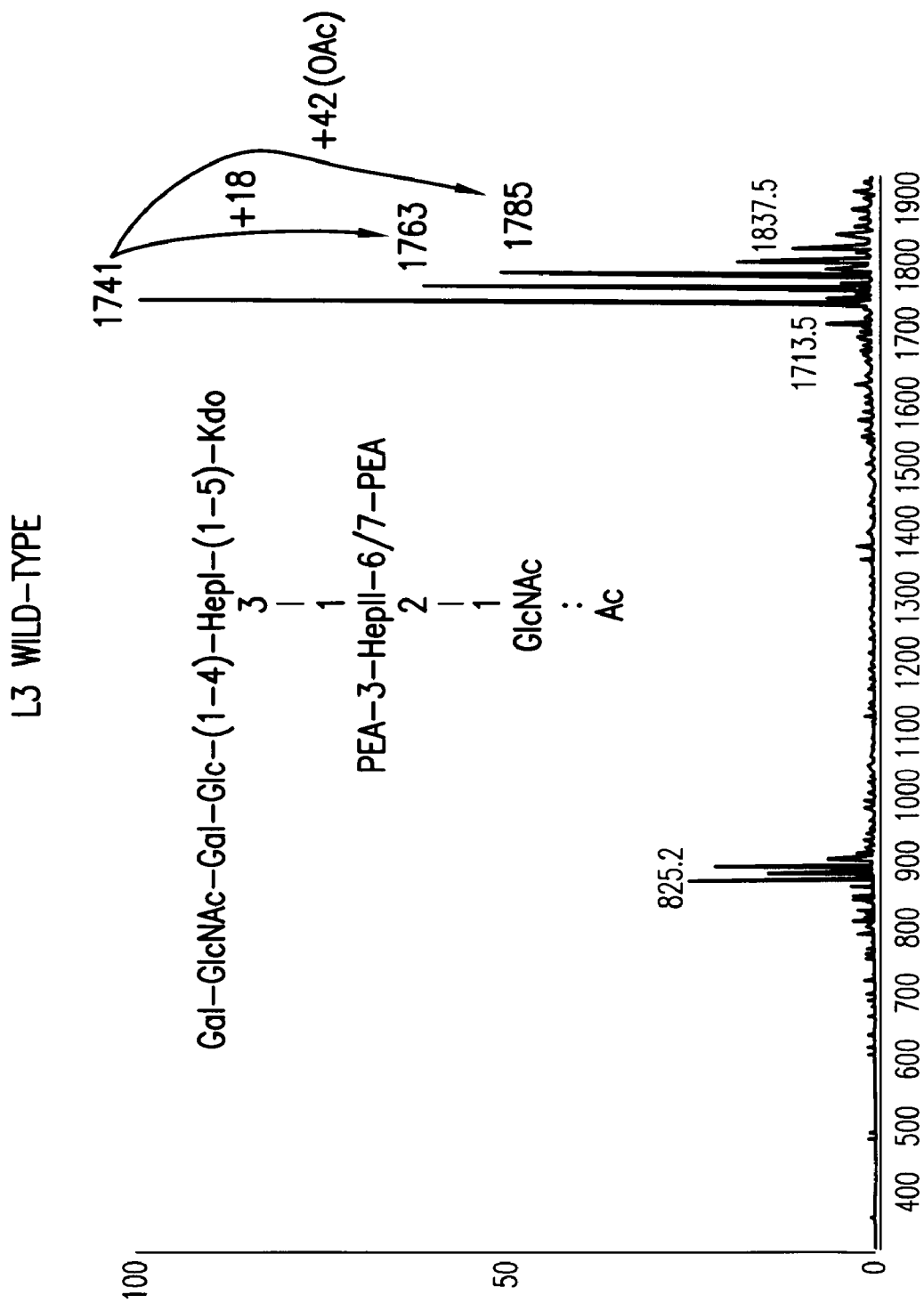
FIG. 4A is a mass spectral analysis and corresponding structure of core oligosaccharide prepared my mild acetic acid hydrolysis of LOSs from wild-type N. meningitidis 6275 (L3) immunotype expressing di-PEA inner core epitope.
Figure 4B:
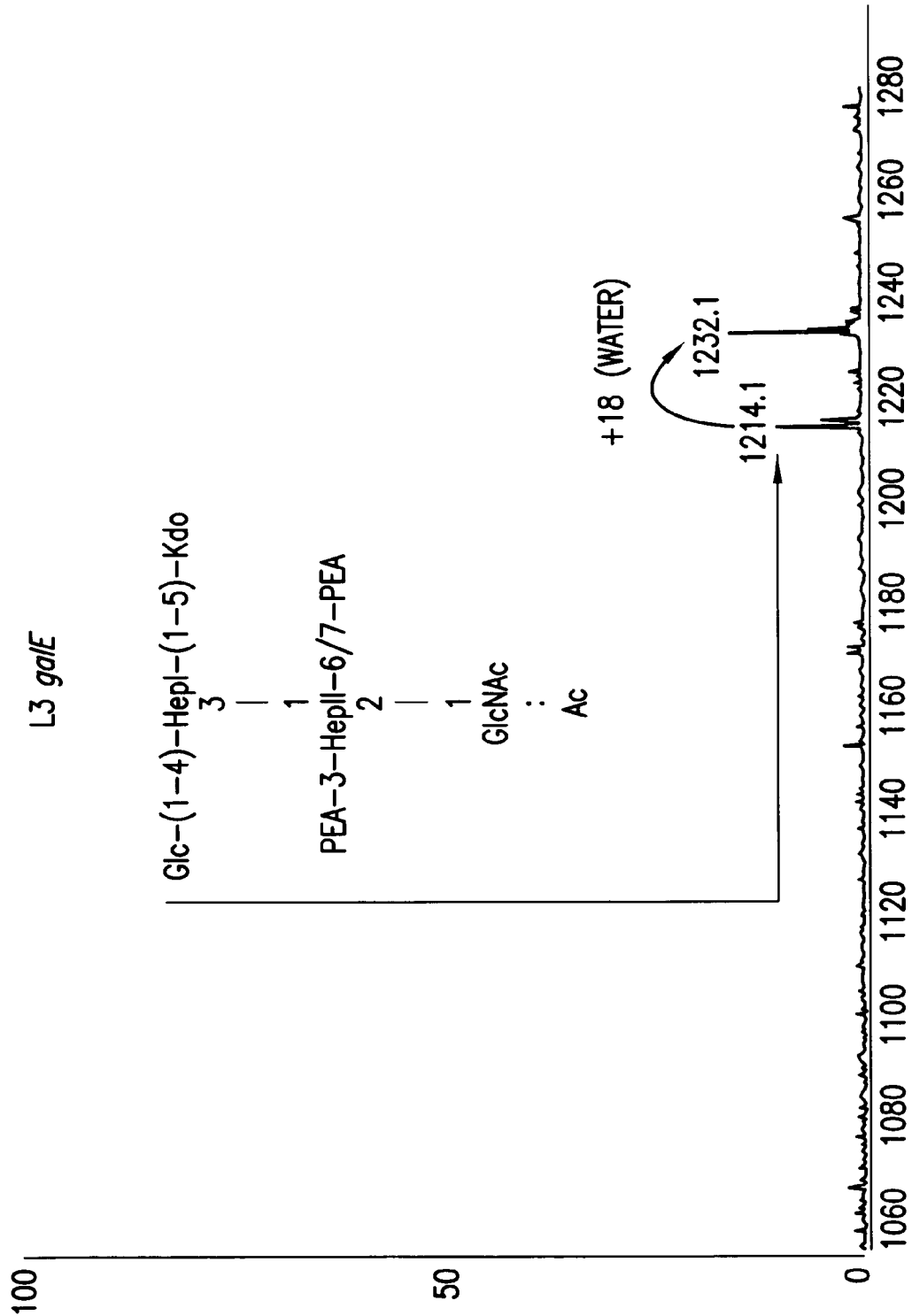
FIG. 4B is a mass spectral analysis and corresponding structure of core oligosaccharide prepared my mild acetic acid hydrolysis of LOSs from galE mutant N. meningitidis 7036-6275 (L3) immunotype expressing di-PEA inner core epitope.

However, novel inner core LOS structures were identified with antigenically important substitutions of the distal heptose (HepII) residue, wherein the HepII residue was substituted with two PEA moieties in wild-type *N. meningitidis* LOS. This LOS structure, with two PEA moieties, represents a major dominant structural component in L3 LOS (strain 6275) (FIG. 4A) and A1 (L8) LOS (Table 9). The *N. meningitidis* strain A1 was reported in the literature to be a L8 immunotype having a single PEA moiety (Gu et al, 1992). The same inner core substitutions of HepII with two PEA moieties were found among LOS inner core structures of immunotypes L9, L11, L12, and in the LOS from *N. meningitidis* clinical isolates H355 and 2996.

As described in Example 4, the specificity of the monoclonal antibodies MB2-380-91, MB2-134-19 and MB2-14-13, which bind to L1, L3 (6275), L9, L11, L12, A1 (L8), 2996 and H355 LOS, was dependent on the substitution of the HepII inner core with PEA. The binding of monoclonal antibodies MB2-380-91, MB2-134-19 and MB2-14-13 to *N. meningitidis* L1, L3 (6275), L9, L11, L12, A1 (L8), 2996 and H355 LOS was eliminated after removal of the PEA moieties with HF, indicating that a PEA substituted inner core is a specific epitope recognized by these MAbs.

These same monoclonal antibodies did not bind to L2, L4, L5, L6, L7, L8 (M978), L10, H44/76 (L3) or NMB (L2) LOSs (FIG. 2). Structural analysis of NMB (L2), L4, L7 L8 (M978) and H44/76 (L3) LOSs confirmed that these LOSs possess one PEA unit attached to the LOS inner core. For example, the PEA moiety in the L4 core OS is linked to O-6 of HepII (Table 9) and the PEA moiety in the L7 and H44/76 core OS is linked to O-3 of HepII (Table 9), as described by Kogan et al. (1997) and Plested et al. (1999). The majority of the PEA (60%) in NMB (L2) LOS is linked to 0-6 of HepII and a Glc residue is linked to O-3 of HepII, in agreement with the published literature (Rahman et al., 1998).

Figure 5A:
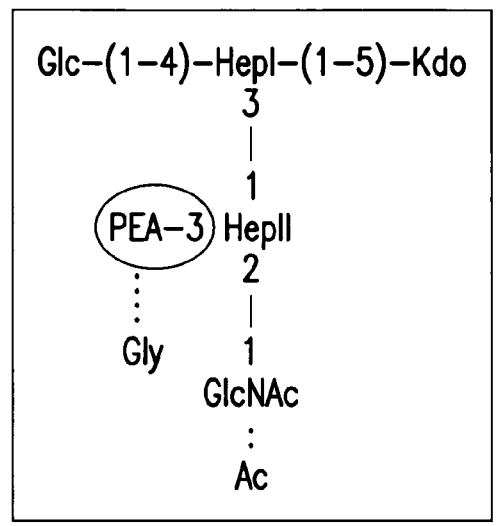
FIG. 5 shows the LOS inner core structures of PEA-3-HepII (structure A), HepII-6-PEA (structure B), Glc-3-HepII-6/7-PEA (structure C), PEA-3-HepII-6/7-PEA (structure D) and Glc-3-HepII (structure E).
Figure 5B:
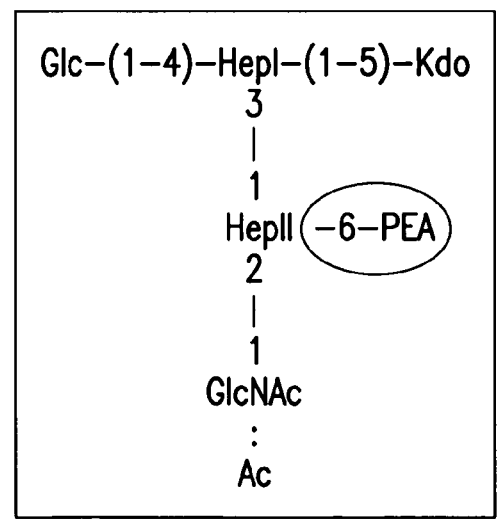
Figure 5C:
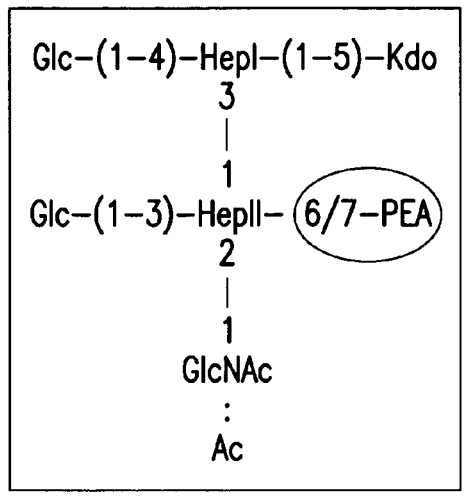
Figure 5D:
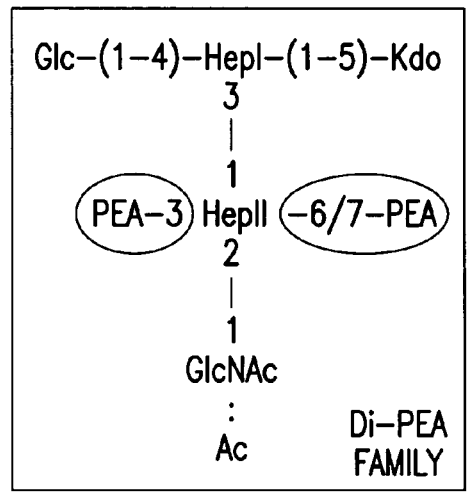

Thus, the structural analysis of *N. meningitidis* L3 (6275) (FIG. 4A), A1 (L8), L9 and 2996 LOS determined that two PEA moieties are simultaneously attached at O-3 and O-6 or O-3 and O-7 of the same HepII residue of the inner core (e.g., see FIG. 5D). The data in this example therefore suggest that two PEA moieties attached to HepII of the LOS inner core represent a novel epitope group expressed among a majority of *N. meningitidis* LOS immunotypes (e.g., L1, L3 (6275), L9, L11, L12, A1 (L8), 2996 and H355) and that this epitope is serologically distinct when compared to inner core LOS with one PEA attached at O-3 of HepII as described by Plested et al. (1999).

Figure 6A:
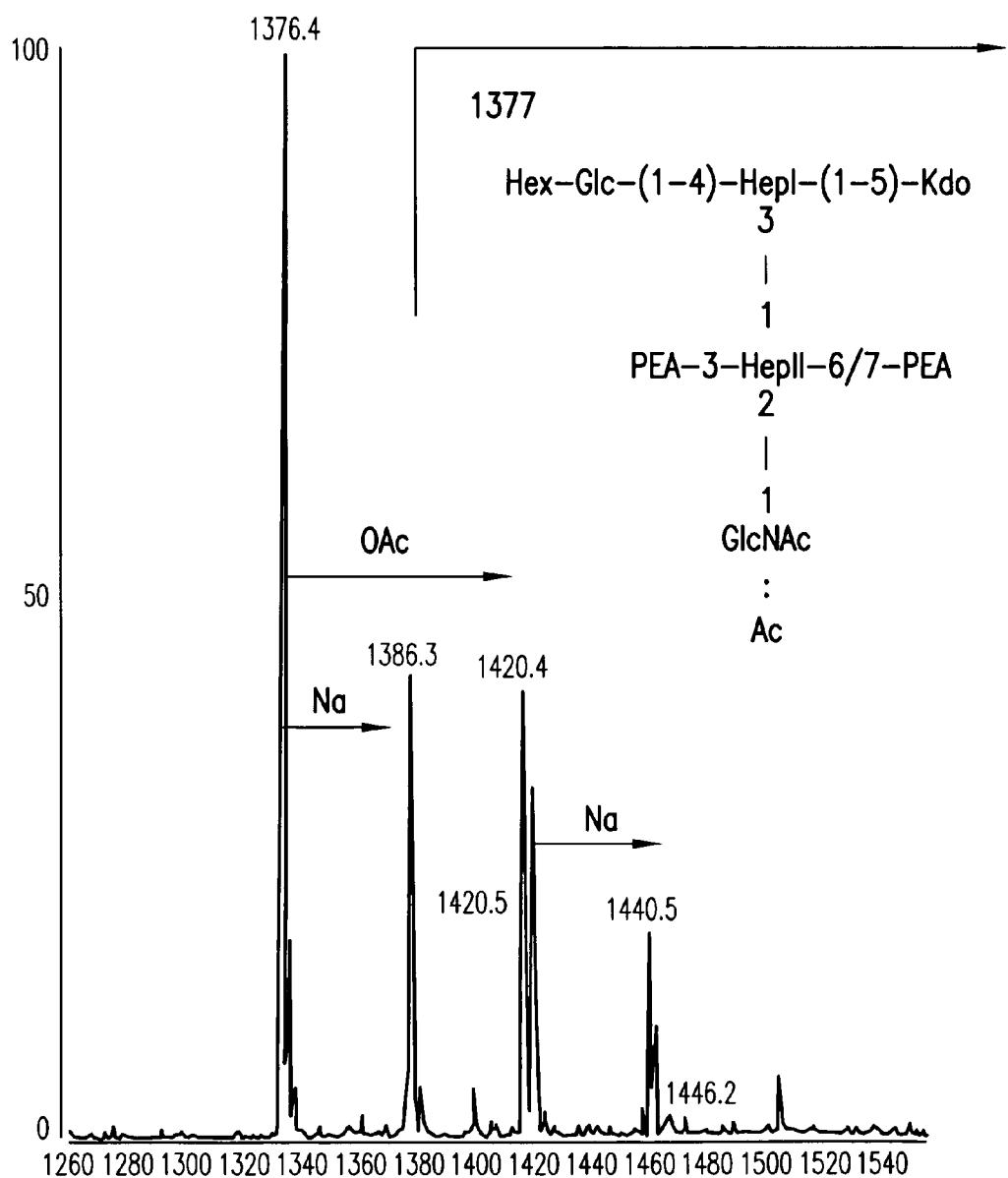
FIGS. 6A and 6B are mass spectra and corresponding structures of core oligosaccharide prepared my mild acetic acid hydrolysis of LOSs from wild-type N. meningitidis L11 and L12 immunotypes, respectively, expressing the di-PEA epitope.
Figure 6B:
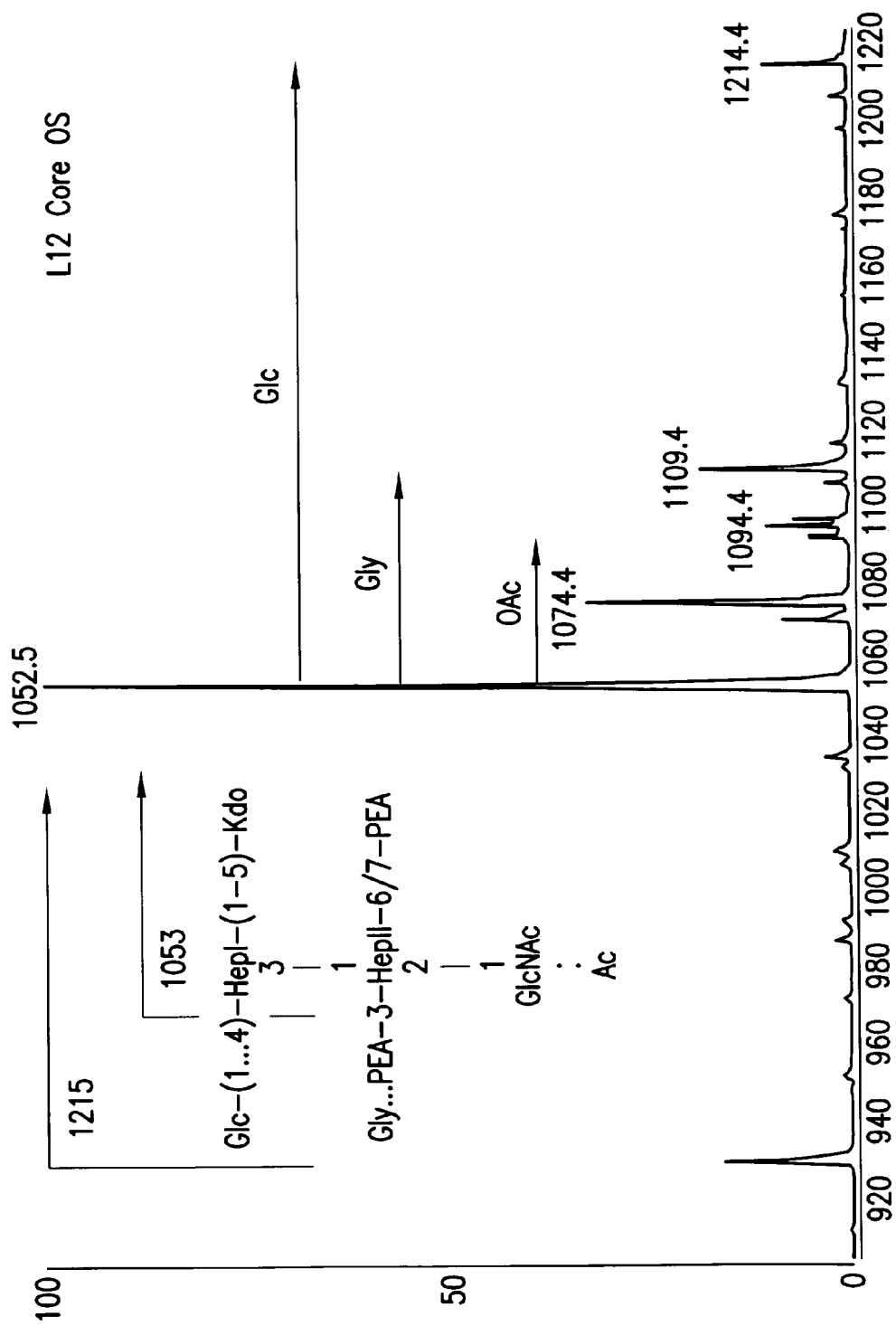

The structural analysis of *N. meningitidis* L11 LOS and L12 LOS, which are recognized by MB2-380-91, MB2-134-19 and MB2-14-13 MAbs, has not been described in the art. It was determined in the present invention, that immunotype L11 (FIG. 6A) and L12 (FIG. 6B) also comprise two PEA units attached to HepII the LOS inner core (i.e., PEA attached at O-3 and O-6 or O-3 and O-7 of the same HepII residue). Additionally, *N. meningitidis* L11 LOS and L12 LOS were observed to produce short outer-core regions, a di-hexose (Gal-1-4-Glc and/or Glc-1-4-Glc) in L11 and only trace amounts of a Glc unit in L12. The L12 immunotype was also observed to express a Gly residue (FIG. 6B, m/z 1109.4), a constituent also found in *N. meningitidis* strain H44/76.

Figure 5E:
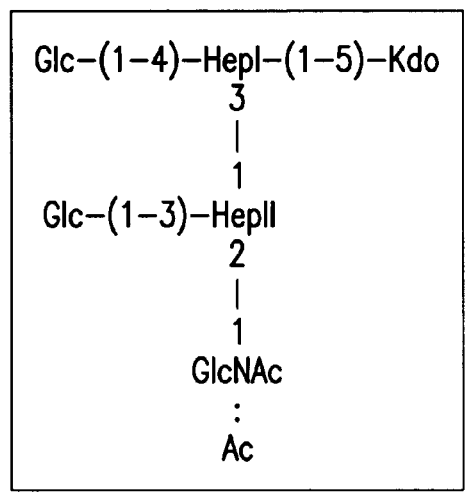
Figure 7:
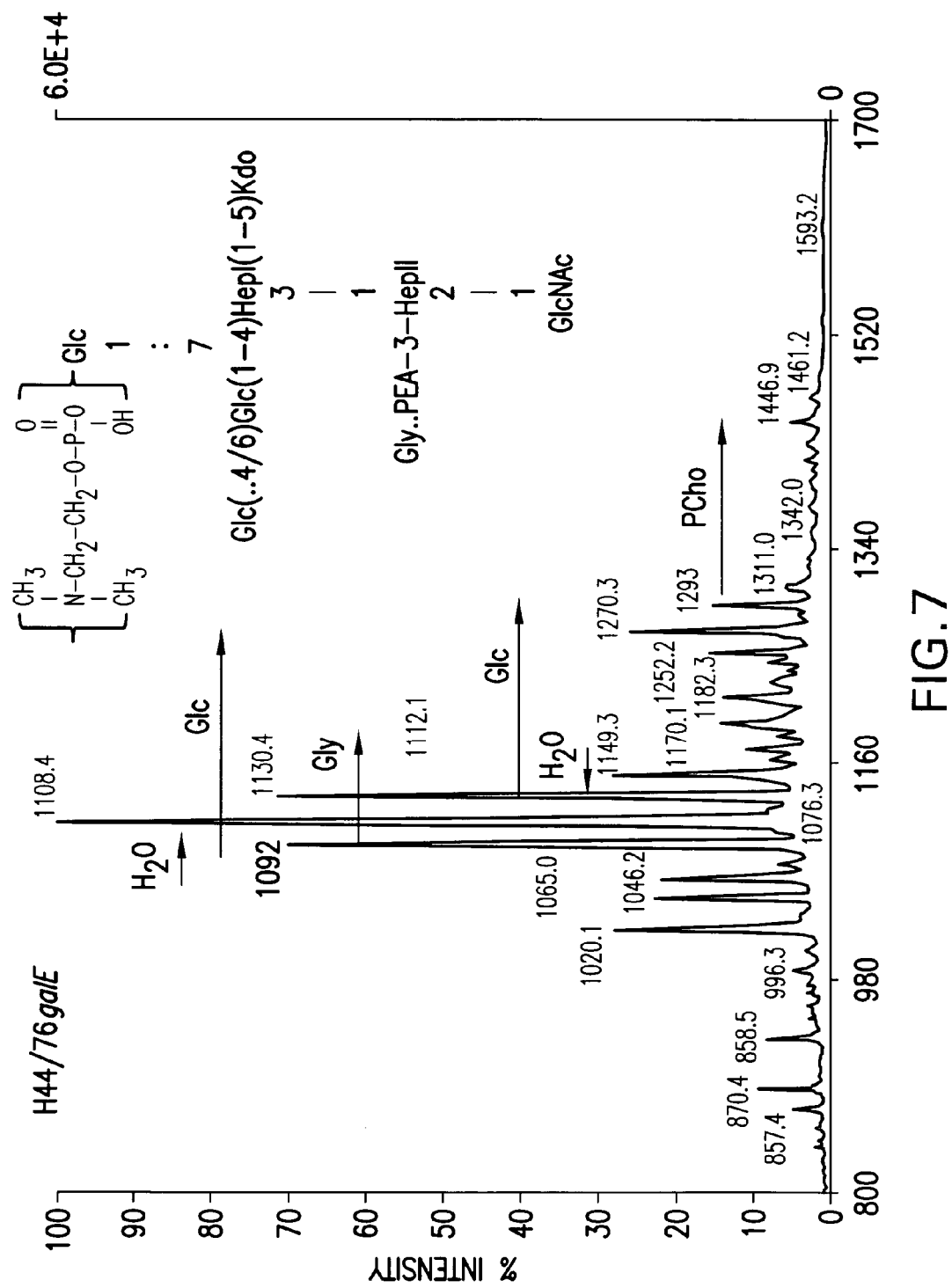
FIG. 7 shows the mass spectrum and corresponding structure of oligosaccharide from N. meningitidis galE mutant 7350-H44/76 (L3) expressing PEA epitope group I (PEA linked to O-3 of HepII) with a glycine (Gly) residue attached to the PEA and a phosphocholine (PCho) residue attached to the HepI residue.

Thus, the data set forth above suggest that an immunogenic composition for inducing a broad immune response against N. meningitidis immunotypes should at least comprise the following LOS components (FIG. 5): (i) PEA linked to O-6 position of HepII (FIG. 5B); (ii) glucose (Glc) linked to O-3 of HepII and PEA linked to O-6 or O-7 of HepII (FIG. 5C); (iii) PEA linked to O-3 of HepII (FIG. 5A); (iv) Glc linked to O-3 of HepII (FIG. 5E) and (v) PEA linked to O-3 and O-6 or O-3 and O-7 of HepII (FIG. 5D). In addition, the PEA linked to O-3 of HepII (group iii above) may further comprise a glycine (Gly) residue attached to the PEA (e.g., see FIG. 7) and/or a phosphocholine (PCho) residue attached to the HepII residue (e.g., see FIG. 7).

Example 6

Structural Analysis of LOS from *N. meningitidis* Wild-Type and GalE Mutant Strains The outer core of many *N. meningitidis* LOS immunotypes comprises glycan epitopes (e.g., lacto-N-neotetraose, N-acetyl neuraminic acid, paragloboside) that mimic human blood-group antigens, and as such, have the potential of inducing an autoimmune response in humans. The elucidation of the biosynthesis of *N. meningitidis* LOS has made it possible, via genetic manipulation of *N. meningitidis* genes, to eliminate these glycan epitopes. Several *N. meningitidis* mutations (e.g., galE, rfaK, pgm) resulting in the α-chain lacking these glycan epitopes have been described in the literature (Stephens et al., 1994; Andersen et al., 1995; Lee et al., 1995; Rahman et al., 2001).

In the following example, wild-type strains of *N. meningitidis* L2, L3 and L4 immunotypes were mutated at the galE gene (i.e., galE mutants), and the LOS structures of the mutants compared to the LOS structures of the wild-type parental strains. Thus, galE mutations were induced in the following parental strains: *N. meningitidis* strain 89I (L4 immunotype), PEA linked to O-6 position of HepII; *N. meningitidis* strain NMB (L2 immunotype), Glc linked to O-3 of HepII and PEA linked to O-7 of HepII or O-6 of HepII; *N. meningitidis* strain H44/76 (L3 immunotype), PEA linked to O-3 of HepII and *N. meningitidis* strain 6275 (L3 immunotype), PEA linked to O-3 and O-6 of HepII or PEA linked to O-3 and O-7 of HepII.

LOS representing an inner core with Glc linked to O-3 of HepII and no PEA linked to HepII can be prepared by dephosphorylation of LOS from a galE mutant of *N. meningitidis* strain NMB (or other strains expressing the L2 LOS inner core (i.e., Glc linked to O-3 of HepII and PEA linked to O-6/O-7 of HepII)).

A. Characterization of Wild-Type and GalE Mutant LOS from *N. meningitidis* Strain 6275 (L3 Immunotype)

Monosaccharide composition analysis (Sawardeker et al., 1967) carried out on the 6275 galE LOS (data not shown) revealed that the LOS was composed of D-glucose (Glc), L-glycero-D-manno-heptose (Hep) and N-acetyl-D-glucosamine (GlcNAc). The LOS of the wild-type 6275 parent strain, further comprised D-galactose (Gal), which was not observed in LOS from its galE mutant (7036-6275) confirming the absence of Gal and the truncation of the α-chain in the 6275 galE LOS.

Sugar linkage analysis (Ciucanu and Kerek, 1984) of the 6275 galE core OS (Table 5) detected terminal Glc (T-Glc), terminal GlcNAc (T-GlcNAc), 3,4-disubstituted Hep (3,4-Hep), minor quantities of 4-monosubstituted Glc (4-Glc), and a trace amount of 2-Hep and 2,3-disubstituted Hep (2,3-Hep). The core OS of the wild-type 6275 (L3) parent strain (Table 5) further comprised a terminal Gal (T-Gal), 3-monosubstituted Gal (3-Gal) and 4-monosubstituted GlcNAc (4-GlcNAc), which were not observed in 6275 galE core OS (Table 5), further confirming the absence of α-chain in the 6275 galE core OS. In addition, the absence of significant levels of 2-monosubstituted Hep (2-Hep) and 2,3-disubstituted Hep (2,3-Hep) indicates that HepII is phosphorylated.

TABLE 5

| | SUGAR LINKAGES OF *N. MENINGITIDIS* SEROGROUP B WILD-TYPE AND GALE MUTANT OLIGOSACCHARIDES | | | | | | | |
|---|---|---|---|---|---|---|---|---|
| Linkage Type | L3 Wild-Type | L3 galE | H44/76 Wild-Type | H44/76 galE | L4 Wild-Type | L4 galE | NMB (L2) Wild-Type | NMB (L2) galE |
| T-Glc | Traces | ++ | Traces | ++ | Traces | ++ | ++ | ++ |
| 4-Glc | ++ | + | ++ | + | ++ | + | ++ | + |
| T-Gal | ++ | − | ++ | − | ++ | − | ++ | − |
| 3-Gal | ++ | − | ++ | − | ++ | − | ++ | − |
| T-GlcNAc | ++ | ++ | ++ | ++ | ++ | ++ | ++ | ++ |
| 4-GlcNAc | ++ | − | ++ | − | ++ | − | ++ | − |
| 2-Hep | Traces | Traces | Traces | Traces | Traces | Traces | Traces | Traces |
| 3,4-Hep | ++ | ++ | ++ | ++ | ++ | ++ | ++ | ++ |
| 2,3-Hep | Traces | Traces | Traces | Traces | Traces | Traces | + | + |

"T" = Terminal;
− = Not present;
++ = Present in a relatively higher label;
+ = Present in a relatively lower label but > 10%;
Traces = Present < 10%;
L3 Wild-Type = Nm 6275,
L3 galE = Nm 7036-6275;
H44/76 galE = Nm 7350-H44/76;
L4 Wild-Type = Nm 89I,
L4 galE = Nm 7350-6275;
NMB (L2) galE = Nm 7350-NMB;

Mass spectrometry of the 6275 galE lipid A-free core OS (Table 6) were compared to the wild-type 6275 parental strain (Table 7). The MALDI-TOF-MS spectra of 6275 galE lipid A-free core OS (Table 6) gave primary m/z ions at 1276.08 [1277.08 (1276.08+H] that corresponded to 2 PEA, 1 Glc, 1 GlcNAc, 1 KDO, 2 Hep and 1 Ac, which accounted for an inner-core region containing two PEA units, but lacking the typical N. meningitidis outer-core region [Neu5Ac-(2→3 or 6)-Gal-(1→4)-GlcNAc-(1→3)-Gal] of the 6275 wild-type OS (Table 7). An additional minor ion at m/z 1437.75 [1276.08+ 162] suggested that a Glc residue might substitute some of 6275 galE core OS molecules of their truncated α-chain.

TABLE 6

OBSERVED MOLECULAR IONS AND PROPOSED COMPOSITION OF 6275 GALE MUTANT OS

| Observed ions $(M - H)^-$ | Observed molecular Mass | Calculated molecular mass | Proposed composition |
|---|---|---|---|
| 1214.55 | 1215.55 | 1215.96 | $GlcNAc_1\ Glc_1\ Hep_2\ PEA_2\ Kdo\text{-}H_2O$ |
| 1232.64 | 1233.64 | 1233.97 | $GlcNAc_1\ Glc_1\ Hep_2\ PEA_2\ Kdo$ |
| 1255.45 | 1256.45 | 1256.96 | $GlcNAc_1\ Glc_1\ Hep_2\ PEA_2\ Kdo\ Na$ |
| 1276.08 | 1277.08 | 1277.02 | $GlcNAc_1\ Glc_1\ Hep_2\ PEA_2\ Kdo\ Ac$ |
| 1296.74 | 1297.74 | 1295.96 | $GlcNAc_1\ Glc_1\ Hep_2\ PEA_2\ PO_4\ Kdo\text{-}H_2O$ |
| 1318.69 | 1319.69 | 1318.95 | $GlcNAc_1\ Glc_1\ Hep_2\ PEA_2\ PO_4\ Kdo\text{-}H_2O\ Na$ |
| 1395.99 | 1396.99 | 1396.11 | $GlcNAc_1\ Glc_2\ Hep_2\ PEA_2\ Kdo$ |
| 1418.22 | 1419.22 | 1419.10 | $GlcNAc_1\ Glc_2\ Hep_2\ PEA_2\ Kdo\ Na$ |
| 1437.75 | 1438.75 | 1439.16 | $GlcNAc_1\ Glc_2\ Hep_2\ PEA_2\ Kdo\ Ac$ |
| 1457.25 | 1458.25 | 145810 | $GlcNAc_1\ Glc_2\ Hep_2\ PEA_2\ PO_4\ Kdo\text{-}H_2O$ |
| 1479.97 | 1480.97 | 1481.08 | $GlcNAc_1\ Glc_2\ Hep_2\ PEA_2\ PO_4\ Kdo\text{-}H_2O\ Na$ |
| 1498.86 | 1499.86 | 1499.09 | $GlcNAc_1\ Glc_2\ Hep_2\ PEA_2\ PO_4\ Kdo\ Na$ |

TABLE 7

OBSERVED MOLECULAR IONS AND PROPOSED COMPOSITION OF WILD-TYPE 6275 OS

| Observed ions $(M - H)^-$ | Observed molecular Mass | Calculated molecular mass | Proposed composition |
|---|---|---|---|
| 1741.00 | 1742.00 | 1743.44 | $GlcNAc_2\ Gal_2\ Glc_1\ Hep_2\ PEA_2\ Kdo\text{-}H_2O$ |
| 1760.76 | 1761.76 | 1761.45 | $GlcNAc_2\ Gal_2\ Glc_1\ Hep_2\ PEA_2\ Kdo$ |
| 1783.25 | 1784.25 | 1784.44 | $GlcNAc_2\ Gal_2\ Glc_1\ Hep_2\ PEA_2\ Kdo\ Na$ |
| 1802.50 | 1803.50 | 1804.5 | $GlcNAc_2\ Gal_2\ Glc_1\ Hep_2\ PEA_2\ Kdo\ Ac$ |
| 1822.85 | 1823.85 | 1823.44 | $GlcNAc_2\ Gal_2\ Glc_1\ Hep_2\ PEA_2\ PO_4\ Kdo\text{-}H_2O$ |
| 1844.71 | 1845.71 | 1846.43 | $GlcNAc_2\ Gal_2\ Glc_1\ Hep_2\ PEA_2\ PO_4\ Kdo\text{-}H_2O\ Na$ |

The location of PEA groups on the wild-type 6275 LOS and galE mutant 6275 LOS were determined by methylation of the OS, followed by 48% HF treatment and trideuteromethylation. In this method the location of a trideuteromethyl group indicates the location of the phosphate or PEA substituent in the original LOS or OS sample. GC-MS analysis of the wild-type 6275 and galE mutant 6275OS revealed the presence of 3,6-disubstitued trideuteromethyl 2-monosubstituted HepII and 3,7-disubstitued trideuteromethyl 2-mono-substituted HepII (Table 8), indicating that the major form of L3 LOS (or OS) contains PEA groups (i.e., di-PEA) at both the O-3 and O-6 positions of HepII or the O-3 and O-7 positions of HepII.

TABLE 8

PHOSPHOETHANOLAMINE (PEA) LOCATIONS AT HEPII OF SEROGROUP B N. MENINGITIDIS WILD-TYPE AND GALE MUTANT OLIGOSACCHARIDES

| HepII Residue | PEA Group Locations | L3 Wild-Type | L3 galE | H44/76 Wild-Type | H44/76 galE | L4 Wild-Type | L4 galE | NMB Wild-Type | NMB galE |
|---|---|---|---|---|---|---|---|---|---|
| 2-Hep | — | Traces | Traces | Traces | Traces | Traces | Traces | Traces | Traces |
| 2-Hep | 3 | − | − | + | + | − | − | Traces | Traces |
| 2-Hep | 6 | − | − | Traces | Traces | + | + | Traces | Traces |
| 2-Hep | 7 | − | − | Traces | Traces | Traces | Traces | Traces | Traces |
| 2-Hep | 3, 6 | + | + | − | − | − | − | Traces | Traces |
| 2-Hep | 3, 7 | + | + | − | − | − | − | Traces | Traces |

TABLE 8-continued

PHOSPHOETHANOLAMINE (PEA) LOCATIONS AT HEPII OF SEROGROUP B *N. MENINGITIDIS* WILD-TYPE AND GALE MUTANT OLIGOSACCHARIDES

| HepII Residue | PEA Group Locations | L3 Wild-Type | L3 galE | H44/76 Wild-Type | H44/76 galE | L4 Wild-Type | L4 galE | NMB Wild-Type | NMB galE |
|---|---|---|---|---|---|---|---|---|---|
| 2,3-Hep | — | Traces | Traces | Traces | Traces | Traces | Traces | + | + |
| 2,3-Hep | 6 | Traces | Traces | Traces | Traces | Traces | Traces | + | + |
| 2,3-Hep | 7 | Traces | Traces | Traces | Traces | Traces | Traces | + | + |

− = Not present;
+ = Present in a significant label;
Traces = Present < 10%;
L3 Wild-Type = Nm 6275,
L3 galE = Nm 7036-6275;
H44/76 galE = Nm 7350-H44/76;
L4 Wild-Type = Nm 89I,
L4 galE = Nm 7350-6275;
NMB galE = Nm 7350-NMB.

The O-acetylation and presence of PEA moieties in both 6275 galE OS and 6275 wild-type OS was confirmed by $^1$H NMR analysis. The integration of the O-acetyl (δ 2.19) and N-acetyl (δ 2.12 and 2.05) methyl protons indicated that 36% of the 6275 wild-type and 6275 galE. OS samples are O-acetylated (data not shown). The proton resonances at δ 3.29 and δ 4.17 are due to the PEA groups (—O—CH$_2$C$\underline{H}_2$—NH$_2$ and —O—C$\underline{H}_2$CH$_2$—NH$_2$, respectively).

The location of PEA groups was further confirmed by one-dimensional $^{31}$P NMR and two-dimensional $^1$H-$^{31}$P NMR spectroscopy. The one-dimensional $^{31}$P-NMR spectrum of the OS showed that it contained four different phosphate NMR signals at δ −0.74, −0.63, −0.09, and −0.12. The locations of PEA groups in 6275 galE OS were determined by a two-dimensional $^1$H-$^{31}$P heterogeneous multiple quantum correlation (HMQC) NMR spectroscopy. The phosphate signals at δ −0.122 and −0.098 were coupled to H-7 and H-6 protons, respectively, (4.05, 4.52) of HepII, and δ −0.74 and −0.64 were coupled to two different H-3 protons, respectively, (4.32, 4.34) of HepII (spectrum not shown). These NMR data further demonstrate the location of PEA groups both at O3 and O-7 of HepII or O-3 and O-6 positions of HepII.

The dominant structure of 6275 galE core OS described above is delineated in FIG. 5D. Importantly, the 6275 galE OS contained two PEA units attached to the O-3, O-6 position and the O-3, O-7 position of HepII. Additionally a minor amount of an extra glucose was also present in the 6275 galE OS. The location of two PEAs at O-3, O-6 and O-3, O-7 of HepII was observed in the *N. meningitidis* LOS of L3 (6275), L9, L11, L12 and A1 (Table 9).

TABLE 9

STRUCTURAL CHARACTERIZATION OF OLIGOSACCHARIDES PREPARED BY HYDROLYSIS OF LOSS FROM *N. MENINGITIDIS* STRAINS REPRESENTING L1-L12 IMMUNOTYPES, WILD-TYPE STRAINS AND GALE MUTANT STRAINS

| Immunotype | Observed M/z (ESI-MS) | Composition | PEA (GC-MS, NMR) | % Ac at GlcNAc | Gly | PCho |
|---|---|---|---|---|---|---|
| L1 | 1415.4 | 2Gal, 1Glc, 1GlcNAc, 2Hep, 1Kdo, 1PEA | ND | 5% | | |
| | 1253.5 | 1Gal, 1Glc, 1GlcNAc, 2Hep, 1Kdo, 1PEA | | | | |
| | 1091.4 | 1Glc, 1GlcNAc, 2Hep, 1Kdo, 1PEA | | | | |
| NMB(L2) | 1780.7 | 2Gal, 2Glc, 2GlcNAc, 2Hep, 1Kdo, 1PEA | PEA-7 (40%) PEA-6 (60%) | 50% | | |
| L3 | 1741.5 | 2Gal, 1Glc, 2GlcNAc, 2Hep, 1Kdo, 2PEA | PEA-3, 6/7 | 50% | | |
| L4 | 1618.7 | 2Gal, 1Glc, 2GlcNAc, 2Hep, 1Kdo, 1PEA | PEA-6 | 60% | | |
| L5 | 1818.8 | 2Gal, 1Glc, 2GlcNAc, 2Hep, 1Kdo | | 20% | | |
| | 1656.9 | 1Gal, 1Glc, 2GlcNAc, 2Hep, 1Kdo | | | | |
| | 1454.2 | 1Gal, 1Glc, 1GlcNAc, 2Hep, 1Kdo | | | | |
| | 1292.1 | 1Glc, 1GlcNAc, 2Hep, 1Kdo | | | | |
| | 1980.5 | 2Gal, 2Glc, 2GlcNAc, 2Hep, 1Kdo | | | | |
| L6 | 1457.6 | 1Gal, 1Glc, 2GlcNAc, 2Hep, 1Kdo, 1PEA | ND | 40% | | |
| | 1580.5 | 2Gal, 1Glc, 2GlcNAc, 2Hep, 1Kdo, 2PEA | | | | |
| | 1619.6 | 2Gal, 1Glc, 2GlcNAc, 2Hep, 1Kdo, 1PEA | | | | |
| L7 | 1618.8 | 2Gal, 1Glc, 2GlcNAc, 2Hep, 1Kdo, 1PEA | PEA-3 | 5% | | |
| | 1456.7 | 1Gal, 1Glc, 2GlcNAc, 2Hep, 1Kdo, 1PEA | PEA-3 | | | |
| | 1253.7 | 1Gal, 1Glc, 1GlcNAc, 2Hep, 1Kdo, 1PEA | PEA-3 | | | |
| | 1091.7 | 1Glc, 1GlcNAc, 2Hep, 1Kdo, 1PEA | PEA-3 | | | |
| L8 | 1273.40 | 1Gal, 1Glc, 1GlcNAc, 2Hep, 1Kdo, 1PEA | PEA-3 | 40% | | |
| L9 | 1637.6 | 2Gal, 1Glc, 2GlcNAc, 2Hep, 1Kdo, 1PEA | PEA-3 | 50% | | |
| | 1761.6 | 2Gal, 1Glc, 2GlcNAc, 2Hep, 1Kdo, 2PEA | PEA-3, 6/7 | | | |
| L10 | 1618.9 | 2Gal, 1Glc, 2GlcNAc, 2Hep, 1Kdo, 1PEA | PEA-3 | 10% | | |
| L11 | 1376.4 | 2Hex, 1GlcNAc, 2Hep, 1Kdo, 2PEA | PEA-3, 6/7 | 50% | | |

TABLE 9-continued

STRUCTURAL CHARACTERIZATION OF OLIGOSACCHARIDES PREPARED BY HYDROLYSIS OF LOSS FROM *N. MENINGITIDIS* STRAINS REPRESENTING L1-L12 IMMUNOTYPES, WILD-TYPE STRAINS AND GALE MUTANT STRAINS

| Immunotype | Observed M/z (ESI-MS) | Composition | PEA (GC-MS, NMR) | % Ac at GlcNAc | Gly | PCho |
|---|---|---|---|---|---|---|
| L12 | 1052.5 | 1GlcNAc, 2Hep, 1Kdo, 2PEA | PEA-3, 6/7 | 10% | | |
| | 1109.4 | 1GlcNAc, 2Hep, 1Kdo, 2PEA, 1Gly | PEA-3, 6/7 | | Yes | |
| | 929.6 | 1GlcNAc, 2Hep, 1Kdo, 1PEA | PEA-3 | | | |
| | 1214.4 | 1Glc, 1GlcNAc, 2Hep, 1Kdo, 2PEA | PEA-3, 6/7 | | | |
| H355 | 1253.7 | 1Gal, 1Glc, 1GlcNAc, 2Hep, 1Kdo, 1PEA | PEA-3 | 40% | | |
| | 1618.6 (5%) | 2Gal, 1Glc, 2GlcNAc, 2Hep, 1Kdo, 1PEA | PEA-3 | | | |
| | 1376.0 (2%) | 1Gal, 1Glc, 1GlcNAc, 2Hep, 1Kdo, 2PEA | PEA-3, 6/7 | | | |
| 2996 | 1741.7 | 2Gal, 1Glc, 2GlcNAc, 2Hep, 1Kdo, 2PEA | PEA-3, 6/7 | 90% | | |
| | 1618.6 | 2Gal, 1Glc, 2GlcNAc, 2Hep, 1Kdo, 1PEA | PEA-3 | | | |
| H44/76 | 1618.8 | 2Gal, 1Glc, 2GlcNAc, 2Hep, 1Kdo, 1PEA | PEA-3 | | | |
| | 1675.5 | 2Gal, 1Glc, 2GlcNAc, 2Hep, 1Kdo, 1PEA, 1Gly | PEA-3 | | Yes | |
| | 3109.2 (Lipid A) | 2Gal, 2Glc, 2GlcNAc, 2Hep, 1Kdo, 1PEA, 1PCho | PEA-3 | | | Yes |
| A1 (L8) | 1394.2 | 2Glc, 1GlcNAc, 2Hep, 1Kdo, 2PEA | PEA-3, 6/7 | 90% | | |
| | 1271.4 | 2Glc, 1GlcNAc, 2Hep, 1Kdo, 1PEA | PEA-3 | | | |
| | 1556.1 | 3Glc, 1GlcNAc, 2Hep, 1Kdo, 2PEA | PEA-3, 6/7 | | | |
| | 1710.8 | 3Glc, 1GlcNAc, 2Hep, 1Kdo, 2PEA, 1PCho | PEA-3, 6/7 | | | Yes |
| L3galE | 1232.1 | 1Glc, 1GlcNAc, 2Hep, 1Kdo, 2PEA, 2PCho | PEA-3, 6/7 | | | |
| H44/76galE | 1091.4 | 1Glc, 1GlcNAc, 2Hep, 1Kdo, 1PEA | PEA-3 | | | |
| | 1148.3 | 1Glc, 1GlcNAc, 2Hep, 1Kdo, 1PEA, 1Gly | PEA-3 | | Yes | |
| | 1253.3 | 2Glc, 1GlcNAc, 2Hep, 1Kdo, 1PEA | PEA-3 | | | |
| | 1415.4 | 3Glc, 1GlcNAc, 2Hep, 1Kdo, 1PEA | PEA-3 | | | |
| | 986.5 | 1GlcNAc, 2Hep, 1Kdo, 1PEA, 1Gly | PEA-3 | | Yes | |
| | 1446.9 (—$H_2O$) | 2Glc, 1GlcNAc, 2Hep, 1Kdo, 1PEA, 1Gly, 1PCho | PEA-3 | | | Yes |
| NMBgalE | 1415.7 | 3Glc, 1GlcNAc, 2Hep, 1Kdo, 1PEA | PEA-7 | 60% | | |
| | 1253.7 | 2Glc, 1GlcNAc, 2Hep, 1Kdo, 1PEA | (40%) | | | |
| | 1130.5 | 2Glc, 1GlcNAc, 2Hep, 1Kdo, | PEA-6 (60%) | | | |
| 89IGalE | 1092 | 1Glc, 1GlcNAc, 2Hep, 1Kdo, 1PEA | PEA-6 | 60% | | |
| | 1254 | 2Glc, 1GlcNAc, 2Hep, 1Kdo, 1PEA | PEA-6 | | | |

B. Characterization of Wild-Type and GalE Mutant LOS from *N. meningitidis* Strain H44/76 (L3 Immunotype)

Monosaccharide composition analysis (Sawardeker et al., 1967) carried out on the H44/76 galE LOS (7350-H44/76 LOS) (data not shown) revealed that the LOS was composed of D-glucose (Glc), L-glycero-D-manno-heptose (Hep) and N-acetyl-D-glucosamine (GlcNAc). Monosaccharide composition analysis (data not shown) of the wild-type H44/76 parental strain demonstrated the presence of D-galactose (Gal), which was not observed in H44/76 galE mutant LOS, confirming the absence of Gal and the truncation of the α-chain in the H44/76 galE LOS.

Sugar linkage analysis of the H44/76 galE core OS (Table 5 above) detected terminal Glc (T-Glc), terminal GlcNAc (T-GlcNAc), 4-Glc, 3,4-disubstituted Hep (3,4-Hep), and a trace amount of 2-monosubstituted Hep (2-Hep) and 2,3-disubstituted Hep (2,3-Hep). The core OS of the wild-type H44/76 parent strain further comprised a terminal Gal (T-Gal), 3-monosubstituted Gal (3-Gal), and 4-monosubstituted GlcNAc (4-GlcNAc), which were not observed in the H44/76 galE OS. The absence of significant levels of 2-monosubstituted and 2,3-disubstituted Hep indicates that HepII is phosphorylated.

Mass spectra on the H44/76 galE lipid-A-free core OS were compared to the wild-type H44/76 parental strain to confirm the overall composition (Table 9 above). The ES-MS spectra of H44/76 galE lipid-A-free core OS gave primary m/z ions at 1091.4 [1110 (1092+$H_2O$)] that corresponded to 1 PEA, 1 Glc, 1 GlcNAc, 1 KDO and 2 Hep units (Table 7), which accounted for an inner-core region containing one PEA unit, but lacking the typical *N. meningitidis* outer-core region [Neu5Ac-(2→3 or 6)-Gal-(1→4)-GlcNAc-(1→3)-Gal]. An additional ion at m/z 1148.3 [1091.4+57] suggested that some of H44/76 galE core OS molecules were substituted further by a glycine (Gly) residue (e.g., see FIG. 7). The Gly component was also detected in the wild-type H44/76 parent strain.

Tandem mass spectrometry (MS/MS) of m/z 1148.3 yielded m/z 970, demonstrating the loss of PEA and Gly simultaneously [179 a.m.u.=PEA (123 a.m.u.)+Gly (57 a.m.u.)] (data not shown). An additional MS/MS experiment on m/z 970 (data not shown) demonstrated the sequential loss of the monosaccharide units which makeup the inner-core, and thus confirmed the composition and structural arrangement of the H44/76 galE core OS. It should be noted that additional glucosylations were detected in the H44/76 galE core region. These extra glucose residues were present in minor amounts (<5%) and could be observed in the ES-MS experiments for H44/76 galE and wild-type H44/76.

MALDI-TOF-MS on the de-O-acylated H44/76 galE LOS yielded dominant m/z ions at 952.00 for the lipid-A (PPEA$^2$, GlcN$^2$, N-linked fatty acids), and at m/z 2265 that corresponded to lipid-A, 2 KDO units, 1 Glc, 1 GlcNAc, 2 Hep residues and 1 PEA moiety (data not shown). It was also observed that H44/76 galE LOS carried an extra Glc and phosphorylcholine (PCho) (m/z 1147). A MALDI-TOF-MS experiment performed on the wild-type H44/76 LOS also detected trace amounts of Glc and PCho moieties (m/z 3109). Two sites involved in the aberrant glucosylation were deduced from the methylation linkage analysis, the sites being O-4 of the distal β-Glc (4-monosubstituted Glc) and at O-7 of HepI (3,4,7-trisubstituted HepI).

The location of the PEA group was determined as described above. GC-MS analysis revealed the presence of significant levels of 3-monosubstitued trideuteromethyl-2-monosubstituted Hep (data not shown), indicating that the major form of H44/76 LOS or OS contains a PEA group at the O-3 positions of HepII (Table 8).

A 1-D $^{31}$P-NMR study performed on H44/76 galE core OS fraction (devoid of the Gly unit) clearly showed a single resonance at $\delta_P$ 0.42, which did not change chemical shift at higher pH, which is indicative of a single diester-phosphate entity (spectrum not shown). A 2-D $^1$H-$^{31}$P correlation NMR experiment (spectrum not shown) demonstrated the "through-bond" connectivities between the phosphate and the two-methylene entities (3.22 ppm and 4.075 ppm) of the PEA and H-3 (4.28 ppm) of HepII, which confirmed the connection of a single PEA moiety to HepII in H44/76 galE LOS.

The dominant structure of H44/76 galE core OS described above is delineated in FIG. 5A. Thus, the H44/76 galE OS contained one PEA unit attached to position O-3 of HepII. Additional structural features, not previously described in the art, were that some OS molecules of H44/76 galE included Gly and PCho residues, and in minor quantities, extra glucose residues. The presence of a single PEA at O-3 of HepII was also observed in the LOS from *N. meningitidis* immunotypes L7, L8 (M978) and H355 (Table 9).

C. Characterization of Wild-Type and GalE Mutant LOS from *N. meningitidis* Strain 89I (L4 Immunotype)

Monosaccharide composition analysis of *N. meningitidis* L4 galE LOS (strain 89I) revealed that this LOS was composed of D-glucose (Glc), L-glycero-D-manno-heptose (Hep) and N-acetyl-D-glucosamine (GlcNAc). No galactose (Gal) was detected. Sugar linkage analysis of L4 galE core OS (Table 5 above) detected terminal Glc (T-Glc), terminal GlcNAc (T-GlcNAc), 3,4-disubstituted HepI, and a trace amount 2-monosubstituted HepII.

MALDI-TOF-MS spectra of the de-O-acylated 89I galE LOS contained m/z ions characterizing the inner-core region carrying one PEA unit (m/z 2264). Table 9 above shows the m/z values obtained from ES-MS experiments on 89I galE core OS It was also noted that an extra Glc unit may be added to the inner-core at O-4 of β-Glc.

The location of the PEA group was determined as described above. GC-MS analysis demonstrated the presence of significant levels of 6-monosubstitued trideuteromethyl-2-monosubstituted Hep in the 89I galE core OS (Table 8), suggesting that the majority of 89I galE LOS or core OS contains a PEA group at the O-6 positions of HepII.

1-D $^{31}$P-NMR studies carried out on 89I galE core OS fraction showed a single resonance at $\delta_P$ 1.05, which did not change chemical shift at higher pH, indicative of a single diester-phosphate entity (spectra not shown). A 2-D $^1$H-$^{31}$P correlation NMR experiment showed the through-bond connectivities between the phosphate and the two methylene entities (3.28 ppm and 4.14 ppm) of the PEA and H-6 (4.55 ppm) of HepI, confirming the attachment of a single PEA moiety to HepII in 89I galE LOS.

The dominant structure of the 89I galE core OS is presented in FIG. 5B, which shows the core OS structure comprising one PEA unit attached to position O-6 of HepII.

D. Characterization of Wild-Type and GalE Mutant LOS from *N. meningitidis* Strain NMB (L2 Immunotype)

Monosaccharide composition analysis of *N. meningitidis* NMB galE LOS revealed that this LOS was composed of D-glucose (Glc), L-glycero-D-manno-heptose (Hep) and N-acetyl-D-glucosamine (GlcNAc). No galactose was detected. Sugar linkage analysis of NMB galE core OS (Table 5 above) detected terminal Glc (T-Glc), terminal GlcNAc (T-GlcNAc), 3,4-disubstituted HepI, 2,3-disubstituted HepII, and trace amounts of 2-monosubstituted HepII.

The ESI-MS spectra of NMB galE lipid-A-free core OS (Table 9) shows m/z ions characterizing the inner-core region carrying one PEA unit and Glc at HepII (m/z 1254). It was also observed that extra Glc units were added to the inner-core at O-4 of β-Glc (of HepI) (m/z 1416) and at O-7 of HepI (m/z 1578) (Table 9).

The location of the PEA group was determined as described above. GC-MS analysis demonstrated the presence of 2,3-disubstituted HepII, 6-monosubstituted trideuteromethyl-2,3-disubstituted HepII and 7-monosubstituted trideuteromethyl-2,3-disubstituted HepII (data not shown) indicating three inner core variations with Glc at O-3 of HepII, Glc at O-3 and PEA at O-7 of HepII, and Glc at O-3 and PEA at O-6 of HepII (Table 8).

1-D $^{31}$P-NMR studies carried out on NMB galE core OS showed a single resonance at $\delta_P$ 0.82, which did not change chemical shift at higher pH, indicative of a single diester-phosphate entity. A 2-D $^1$H-$^{31}$P correlation NMR experiment showed the through-bond connectivities between the phosphate and the two methylene entities (3.20 ppm and 4.06 ppm) of the PEA, H-7 (4.05 ppm) and H-6 (4.49 ppm) of HepII, thereby confirming two single PEA moieties attached to HepII in NMB galE core OS.

The dominant structure of NMB galE core OS is depicted in FIG. 5C, which shows that NMB galE LOS contains one PEA unit attached to position O-7 of HepII or a PEA at position O-6 of HepII. Structures having Glc attached at O-3 (no PEA) of HepII was present in minor amounts. In addition, some *N. meningitidis* NMB galE strains were able to produce LOS with extra glucose at O-4 of the β-Glc of HepI.

Example 7

Immunogenicity of *N. meningitidis* Gale LOS Conjugates

*N. meningitidis* LOSs from the galE mutant strains (i.e., a truncated OS α-chain) described above in Example 6 (i.e., 6275 galE LOS, H44/76 galE LOS, 89I galE LOS, NMB galE LOS and L11 LOS (L11 LOS has the same structure as 6275 galE LOS)) were de-O-acylated (dLOS) and conjugated to CRM$_{197}$ as described in Example 1. The immunogenic properties of the dLOS conjugates were then evaluated in rabbits and mice.

The ELISA titers of sera from rabbits immunized with monovalent LOS conjugates collected at week 10 are shown in Tables 10-12 below. Wild-type *N. meningitidis* LOS from immunotypes L1-L12, H44/76 and NMB LOS were used as the coating antigen in the ELISA. The pre-immunization titer (i.e., week 0) was less than 1000, indicating only trace amounts of LOS specific antibodies present in the rabbits.

Table 10 shows the reactivity of the antisera generated against the *N. meningitidis* NMB galE LOS conjugate (designated 7350-NMB dLOS-CRM$_{197}$). As described above, NMB LOS has an inner core with Glc attached at O-3 of HepII and PEA attached at O-7 or O-6 of HepII. The NMB galE LOS conjugate (7350-NMB dLOS-CRM$_{197}$) was able to induce high titers of potentially protective IgG antibody binding to wild-type L2, L5, L12 and NMB LOS, and lower titers of IgG binding (<100,000 titer) to L3 (6275), L4, L6, L11 and H44/76 (L3) LOS. The NMB galE LOS conjugate (7350-NMB dLOS-CRM$_{197}$) induced minimal or no titers against L1, L7, L8 (strain M978), and L9 LOS.

TABLE 10

REACTIVITY OF RABBIT ANTISERA GENERATED BY
IMMUNIZATION WITH NMB GALE DLOS-CRM$_{197}$

| LOS Immunotype | ELISA Titer |
|---|---|
| L1 | 2,745 |
| L2 | 258,519 |
| L3 (6275) | 52,782 |
| L4 | 11,320 |
| L5 | 111,506 |
| L6 | 34,361 |
| L7 | 1,236 |
| L8 (M978) | 1,520 |
| L9 | 0 |
| L10 | 1,140 |
| L11 | 29,251 |
| L12 | 133,940 |
| H44/76 (L3) | 28,945 |
| NMB (L2) | 436,224 |

Table 11 shows the reactivity of antisera generated against the *N. meningitidis* H44/76 galE LOS conjugate (7350-H44/76 dLOS-CRM$_{197}$). As described above, H44/76 LOS has an inner core with PEA attached at O-3 PEA of HepII. The H44/76 LOS conjugate (7350-H44/76 dLOS-CRM$_{197}$) induced strong IgG antibody responses to wild-type L1, L5, L7, L8 (strain M978), L9, L10, L11, L12 and H44/76 LOS, while IgG response to wild-type L2, L3 (strain 6275), L4, L6 and NMB LOS was negligible.

TABLE 11

REACTIVITY OF RABBIT ANTISERA GENERATED BY
IMMUNIZATION WITH H44/76 GALE DLOS-CRM$_{197}$

| LOS Immunotype | ELISA Titer |
|---|---|
| L1 | 463,358 |
| L2 | 0 |
| L3 (6275) | 13,456 |
| L4 | 0 |
| L5 | 174,586 |
| L6 | 0 |
| L7 | 311,261 |
| L8 (M978) | 404,234 |
| L9 | 211,045 |
| L10 | 257,939 |
| L11 | 290,582 |
| L12 | 1,372,040 |
| H44/76 (L3) | 1,251,953 |
| NMB (L2) | 22,648 |

Table 12 shows the reactivity of antisera generated against the *N. meningitidis* 89I galE LOS conjugate (7350-L4 dLOS-CRM$_{197}$). As described above, 89I LOS has an inner core with PEA attached at O-6 of HepII. The 89I galE LOS conjugate (7350-L4 dLOS-CRM$_{197}$) induced strong IgG antibody responses to wild-type L4, L6, L12 and NMB LOS, and lower antibody titers against L2, L3 (6275) and L11 LOS. The antibody response to wild-type L1, L5, L7, L8 (M978), L9, L10 and H44/74 (L3) LOS was negligible or absent.

TABLE 12

REACTIVITY OF RABBIT ANTISERA GENERATED
BY IMMUNIZATION WITH 89I GALE DLOS-CRM$_{197}$

| LOS Immunotype | ELISA Titer |
|---|---|
| L1 | 2,916 |
| L2 | 56,518 |
| L3 (6275) | 27,507 |
| L4 | 155,018 |
| L5 | 1,159 |
| L6 | 262,038 |
| L7 | 1,708 |
| L8 (M978) | 2,869 |
| L9 | 0 |
| L10 | 474 |
| L11 | 86,291 |
| L12 | 352,834 |
| H44/76 (L3) | 1,540 |
| NMB (L2) | 168,562 |

The ELISA reactivity patterns of the *N. meningitidis* LOS immunotypes shown in Tables 10-12 were identical when assayed by Western Blot assay (data not shown). These data demonstrate that *N. meningitidis* LOS conjugates, lacking outer core glycan structures (i.e., a truncated OS α-chain), are capable of inducing an immunogenic response against wild-type *N. meningitidis* LOS.

The polyclonal antibody response induced by each *N. meningitidis* LOS conjugate was directed to a PEA dependent, inner core epitope. However, as shown in Tables 10-12, none of the LOS conjugates were able to induce broadly cross-reactive antibodies against all of the immunotypes and phase variants tested. This suggests that an immunogenic composition for inducing a broad immune response against the predominant *N. meningitidis* serogroups (i.e., groups A, B, C, Y and W-135) will require a multivalent LOS conjugate covering all twelve LOS immunotypes. The data of the present invention indicate that the LOS immunogenic composition should comprise at least an LOS component with the following unique inner core PEA/Glc substitutions: (i) PEA linked to O-3 and O-6 position of HepII and PEA linked to O-3 and O-7 position of HepII, (ii) PEA linked to O-6 position of HepII; (iii) Glc linked to O-3 position of HepII and PEA linked to O-6 position of HepII and Glc linked to O-3 position of HepII and PEA linked to O-7 position of HepII; (iv) PEA linked to O-3 position of HepII and (v) Glc linked to O-3 position of HepII.

Example 8

Bactericidal and Opsonophagocytic Activity of Antisera Generated Against *N. meningitidis* GalE LOS Conjugates The biological functionalities of the *N. meningitidis* conjugates described in Example 7 were assayed for bactericidal activity and opsonophagocytic activity against encapsulated *N. meningitidis* strains. Mouse antisera generated against the *N. meningitidis* H44/76 galE LOS conjugate were bactericidal and mediated opsonophagocytic killing of clinical isolate *N. meningitidis* (group B) strain H355. Bactericidal and opsonophagocytic activity was abolished by adsorption of the antisera with de-O-acylated N. meningitidis galE LOS(H1-4) (data not shown).

The bactericidal activity of monovalent H44/76 galE conjugate and tetravalent galE LOS conjugate antisera against strain H44/76 are shown in Table 13. The positive bactericidal activity correlated with protection in infant rat bacteremia model (Example 9, Table 14).

TABLE 13

BACTERICIDAL ACTIVITY OF RABBIT TETRAVALENT LOS ANTISERA AGAINST N. MENINGITIDIS WILD-TYPE STRAIN H44/76

| Rabbit Antisera | Tetravalent Conjugate Composition | BC TITER Nm H44/76 | ELISA Titer Nm H44/76 |
|---|---|---|---|
| Week 0 | galEL4 + galENMB + galEH44/76 + L11 galEH44/76 Positive control | <10 <800 (90%)* 400 1,600 | 1,108 227,411 (wk 10) 938,527 |
| Week 9 | | | |
| Week 10 | | | |

"BC" is bactericidal titer against wild-type H44/76 strain.
"(90%)*" is the BC activity at 1:8000 dilution.
$CRM_{197}$ was used as carrier.

Opsonophagocytosis of N. meningitidis strain H355 was measured by chemiluminiscence assay using antisera before immunization (week 0) and after three immunizations with N. meningitidis H44/76 galE LOS conjugate. The antisera collected at week 8 demonstrated an enhanced chemiluminiscence response relative to antisera before immunization.

Opsonization of N. meningitidis strain 35E (L2) was assessed with antisera from mice immunized with either N. meningitidis NMB galE LOS conjugate (7350-NMB dLOS-$CRM_{197}$) and wild-type N. meningitidis NMB dLOS-$CRM_{197}$ (data not shown). The immune sera (week 8) from mice immunized with the truncated N. meningitidis NMB galE LOS conjugate opsonized N. meningitidis strain 35E (L2) to the same level as antisera from mice immunized with wild-type N. meningitidis NMB dLOS-$CRM_{197}$. These results demonstrate that antibodies generated against truncated N. meningitidis LOS also enhance phagocytosis and/or cause lysis of wild-type N. meningitidis strains.

Example 9

Passive Protection of Rats with Monovalent and Tetravalent N. meningitidis LOS Conjugate Induced Rabbit Antisera Approximately 18-24 hours prior to challenge, 3 to 4 day old Sprague-Dawley rats (10 rats/group) were injected i.p. with 1:5 dilutions of the non-immune and hyperimmune sera from rabbits immunized with monovalent N. meningitidis H44/76 galE dLOS conjugate and N. meningitidis tetravalent galE dLOS conjugate. Rats were challenged with approximately $2.1 \times 10^5$ CFU of N. meningitidis H44/76 per rat. Three hours after the challenge, rats were bled and sacrificed. Aliquots of blood from a cardiac puncture were plated onto GCK media and incubated for 18 hours at 36° C., 5% $CO_2$. Levels of bacteremia were determined by counting colonies on GCK plates after incubation. Results showed (Table 14) that 80% of rats were cleared of bacteremia after administration of antibodies induced by monovalent N. meningitidis H44/76 galE dLOS conjugate antisera and all animals were clear of bacteremia after administration of the antisera from the tetravalent conjugate.

TABLE 14

PASSIVE PROTECTION OF RATS WITH RABBIT ANTISERA GENERATED AGAINST MONOVALENT AND TETRAVALENT LOS CONJUGATED TO $CRM_{197}$

| Rabbit Antiserum | [1]Rat 1 | Rat 2 | Rat 3 | Rat 4 | Rat 5 | Rat 6 | Rat 7 | Rat 8 | Rat 9 | Rat 10 | [2]Avg. ± S.D. | Bacteremic rats/total rats | $BC_{50}$ Titer |
|---|---|---|---|---|---|---|---|---|---|---|---|---|---|
| Normal Sera (wk 0) | 2.14 | 2.80 | 3.63 | 4.32 | 1.10 | 3.72 | 4.36 | 3.84 | 2.89 | 4.89 | 3.37 ± 1.15 | 9/10 | <10 |
| [3]Hyperimmune Sera 1 | 1.10 | 1.10 | 1.10 | 2.24 | 2.76 | 1.10 | 1.10 | 1.10 | 1.10 | 1.10 | 1.38 ± 0.60* | 2/10 | 400 |
| [4]Hyperimmune Sera 2 | 1.10 | 1.10 | 1.10 | 1.10 | 1.10 | 1.10 | 1.10 | 1.10 | 1.10 | — | 1.10 ± (+.3, −1.1)* | 0/9 | >800 |

[1]The numbers in the Rat columns represent $\log_{10}$ CFU per mL of blood.
[2]The average (Avg.) standard deviation (±S.D.) represent the group average $\log_{10}$ CFU per mL of blood ± S.D. in surviving rats after challenge.
[3]Hyperimmune sera 1 was generated with monovalent H44/76 galE LOS conjugated to $CRM_{197}$.
[4]Hyperimmune sera 2 was generated with tetravalent H44/76 galE LOS + NMB galE LOS + 891 galE LOS + L11 LOS conjugated to $CRM_{197}$.
Value of 1.10 $\log_{10}$ CFU per mL blood represents ½ the lower limit of detection (12.5 colonies)
Statistical analysis p < 0.05 Dunnet's method. Lower limit of detection is 1.40 $\log_{10}$ CFU per mL blood.

Example 10

LOS-Protein Conjugation Processes Influence Antibody Specificity

The immunogenicity of *N. meningitidis* LOS conjugated to $CRM_{197}$ through the carboxylate of a KDO residue was compared to immunogenicity of *N. meningitidis* LOS conjugated to $CRM_{197}$ through the amine of PEA residue.

*N. meningitidis* R6 LOS was detoxified (i.e., de-O-acylated, dLOS) by the treatment with 45 mM sodium hydroxide and conjugated to $CRM_{197}$ protein (i) via its KDO residue or (ii) via its PEA residue. PDPH (described in Example 1) was used as a linker to conjugate LOS through a carboxylate group of KDO (i). The resulting conjugate, R6-dLOS-PDPH-$CRM_{197}$, has dLOS covalently attached to the $CRM_{197}$ protein through the following bond: dLOS-CO—NH—NH—CO—$CH_2$—$CH_2$—S—$CH_2$CO—NH-$CRM_{197}$.

For synthesis of LOS conjugates linked through the amino group of PEA (ii), N-succinimidyl 6-[3'-(2-pyridyidithio) propioamido] hexanoate (SPDP) was used a the linker. The SPDP thiolated dLOS was reacted with bromoacetyl groups of activated $CRM_{197}$ protein in the same was as PDPH thiolated dLOS described in Example 1. The resulting thioether linkage in the conjugate R6-dLOS-SPDP-$CRM_{197}$, was dLOS-NH—CO—(CH2)5-NH—CO—CH2-CH2—S—CH2-CO—NH-$CRM_{197}$. Unreacted bromoacetyl groups were "capped" with N-acetyl cysteamine hydrochloride.

The dLOS conjugates were evaluated for immunogenicity in mice, wherein mice were immunized with either R6-dLOS-PDPH-$CRM_{197}$ (KDO) or R6-dLOS-SPDP-$CRM_{197}$ (PEA) conjugates. Antisera from the mice was collected at week 8 and inhibition ELISA assays were performed by adding antisera to plates coated with wild-type *N. meningitidis* NMB LOS. Inhibition in the binding (i.e., LOS competition) of mouse antisera to NMB LOS was evaluated with several wild-type *N. meningitidis* LOSs, before and after removal of the PEA groups by the treatment with HF.

Figure 8A:
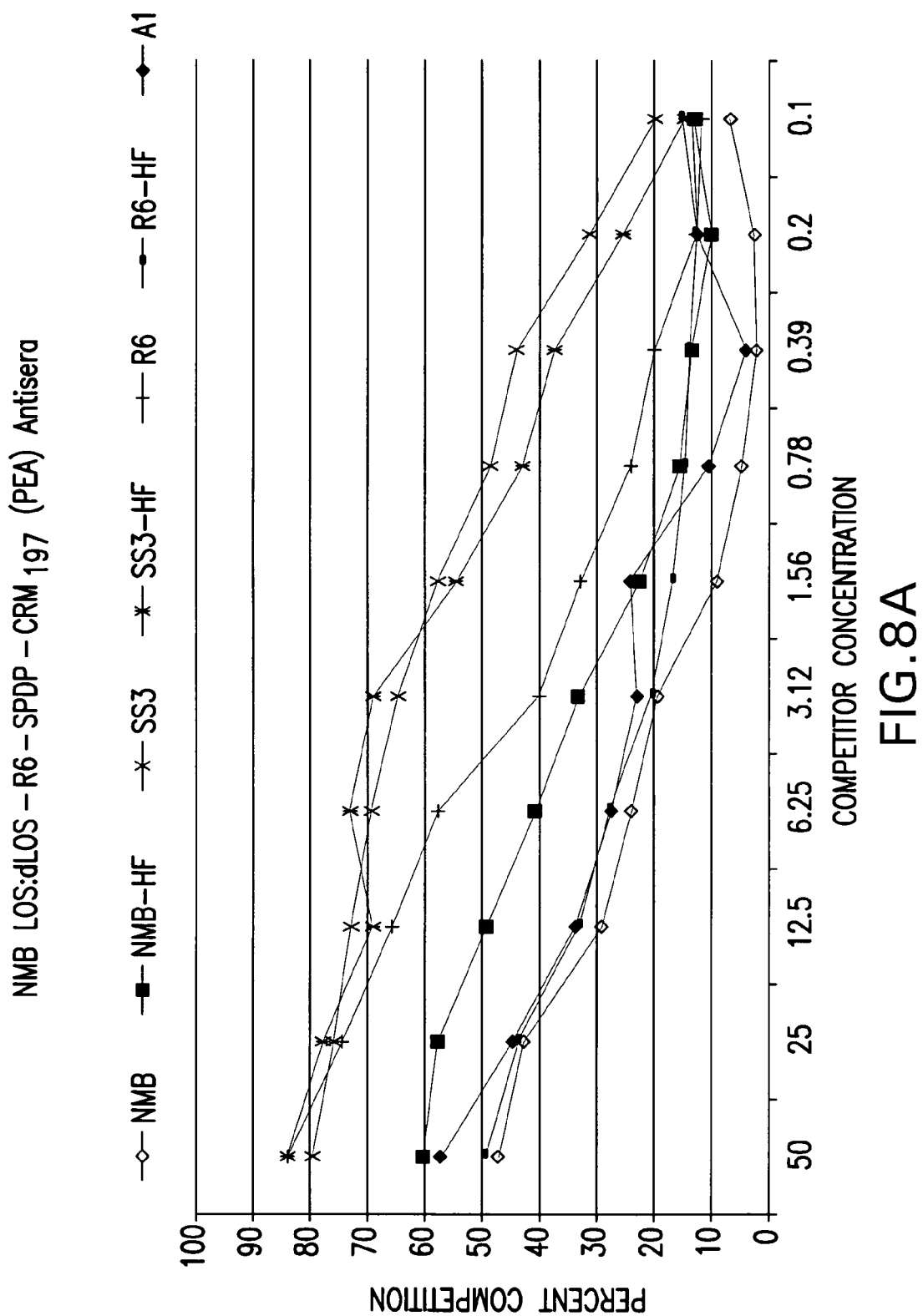
FIGS. 8A and 8B show the immunogenicity of the R6-dLOS-SPDP-$CRM_{197}$ (PEA) conjugate and the dLOS-PDPH-$CRM_{197}$ (KDO), respectively.

The results indicate that antibodies generated to R6-dLOS-SPDP-$CRM_{197}$ (PEA) conjugate (FIG. 8A) are not specific to PEA dependent epitope as indicated by similar competition pattern of PEA+/−meningococcal LOS. This observation indicates that conjugation of LOS via PEA residues destroys the LOS inner core epitope and that the immune response observed is most likely directed to the α-chain oligosaccharide.

Figure 8B:
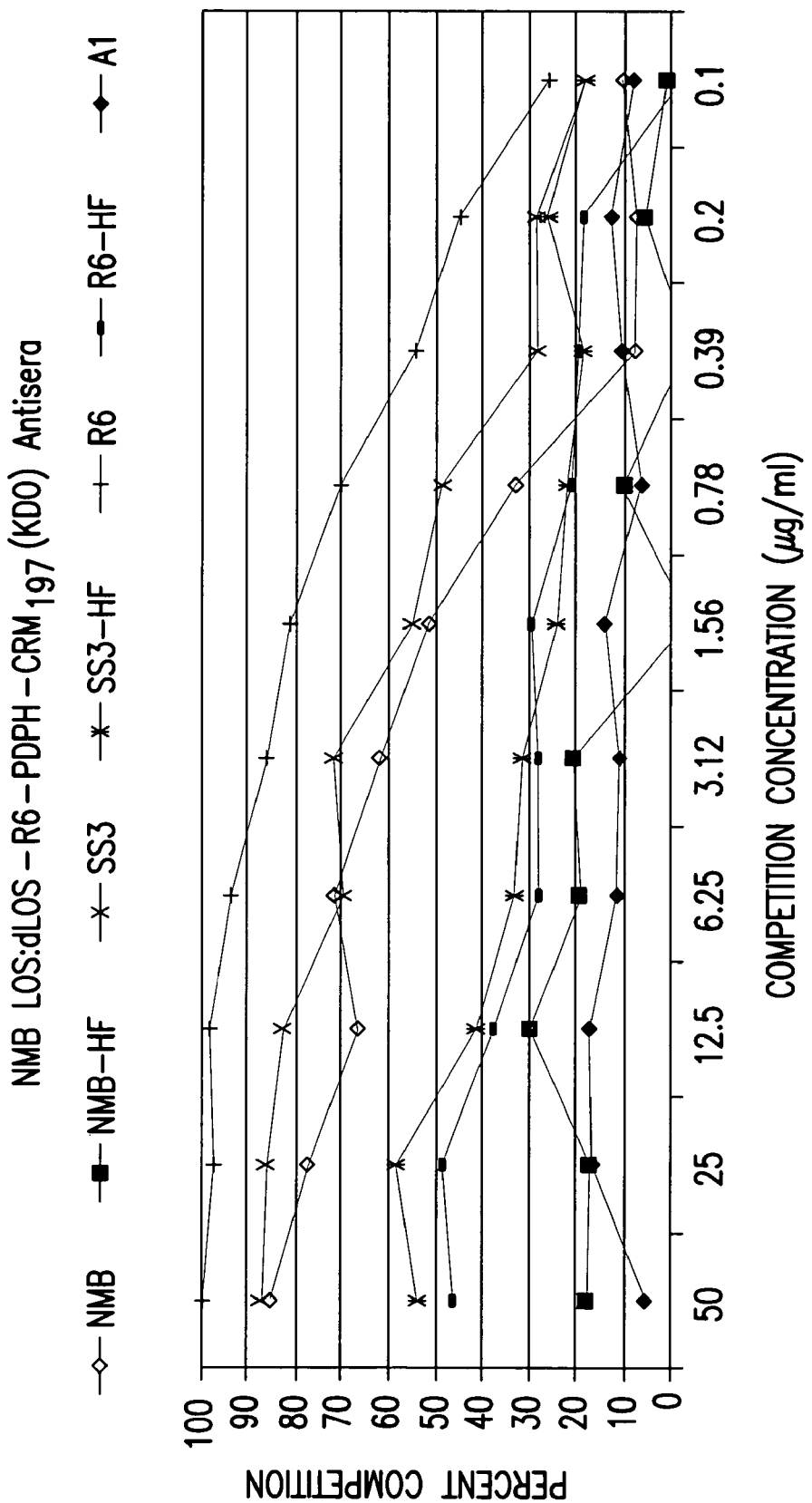
Figure 9:
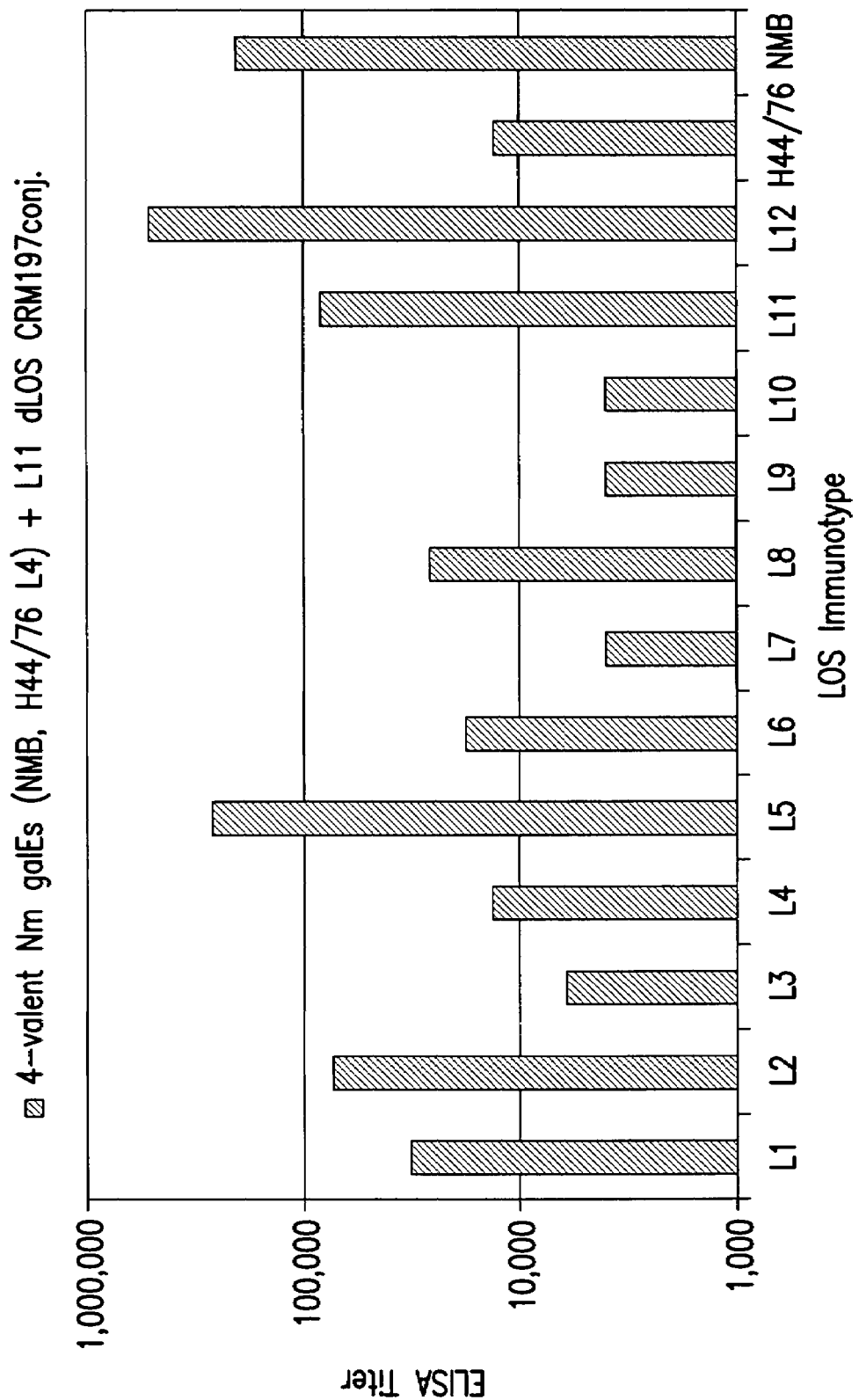
FIG. 9 demonstrates that tetravalent LOS-$CRM_{197}$ conjugate immunogenic compositions induced antibodies in rabbits that react with LOS from all twelve of the LOS immunotypes. The components in the tetravalent LOS-$CRM_{197}$ conjugates comprised a NMB strain LOS inner core (immunotype L2, PEA epitope groups IV and V), a 89I strain LOS inner core (immunotype L4, PEA epitope group III), a H44/76 strain LOS inner core (immunotype L3, PEA epitope group I) and a 7889 strain LOS (immunotype L11, PEA epitope group II).

The R6-dLOS-PDPH-$CRM_{197}$ (KDO) conjugate (FIG. 8B) was able to induce antibodies specific to PEA dependent epitopes as shown by the ability of PEA containing LOSs to inhibit the binding of the vaccine induced antibodies to NMB LOS coated plates. The ability to inhibit the binding was reduced, or in some cases fully abolished, by the removal of PEA by treatment of LOS with HF (FIG. 8B). These results indicate that conjugation of LOS via KDO residues maintains the PEA dependent LOS inner core epitope and that the immune response observed is directed to both a PEA dependent epitope and an α-chain oligosaccharide.

REFERENCES

Andersen et al., "Short-chain lipopolysaccharide mutants of serogroup B *Neisseria meningitidis* of potential value for production of outer membrane vesicle vaccines", *Microb. Pathog.* 19(3):159-168, 1995.

Anonymous (2000). "Enhanced surveillance of suspected meningococcal disease." *CDR Weekly* 9: 78-79.

Bernatowicz and Matsueda, "Preparation of peptide-protein immunogens using N-succinimidyl bromoacetate as a heterobifunctional crosslinking reagent", *Anal. Biochem.*, 155(1):95-102, 1986.

Ciucanu and Kerek, "A simple and rapid method for permethylation of carbohydrates", *Carbohydrate Research*, 131:209-217, 1984.

Covey et. al., *Anal. Chem.*, 63:1193-1200, 1991.

Cox et al., "Identification and localization of glycine in the inner core lipopolysaccharide of *Neisseria meningitidis*", *Eur. J. Biochem.*, 269:4169-4175, 2002[a].

Cox et al., "Structural analysis of the lipooligosaccharide from *Neisseria meningitidis* strain BZ157 galE: localisation of two phosphoethanolamine residues in the inner core oligosaccharide", *Carbohydrate Res.*, 337:1435-1444, 2002[b].

Di Fabio et al., "Structure of the L1 and L6 core oligosaccharide epitopes of *Neisseria meningitidis*", *Can. J. Chem.*, 68:10291034, 1990.

Drazek et al., "A mutation in the *Neisseria gonorrhoeae* rfaD homolog results in altered lipooligosaccharide expression", *J. Bacteriol.*, 177:2321-2327, 1995.

Gamian et al., "Structure of the L2 lipopolysaccharide core oligosaccharides of *Neisseria meningitidis*", *J. Biol. Chem.*, 267(2):922-925, 1992.

Gotschlich, "Genetic locus for the biosynthesis of the variable portion of *Neisseria gonorrhoeae* lipooligosaccharide", *J. Exp. Med.*, 180:2181-2190, 1994.

Grassetti et. al., *Archives of Biochemistry and Biophysics* 119:41-49, 1967.

Gu et al., "Quantitation and biological properties of released and cell-bound lipooligosaccharides from nontypeable *Haemophilus influenzae*", *Infection and Immunity*, 63(10): 4115-4120, 1995.

Gu et al., "Production and characterization of monoclonal antibodies to type 8 lipooligosaccharide of *Neisseria meningitidis*." *Journal of Clinical Microbiology*, 30(8):2047-2053, 1992.

Helander et al., "Chemical structure of the lipopolysaccharide of *Haemophilus influenzae* strain I-69 Rd−/b+. Description of a novel deep-rough chemotype", *Eur. J. Biochem.*, 177(3):483-492, 1988.

Holten, "Serotypes of *Neisseria meningitidis* isolated from patients in Norway during the first six months of 1978", *J. Clin. Microbiol.*, 9(2):186-188, 1979.

Hunt et. al., *Rapid Commun. Mass. Spectrom.* 3:122-124, 1989.

Jennings et al., "The structure of an R-type oligosaccharide core obtained from some lipopolysaccharides of *Neisseria meningitidis*", *Carbohydr. Res.*, 121:233-241, 1983.

Jennings et al., "Cloning and molecular analysis of the galE gene of *Neisseria meningitidis* and its role in lipopolysaccharide biosynthesis", *Mol. Microbiol.*, 10:361-369, 1993.

Kahler et al., "Inner core biosynthesis of lipooligosaccharide (LOS) in *Neisseria meningitidis* serogroup B: Identification and role in LOS assembly of the α1,2 N-acetylglucosamine transferase (rfaK)", *J. Bacteriol.*, 178:1265-1273, 1996[a].

Kahler et al., "Two glycosyltransferase genes, lgtF and rfaK, constitute the lipooligosaccharide ice (inner core extension) biosynthesis operon of *Neisseria meningitidis*", *J. Bacteriol.*, 178:6677-6684, 1996[b].

Kim et al., "Electromorphic characterization and description of conserved epitopes of the lipooligosaccharides of group A *Neisseria meningitidis*", *Infection and Immunity*, 56(10):2631-2638, 1988.

Kogan et al., "Structural basis of the *Neisseria meningitidis* immunotypes including the L4 and L7 immunotypes", *Carbohydr. Res.*, 298(3):191-199, 1997.

Kohler and Milstein, "Continuous cultures of fused cells secreting antibody of predefined specificity", *Nature*, 256 (5517):495-497, 1975.

Kohler and Milstein, "Derivation of specific antibody-producing tissue culture and tumor lines by cell fusion," *Eur. J. Immunol.*, 6(7):511-519, 1976.

Lee et al., "Microheterogeneity of *Neisseria* lipooligosaccharide: analysis of a UDP-glucose 4-epimerase mutant of *Neisseria meningitidis* NMB," *Infection and Immunity*, 63(7):2508-2515, 1995.

Leontein et al., "Assignment of absolute configuration of sugars by g.l.c of their acetylated glycosides formed from chiral alcohols", *Carbohydrate Research*, 62:359-362, 1978.

Loo et. al., *Science*, 248:201-204, 1990.

Loo et. al., *Anal. Chem.*, 63:2488-2499, 1991.

Mandrell et al., "Lipooligosaccharides (LOS) of *Neisseria gonorrhoeae* and *Neisseria meningitidis* have components that are immunochemically similar to precursors of human blood group antigens. Carbohydrate sequence specificity of the mouse monoclonal antibodies that recognize cross-reacting antigens on LOS and human erythrocytes", *J. Exp. Med.*, 168(1):107-126, 1988.

Mandrell and Zollinger, "Lipopolysaccharide serotyping of *Neisseria meningitidis* by hemagglutination inhibition", *Infection and Immunity*, 16(2): 471-5, 1977.

McLeod Griffiss et al., (2000). "Structural relationships and sialylation among meningococcal L1, L8, and L3,7 lipooligosaccharide serotypes", *J. Biol. Chem.*, 275(13):9716-9724, 2000.

Michon et al., "Structure of the L5 lipopolysaccharide core oligosaccharides of *Neisseria meningitidis*", *J. Biol. Chem.*, 265(13):7243-7247, 1990.

Morrissey, "Silver stain for proteins in polyacrylamide gels: a modified procedure with enhanced uniform sensitivity", *Anal. Biochem.*, 117(2):307-310, 1981.

Mountzouros and Howell, "Detection of Complement-Mediated Antibody-Dependent Bactericidal Activity in a Fluorescence-Based Serum Bactericidal Assay for Group B *Neisseria meningitidis*", *Journal Of Clinical Microbiology*, 38(8):2878-2884, 2000.

Pavliak et al., "Structure of the sialylated L3 lipopolysaccharide of *Neisseria meningitidis*", *J. Biol. Chem.*, 268(19): 14146-14152, 1993.

Plested et al. "Functional opsonic activity of human serum antibodies to inner core lipopolysaccharide (galE) of serogroup B meningococci measured by flow cytometry", *Infection & Immunity* 69(5): 3203-3213, 2001.

Plested et al., "Conservation and accessibility of an inner core lipopolysaccharide epitope of *Neisseria meningitidis*." *Infection and Immunity*, 67(10):5417-5426, 1999.

Rahman et al., "The structure of the lipo-oligosaccharide (LOS) from the alpha-1,2-N-acetyl glucosamine transferase (rfaK(NMB)) mutant strain CMK1 of *Neisseria meningitidis*: implications for LOS inner core assembly and LOS-based vaccines", *Glycobiology*, 11 (8):703-709, 2001.

Rahman et al., "The lipo-oligosaccharide (LOS) of *Neisseria meningitidis* serogroup B strain NMB contains L2, L3, and novel oligosaccharides, and lacks the lipid-A 4'-phosphate substituent", *Carbohydr. Res.*, 307(3-4):311-324, 1998.

Sandlin et al., "Genetic basis of pyocin resistance in *Neisseria gonorrhoeae*", *J. Bacteriol.*, 176:6869-6876, 1994.

Sawardeker et al., "Quantitative determination of monosaccharides as their alditol acetates by gas liquid chromatography", *Analytical Chemistry*, 37:1602-1604, 1967

Scholten et al., "Lipo-oligosaccharide immunotyping of *Neisseria meningitidis* by whole-cell ELISA with monoclonal antibodies", *J. Med. Microbiol.*, 41:236-243, 1994.

Smith et al., "Measurement of protein using bicinchoninic acid", *Anal. Biochem.*, 150:76-85, 1985.

Stephens et al., "Tn916-generated, lipo-oligosaccharide mutants of *Neisseria meningitidis* and *Neisseria gonorrhoeae*", *Infection and Immunity*, 62(7): 2947-52, 1994.

Verheul et al., "Minimal oligosaccharide structures required for induction of immune responses against meningococcal immunotype L1, L2, and L3,7,9 lipopolysaccharides determined by using synthetic oligosaccharide-protein conjugates", *Infection and Immunity*, 59(10): 3566-3573, 1991.

Verheul et al., "Preparation, characterization, and immunogenicity of meningococcal immunotype L2 and L3,7,9 phosphoethanolamine group-containing oligosaccharide-protein conjugates", *Infection and Immunity*, 59(3): 843-851, 1991.

Verheul et al., "Development, characterization, and biological properties of meningococcal immunotype L3,7,(8),9-specific monoclonal antibodies", *Clin. Diagn. Lab Immunol.*, 1 (6): 729-736, 1994.

Verheul et al., "Meningococcal lipopolysaccharides: virulence factor and potential vaccine component", *Microbiol. Rev.*, 57(1): 34-49, 1993[a].

Verheul et al., "Meningococcal lipopolysaccharide (LPS)-derived oligosaccharide-protein conjugates evoke outer membrane protein—but not LPS-specific bactericidal antibodies in mice: influence of adjuvants", *Infection and Immunity*, 61(1): 187-196, 1993[b].

Virji et al., "The role of pili in the interactions of pathogenic *Neisseria* with cultured human endothelial cells", *Mol. Microbiol.*, 5(8):1831-41, 1991.

Wakarchuk et al., "Structure of an alpha-2,6-sialylated lipooligosaccharide from *Neisseria meningitidis* immunotype L1", *Eur. J. Biochem.*, 254(3):626-633, 1998.

Waravdekar and Saslaw, *J. Biol. Chem.*, 234:1945-1950, 1959.

Westphal and Jann, "Bacterial lypopolysaccharides: Extraction with phenol-water and further applications of the procedure", *Methods Carbohydrate Chemistry*, 5:83-91, 1965.

Wu et al., "A method for purification of bacterial R-type lipopolysaccharides (lipooligosaccharides)", *Anal. Biochem.*, 160:281-289, 1987.

Yamasaki et al., "Epitope expression of gonococcal lipooligosaccharide (LOS). Importance of the lipoidal moiety for expression of an epitope that exists in the oligosaccharide moiety of LOS", *Mol. Immunol.*, 25(8):799-809, 1988.

Zollinger and Mandrell, "Outer-membrane protein and lipopolysaccharide serotyping of *Neisseria meningitidis* by inhibition of a solid-phase radioimmunoassay", *Infection and Immunity*, 18(2):424-433, 1977.

Zollinger and Mandrell, "Importance of complement source in bactericidal activity of human antibody and murine monoclonal antibody to meningococcal group B polysaccharide", *Infection and Immunity*, 40(1):257-264, 1983.

Zollinger and Mandrell, "Type specific antigens of group A *Neisseria meningitidis*: lipooligosaccharide and heat-modifiable outer membrane proteins", *Infection and Immunity*, 28:451-458, 1980.

Zhou et al., "Lipooligosaccharide biosynthesis in the pathogenic *Neisseria*. Cloning, identification, and characterization of the phosphorglucomutase gene", *J. Biol. Chem.*, 269:11162-11169, 1994[a].

Zhou et al., "Lipooligosaccharide biosynthesis in *Neisseria gonorrheae*: cloning, identification and characterization of the α1,5 heptosyltransferase I gene (rfaC)", *Mol. Microbiol.*, 14:609-618, 1994[b].

What is claimed is:

1. An isolated and purified *Neisseria meningitidis* lipo-oligosaccharide (LOS) inner core molecule comprising the following structure:

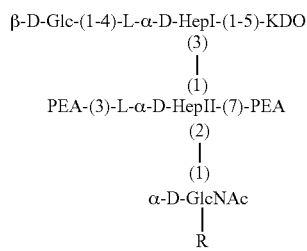

wherein PEA is 2-aminoethyl phosphate, Glc is D-glucopyranose, KDO is 2-keto-3-deoxyoctonate, Hep is L-glycero-D-manno-heptose, GlcNAc is N-acetylglucosamine and R is O-Acetyl or H.

2. The inner core molecule of claim 1, further comprising a lipid-A component covalently attached to the KDO residue of the inner core.

3. The inner core molecule of claim 2, wherein the lipid-A component is de-O-acylated.

4. The inner core molecule of claim 1, wherein the LOS is isolated from a *N. meningitidis* strain having a mutation in one or more genes selected from the group consisting of galE, pgm and rfaK.

5. The inner core molecule of claim 4, wherein at least one mutation is a galE mutation.

6. The inner core molecule of claim 1, wherein the LOS inner core molecule is conjugated to a carrier protein.

7. The inner core molecule of claim 6, wherein the LOS inner core molecule is conjugated to a carrier protein by means of a linker molecule.

8. The inner core molecule of claim 7, wherein the inner core molecule is covalently attached to the linker molecule at a carboxylic acid of a KDO residue of the inner core.

9. The inner core molecule of claim 8, wherein the linker molecule is 3-(2-pyridyldithio)-propionyl hydrazide (PDPH).

10. The inner core molecule of claim 7, wherein the carrier protein is selected from the group consisting of a tetanus toxin, a diphtheria toxin, a mutant diphtheria toxin, a $CRM_{197}$ protein, a pseudomonas exotoxin A protein, a cholera toxin (CT) protein, a cholera toxin mutant CT-E29H protein, a Group A streptococcal toxin protein, a *Streptococcus pneumoniae* pneumolysin protein, a filamentous haemagglutinin (FHA) protein, a *Bordetella pertussis* FHA fragment protein, a *N. gonorrheae* pilin protein, a *N. meningitidis* pilin protein, a *N. gonorrheae* outer membrane protein, a *N. meningitidis* ORF 2086 protein, a *Streptococcus* C5a peptidase and a staphylococcal MSCRAMM protein.

11. The inner core molecule of claim 10, wherein the carrier protein is a $CRM_{197}$ protein, a *Streptococcus* C5a peptidase or a *N. meningitidis* ORF 2086 protein.

12. The inner core molecule of claim 1, wherein the molecule is admixed with one or more *N. meningitidis* ORF 2086 proteins.

13. An isolated and purified LOS inner core composition comprising at least (i) a *N. meningitidis* LOS inner core molecule comprising a β-chain heptose residue (HepII) residue comprising an O-3 linked 2-aminoethyl phosphate (PEA) and an O-6 linked PEA and (ii) a *N. meningitidis* LOS inner core molecule comprising a HepII residue comprising an O-3 linked PEA and an O-7 linked PEA.

14. The inner core composition of claim 13, wherein the LOS inner core molecules (i) and (ii) comprise the following structures:

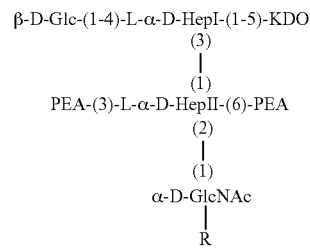

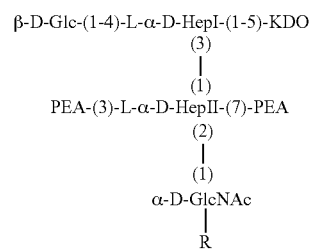

wherein Glc is D-glucopyranose, KDO is 2-keto-3-deoxyoctonate, Hep is L-glycero-D-manno-heptose, GlcNAc is N-acetylglucosamine and R is O-Acetyl or H.

15. The inner core composition of claim 13, further comprising one or more LOS inner core molecules of the following structures:

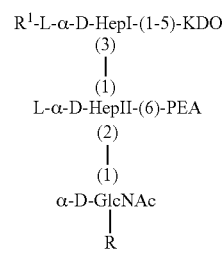

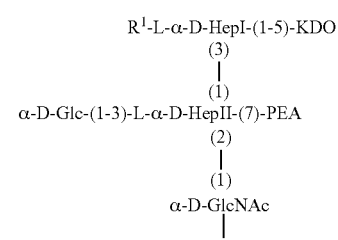

-continued

R¹-L-α-D-HepI-(1-5)-KDO
                     (3)
                      |
                     (1)
PEA-(3)-L-α-D-HepII
         (2)
          |
         (1)
α-D-GlcNAc
    |
    R

R¹-L-α-D-HepI-(1-5)-KDO
                     (3)
                      |
                     (1)
PEA-(3)-L-α-D-HepII-(6)-PEA
         (2)
          |
         (1)
α-D-GlcNAc
    |
    R

R¹-L-α-D-HepI-(1-5)-KDO
                     (3)
                      |
                     (1)
PEA-(3)-L-α-D-HepII-(7)-PEA
         (2)
          |
         (1)
α-D-GlcNAc
    |
    R

R¹-L-α-D-HepI-(1-5)-KDO        R¹-L-α-D-HepI-(1-5)-KDO
                     (3)                            (3)
                      |                              |
                     (1)                            (1)
α-D-Glc-(1-3)-L-α-D-HepII-(6)-PEA    L-α-D-HepII-(7)-PEA
              (2)                         (2)
               |                           |
              (1)                         (1)
         α-D-GlcNAc                  α-D-GlcNAc
             |                           |
             R                           R

R¹-L-α-D-HepI-(1-5)-KDO
                     (3)
                      |
                     (1)
α-D-Glc-(1-3)-L-α-D-HepII
              (2)
               |
              (1)
         α-D-GlcNAc
             |
             R

R¹-L-α-D-HepI-(1-5)-KDO
                     (3)
                      |
                     (1)
Gly-PEA-(3)-L-α-D-HepII
             (2)
              |
             (1)
        α-D-GlcNAc
            |
            R

-continued

PCho-Glc
   (1)
    |
   (7)
R¹-L-α-D-HepI-(1-5)-KDO
                     (3)
                      |
                     (1)
PEA-(3)-L-α-D-HepII
         (2)
          |
         (1)
α-D-GlcNAc
    |
    R

R¹-L-α-D-HepI-(1-5)-KDO
                     (3)
                      |
                     (1)
Gly-PEA-(3)-L-α-D-HepII-(6)-PEA
             (2)
              |
             (1)
        α-D-GlcNAc
            |
            R

R¹-L-α-D-HepI-(1-5)-KDO
                     (3)
                      |
                     (1)
Gly-PEA-(3)-L-α-D-HepII-(7)-PEA
             (2)
              |
             (1)
        α-D-GlcNAc
            |
            R

Glc
(1)
 |
(7)
R¹-L-α-D-HepI-(1-5)-KDO        R¹-L-α-D-HepI-(1-5)-KDO
                     (3)                            (3)
                      |                              |
                     (1)                            (1)
PEA-(3)-L-α-D-HepII           Gly-PEA-(3)-L-α-D-HepII-(6)-PEA
         (2)                              (2)
          |                                |
         (1)                              (1)
α-D-GlcNAc-R                         α-D-GlcNAc
                                         |
                                         R

R¹-L-α-D-HepI-(1-5)-KDO
                     (3)
                      |
                     (1)
Gly-PEA-(3)-L-α-D-HepII-(7)-PEA
             (2)
              |
             (1)
        α-D-GlcNAc
            |
            R

R¹-L-α-D-HepI-(1-5)-KDO
                     (3)
                      |
                     (1)
Gly-PEA-(3)-L-α-D-HepII
             (2)
              |
             (1)
        α-D-GlcNAc
            |
            R wherein Glc is D-glucopyranose, KDO is 2-keto-3-deoxyoctonate, Hep is L-glycero-D-manno-heptose, GlcNAc is N-acetylglucosamine, Gly is glycine, PCho is phosphorylcholine, R is O-Acetyl or H and $R^1$ is β-D-Glc-(1-4), Glc(1-4)-β-D-Glc-(1-4) or H.

16. The inner core composition of claim 13, further comprising one or more *N. meningitidis* ORF 2086 proteins.

17. The inner core composition of claim 13, further comprising a lipid-A component covalently attached to a KDO residue of one or more of the inner core molecules.

18. The inner core composition of claim 17, wherein the lipid-A portion is de-O-acylated.

19. The inner core composition of claim 13, wherein the inner core molecules are isolated from a *N. meningitidis* strain having a mutation in one or more genes selected from the group consisting of galE, pgm and rfaK.

20. The inner core composition of claim 19, wherein at least one mutation is a galE mutation.

21. The inner core composition of claim 13, wherein the inner core molecules are conjugated to a carrier protein.

22. The inner core composition of claim 21, wherein the inner core molecules are conjugated to a carrier protein by means of a linker molecule.

23. The inner core composition of claim 22, wherein the inner core molecules are covalently attached to the linker molecule at a carboxylic acid of a KDO residue of the inner core.

24. The inner core composition of claim 23, wherein the linker molecule is 3-(2-pyridyldithio)-propionyl hydrazide (PDPH).

25. The inner core composition of claim 21, wherein the carrier protein is selected from the group consisting of a tetanus toxin, a diphtheria toxin, a mutant diphtheria toxin, a $CRM_{197}$ protein, a pseudomonas exotoxin A protein, a cholera toxin (CT) protein, a cholera toxin mutant CT-E29H protein, a Group A streptococcal toxin protein, a *Streptococcus pneumoniae* pneumolysin protein, a filamentous haemagglutinin (FHA) protein, a *Bordetella pertussis* FHA fragment protein, a *N. gonorrheae* pilin protein, a *N. meningitidis* pilin protein, a *N. gonorrheae* outer membrane protein, a *N. meningitidis* ORF 2086 protein, a *Streptococcus* C5a peptidase and a staphylococcal MSCRAMM protein.

26. The inner core composition of claim 25, wherein the carrier protein is a $CRM_{197}$ protein, a *Streptococcus* C5a peptidase or *N. meningitidis* ORF 2086 protein.

27. An immunogenic composition comprising (i) a *N. meningitidis* LOS inner core molecule comprising a β-chain heptose residue (HepII) comprising an O-3 linked 2-aminoethyl phosphate (PEA) and an O-6 linked PEA, (ii) a *N. meningitidis* LOS inner core molecule comprising a HepII residue comprising an O-3 linked PEA and an O-7 linked PEA, and (iii) a pharmaceutically acceptable carrier.

28. The immunogenic composition of claim 27, wherein the inner core molecules (i) and (ii) comprise the following structures:

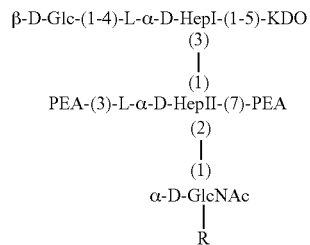

-continued

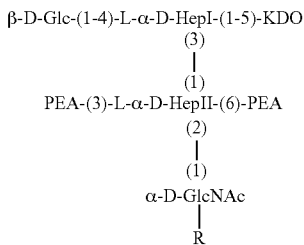

wherein Glc is D-glucopyranose, KDO is 2-keto-3-deoxyoctonate, Hep is L-glycero-D-manno-heptose, GlcNAc is N-acetylglucosamine and R is O-Acetyl or H.

29. The immunogenic composition of claim 27, further comprising one or more *N. meningitidis* LOS inner core molecules of the following structures:

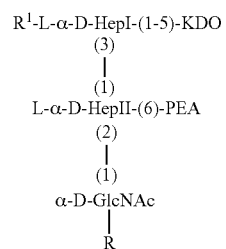

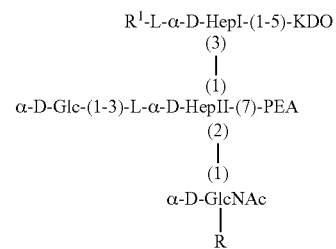

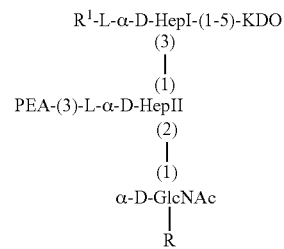

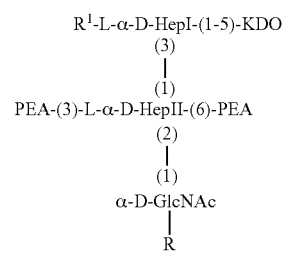

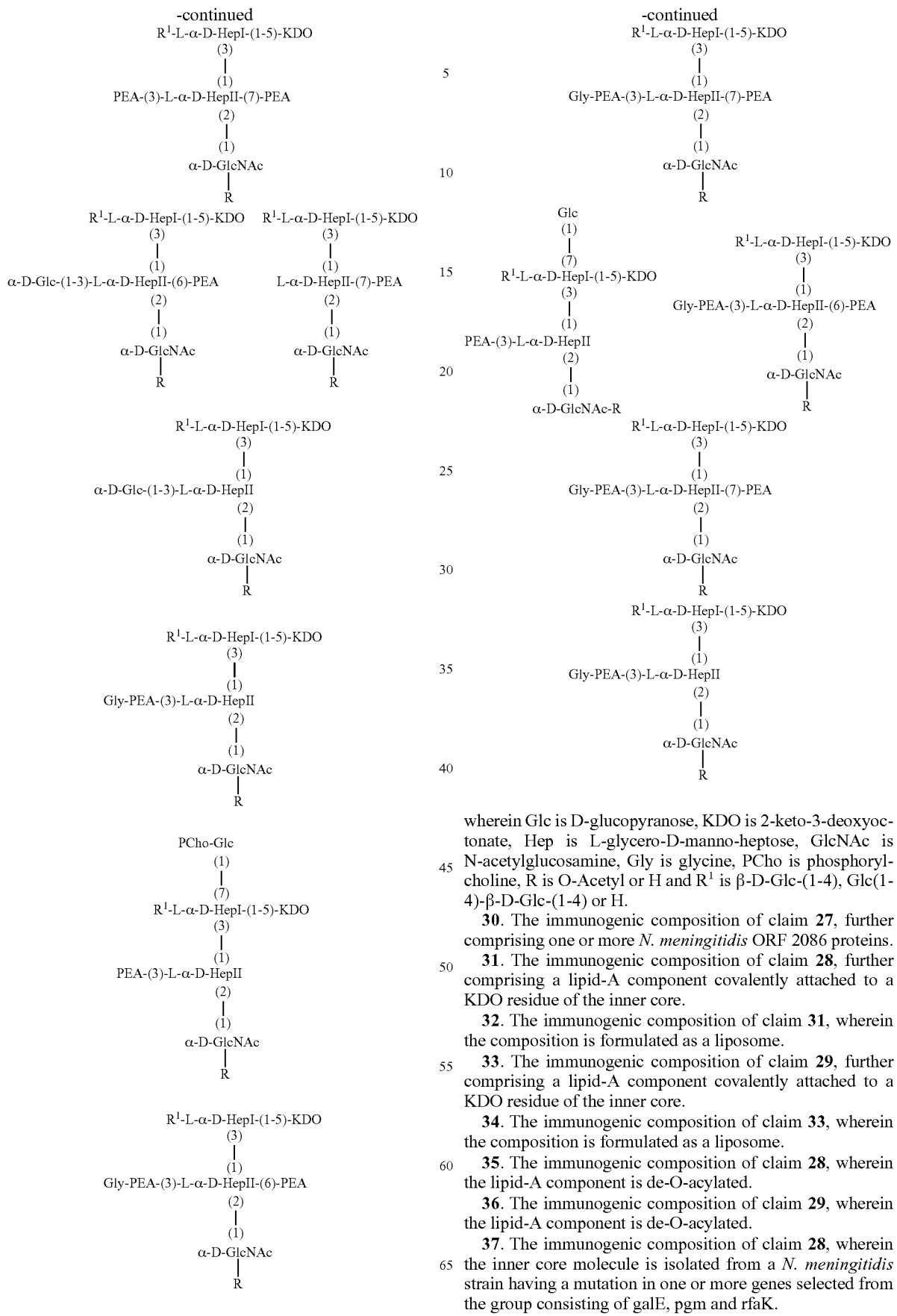

wherein Glc is D-glucopyranose, KDO is 2-keto-3-deoxyoctonate, Hep is L-glycero-D-manno-heptose, GlcNAc is N-acetylglucosamine, Gly is glycine, PCho is phosphorylcholine, R is O-Acetyl or H and $R^1$ is β-D-Glc-(1-4), Glc(1-4)-β-D-Glc-(1-4) or H.

30. The immunogenic composition of claim 27, further comprising one or more *N. meningitidis* ORF 2086 proteins.

31. The immunogenic composition of claim 28, further comprising a lipid-A component covalently attached to a KDO residue of the inner core.

32. The immunogenic composition of claim 31, wherein the composition is formulated as a liposome.

33. The immunogenic composition of claim 29, further comprising a lipid-A component covalently attached to a KDO residue of the inner core.

34. The immunogenic composition of claim 33, wherein the composition is formulated as a liposome.

35. The immunogenic composition of claim 28, wherein the lipid-A component is de-O-acylated.

36. The immunogenic composition of claim 29, wherein the lipid-A component is de-O-acylated.

37. The immunogenic composition of claim 28, wherein the inner core molecule is isolated from a *N. meningitidis* strain having a mutation in one or more genes selected from the group consisting of galE, pgm and rfaK.

38. The immunogenic composition of claim 37, wherein at least one mutation is a galE mutation.

39. The immunogenic composition of claim 29, wherein the one or more inner core molecule are isolated from a *N. meningitidis* strain having a mutation in one or more genes selected from the group consisting of galE, pgm and rfaK.

40. The immunogenic composition of claim 39, wherein at least one mutation is a galE mutation.

41. The immunogenic composition of claim 28, wherein the inner core molecule is conjugated to a carrier protein.

42. The immunogenic composition of claim 41, wherein the inner core molecule is conjugated to a carrier protein by means of a linker molecule.

43. The immunogenic composition of claim 42, wherein the inner core molecule is covalently attached to the linker molecule at a carboxylic acid of a KDO residue of the inner core.

44. The immunogenic composition of claim 43, wherein the linker molecule is 3-(2-pyridyldithio)-propionyl hydrazide (PDPH).

45. The immunogenic composition of claim 41, wherein the carrier protein is selected from the group consisting of a tetanus toxin, a diphtheria toxin, a mutant diphtheria toxin, a $CRM_{197}$ protein, a pseudomonas exotoxin A protein, a cholera toxin (CT) protein, a cholera toxin mutant CT-E29H protein, a Group A streptococcal toxin protein, a *Streptococcus pneumoniae* pneumolysin protein, a filamentous haemagglutinin (FHA) protein, a *Bordetella pertussis* FHA fragment protein, a *N. gonorrheae* pilin protein, a *N. meningitidis* pilin protein, a *N. gonorrheae* outer membrane protein, a *N. meningitidis* ORF 2086 protein, a *Streptococcus* C5a peptidase and a staphylococcal MSCRAMM protein.

46. The immunogenic composition of claim 45, wherein the carrier protein is a $CRM_{197}$ protein, a *Streptococcus* C5a peptidase or a *N. meningitidis* ORF 2086 protein.

47. The immunogenic composition of claim 29, wherein the one or more inner core molecule are conjugated to a carrier protein.

48. The immunogenic composition of claim 47, wherein the one or more inner core molecule are conjugated to a carrier protein by means of a linker molecule.

49. The immunogenic composition of claim 48, wherein the one or more inner core molecules are covalently attached to the linker molecule at a carboxylic acid of a KDO residue of the inner core.

50. The immunogenic composition of claim 49, wherein the linker molecule is PDPH.

51. The immunogenic composition of claim 47, wherein the carrier protein is selected from the group consisting of a tetanus toxin, a diphtheria toxin, a mutant diphtheria toxin, a $CRM_{197}$ protein, a pseudomonas exotoxin A protein, a cholera toxin (CT) protein, a cholera toxin mutant CT-E29H protein, a Group A streptococcal toxin protein, a *Streptococcus pneumoniae* pneumolysin protein, a filamentous haemagglutinin (FHA) protein, a *Bordetella pertussis* FHA fragment protein, a *N. gonorrheae* pilin protein, a *N. meningitidis* pilin protein, a *N. gonorrheae* outer membrane protein, a *N. meningitidis* ORF 2086 protein, a *Streptococcus* C5a peptidase and a staphylococcal MSCRAMM protein.

52. The immunogenic composition of claim 51, wherein the carrier protein is a $CRM_{197}$ protein, a *Streptococcus* C5a peptidase or a *N. meningitidis* ORF 2086 protein.

53. The immunogenic composition of claim 28, further comprising one or more adjuvants.

54. The immunogenic composition of claim 53, wherein the one or more adjuvants are selected from the group consisting of GM-CSF, 529SE, 529AF, IL-12, aluminum phosphate, aluminum hydroxide, *Mycobacterium tuberculosis*, *Bordetella pertussis*, bacterial lipopolysaccharides, aminoalkyl glucosamine phosphate compounds, MPL (3-O-deacylated monophosphoryl lipid A), Quil A, QS-21, a pertussis toxin (PT), an *E. coli* heat-labile toxin (LT), a cholera toxin (CT), IL-1 α, IL-1 β, IL-2, IL-4, IL-5, IL-6, IL-7, IL-8, IL-10, IL-13, IL-14, IL-15, IL-16, IL-17, IL-18, interferon-α, interferon-β, interferon-γ, granulocyte colony stimulating factor, tumor necrosis factor α and tumor necrosis factor β.

55. The immunogenic composition of claim 29, further comprising one or more adjuvants.

56. The immunogenic composition of claim 55, wherein the one or more adjuvants are selected from the group consisting of GM-CSF, 529SE, 529AF, IL-12, aluminum phosphate, aluminum hydroxide, *Mycobacterium tuberculosis*, *Bordetella pertussis*, bacterial lipopolysaccharides, aminoalkyl glucosamine phosphate compounds, MPL (3-O-deacylated monophosphoryl lipid A), Quil A, QS-21, a pertussis toxin (PT), an *E. Coli* heat-labile toxin (LT), a cholera toxin (CT), IL-1 α, IL-1 β, IL-2, IL-4, IL-5, IL-6, IL-7, IL-8, IL-10, IL-13, IL-14, IL-15, IL-16, IL-17, IL-18, interferon-α, interferon-βp, interferon-γ, granulocyte colony stimulating factor, tumor necrosis factor α and tumor necrosis factor β.

57. The immunogenic composition of claim 28, further comprising one or more antigens selected from the group consisting of a polypeptide, a polypeptide fragment, a carbohydrate, an oligosaccharide, a lipid, a lipooligosaccharide, a polysaccharide, a capsular polysaccharide, an oligosaccharide-protein conjugate, a polysaccharide-protein conjugate, a peptide-protein conjugate, an oligosaccharide-peptide conjugate, a polysaccharide-peptide conjugate, a protein-protein conjugate, a lipooligosaccharide-protein conjugate and a polysaccharide-protein conjugate.

58. The immunogenic composition of claim 57, wherein the one or more antigens are isolated from *N. meningitidis*.

59. The immunogenic composition of claim 57, wherein one of the one or more antigens is a *Streptococcus* C5a peptidase or a *N. meningitidis* ORF 2086 protein.

60. The immunogenic composition of claim 59, wherein the antigen is one or more ORF 2086 proteins.

61. The immunogenic composition of claim 29, further comprising one or more antigens selected from the group consisting of a polypeptide, a polypeptide fragment, a carbohydrate, an oligosaccharide, a lipid, a lipooligosaccharide, a polysaccharide, a capsular polysaccharide, an oligosaccharide-protein conjugate, a polysaccharide-protein conjugate, a peptide-protein conjugate, an oligosaccharide-peptide conjugate, a polysaccharide-peptide conjugate, a protein-protein conjugate, a lipooligosaccharide-protein conjugate and a polysaccharide-protein conjugate.

62. The immunogenic composition of claim 61, wherein the one or more antigens are isolated from *N. meningitidis*.

63. The immunogenic composition of claim 61, wherein one of the one or more antigens is a *Streptococcus* C5a peptidase or a *N. meningitidis* ORF 2086 protein.

64. The immunogenic composition of claim 63, wherein the antigen is one or more ORF 2086 proteins.

* * * * *